(12) United States Patent
DiLorenzo et al.

(10) Patent No.: US 8,318,670 B2
(45) Date of Patent: Nov. 27, 2012

(54) ANTIGENS TARGETED BY PATHOGENIC AI4 T CELLS IN TYPE 1 DIABETES AND USES THEREOF

(75) Inventors: Teresa P. DiLorenzo, Bayside, NY (US); Scott M. Lieberman, Philadelphia, PA (US); David V. Serreze, Ellsworth, ME (US)

(73) Assignees: Albert Einstein College of Medicine of Yeshiva University, Bronx, NY (US); The Jackson Laboratory, Bar Harbor, ME (US)

( * ) Notice: Subject to any disclaimer, the term of this patent is extended or adjusted under 35 U.S.C. 154(b) by 1033 days.

(21) Appl. No.: 11/658,457

(22) PCT Filed: Jul. 26, 2005

(86) PCT No.: PCT/US2005/026315
§ 371 (c)(1),
(2), (4) Date: Jun. 24, 2009

(87) PCT Pub. No.: WO2006/023211
PCT Pub. Date: Mar. 2, 2006

(65) Prior Publication Data
US 2010/0009923 A1  Jan. 14, 2010

Related U.S. Application Data

(60) Provisional application No. 60/592,060, filed on Jul. 29, 2004.

(51) Int. Cl.
*A61K 38/03* (2006.01)
*C07K 7/06* (2006.01)
(52) U.S. Cl. .................. 514/7.3; 514/21.6; 530/328
(58) Field of Classification Search .................. None
See application file for complete search history.

(56) References Cited

U.S. PATENT DOCUMENTS

| | | | | |
|---|---|---|---|---|
| 5,552,282 | A * | 9/1996 | Caskey et al. | 435/325 |
| 6,855,546 | B1 * | 2/2005 | Strous et al. | 435/375 |
| 2002/0048763 | A1 * | 4/2002 | Penn et al. | 435/6 |
| 2002/0132247 | A1 | 9/2002 | Delaney et al. | |
| 2003/0078374 | A1 * | 4/2003 | Roberts et al. | 530/350 |
| 2003/0190323 | A1 | 10/2003 | Cohen et al. | |
| 2007/0083334 | A1 * | 4/2007 | Mintz et al. | 702/19 |
| 2008/0153112 | A1 | 6/2008 | DiLorenzo et al. | |
| 2009/0137485 | A1 | 5/2009 | DiLorenzo et al. | |

FOREIGN PATENT DOCUMENTS

CN  1293252 A  *  5/2001
WO  WO 02086122 A2  *  10/2002

OTHER PUBLICATIONS

Machine Translation of CN 1293252 A (May 2, 2001).*
Lieberman S M et al., Identification of the β cell antigen targeted by a prevalent population of pathogenic CD8+ T cells in autoimmune diabetes, PNAS, Jul. 8, 2003, vol. 100 No. 14, 8384-8388.
Lieberman S M et al., Individual Nonobese Mice Exhibit Unique Patterns of CD8+ T Cell Reactivity to Three Islet Antigens, Including the Newly Identified Widely Expressed Dystrophia Myotonica Kinase, The Journal of Immunology, 2004, 173: 6727-6734.
Serreze D V et al., MHC Class II Molecules Play a Role in the Selection of Autoreactive Class I-Restricted CD8 T Cells That Are Essential Contributors to Type 1 Diabetes Development in Nonobese Diabetic Mice, The Journal of Immunology, 2004, 172: 871-879.
Takaki T et al., Requirement for Both H-2Db and H-2Kd for the Induction of Diabetes by the Promiscuous CD8+ T Cell Clonotype AI41, The Journal of Immunology, 2004 173: 2530-2541.
PCT International Preliminary Report of Patentability dated Jul. 20, 2006 from The International Bureau of WIPO in connection with PCT International Patent Application No. PCT/US2005/026315, 5 pages.
PCT International Search Report dated Jul. 20, 2006 from the U.S. Patent Office in connection with PCT International Patent Applicaiton No. PCT/US2005/026315, 3 pages.

* cited by examiner

*Primary Examiner* — Jeffrey E Russel
(74) *Attorney, Agent, or Firm* — Amster, Rothstein & Ebenstein

(57) ABSTRACT

Provided are oligopeptide antigens to AI4-like T cells, and mouse proteins comprising those antigens. The oligopeptide antigens comprise the amino acid sequence XX(I/D/F/L)ENY(I/L)(E/W/Y)(L/M) or VMLENYTHL. Additionally provided are methods for treating a mammal having or at risk for type 1 diabetes using these antigens, or compounds which reduce or eliminate expression of these antigens. Kits comprising these antigens, and methods for determining whether a mammal is at risk for or has type 1 diabetes are also provided.

22 Claims, 12 Drawing Sheets

A

B

ANTIGENS TARGETED BY PATHOGENIC AI4 T CELLS IN TYPE 1 DIABETES AND USES THEREOF

CROSS-REFERENCE TO RELATED APPLICATION

This is a U.S. National Phase of PCT Application No. PCT/US2005/026315, filed Jul. 26, 2005, which claims the benefit of U.S. Provisional Application No. 60/592,060, filed Jul. 29, 2004.

STATEMENT OF GOVERNMENT SUPPORT

This invention was made with government support under grant numbers DK64315, DK52956, DK51090, DK46266 and DK20541 awarded by the National Institutes of Health. The government has certain rights in the invention.

The ".txt" Sequence Listing filed by EFS and which is entitled 96700_1218V3_ST25.txt, is 73 kilobytes in size and which was created on Apr. 19, 2012 is hereby incorporated by reference.

BACKGROUND (1) Field of the Invention

The present invention generally relates to diagnosis and therapy of type 1 diabetes. More specifically, the invention provides compositions and methods for diagnosis, prevention and therapy of type 1 diabetes based on the identification of islet β cell antigens targeted by pathogenic T cells.

(2) Description of the Related Art

References Cited

Altman, J. D. et al., 1996. *Science* 274: 94.

Amrani, A., J. Verdaguer, P. Serra, S. Tafuro, R. Tan, and P. Santamaria. 2000. Progression of autoimmune diabetes driven by avidity maturation of a T-cell population. *Nature* 406:739.

Amrani, A., P. Serra, J. Yamanouchi, J. D. Trudeau, R. Tan, J. F. Elliott, and P. Santamaria. 2001. Expansion of the antigenic repertoire of a single T cell receptor upon T cell activation. *J. Immunol.* 167:655-666.

Anderson, B., B. J. Park, J. Verdaguer, A. Amrani, and P. Santamaria. 1999. Prevalent CD8+ T cell response against one peptide/MHC complex in autoimmune diabetes. *Proc. Natl. Acad. Sci. U.S.A.* 96:9311.

Ascherman, D. P., T. B. Oriss, C. V. Oddis, and T. M. Wright. 2002. Critical requirement for professional APCs in eliciting T cell responses to novel fragments of histidyl-tRNA synthetase (Jo-1) in Jo-1 antibody-positive polymyositis. *J. Immunol.* 169:7127-7134.

Baekkeskov, S., H. J. Aanstoot, S. Christgau, A. Reetz, M. Solimena, M. Cascalho, F. Folli, H. Richter-Olesen, P. De Camilli, and P. D. Camilli. 1990. Identification of the 64K autoantigen in insulin-dependent diabetes as the GABA-synthesizing enzyme glutamic acid decarboxylase. *Nature* 347:151-156.

Basu, D., S. Horvath, I. Matsumoto, D. H. Fremont, and P. M. Allen. 2000. Molecular basis for recognition of an arthritic peptide and a foreign epitope on distinct MHC molecules by a single TCR. *J. Immunol.* 164:5788.

Bergman, B., and K. Haskins. 1994. Islet-specific T-cell clones from the NOD mouse respond to beta-granule antigen. *Diabetes* 43:197.

Blake, J., J. V. Johnston, K. E. Hellstrom, H. Marquardt, and L. Chen. 1996. Use of combinatorial peptide libraries to construct functional mimics of tumor epitopes recognized by MHC class I-restricted cytolytic T lymphocytes. *J. Exp. Med.* 184:121.

Borras, E., R. Martin, V. Judkowski, J. Shukaliak, Y. Zhao, V. Rubio-Godoy, D. Valmori, D. Wilson, R. Simon, R. Houghten, and C. Pinilla. 2002. Findings on T cell specificity revealed by synthetic combinatorial libraries. *J. Immunol. Methods* 267:79.

Campbell, D. J., and E. C. Butcher. 2002. Rapid acquisition of tissue-specific homing phenotypes by CD4+ T cells activated in cutaneous or mucosal lymphoid tissues. *J. Exp. Med.* 195:135-141.

Christianson, S. W., L. D. Shultz, and E. H. Leiter. 1993. Adoptive transfer of diabetes into immunodeficient NOD-scid/scid mice. Relative contributions of CD4+ and CD8+ T-cells from diabetic versus prediabetic NOD.NON-Thy-1$^a$ donors. *Diabetes* 42:44.

Christianson, S. W., D. L. Greiner, I. B. Schweitzer, B. Gott, G. L. Beamer, P. A. Schweitzer, R. M. Hesselton, and L. D. Shultz. 1996. Role of natural killer cells on engraftment of human lymphoid cells and on metastasis of human T-lymphoblastoid leukemia cells in C57BL/6J-scid mice and in C57BL/6J-scid bg mice. *Cell. Immunol.* 171:186.

Corrigall, V. M., and G. S. Panayi. 2002. Autoantigens and immune pathways in rheumatoid arthritis. *Crit. Rev. Immunol.* 22:281-293.

Cosgrove, D., D. Gray, A. Dierich, J. Kaufman, M. Lemeur, C. Benoist, and D. Mathis. 1991. Mice lacking MHC class II molecules. *Cell* 66:1051.

Cox, A. L., E. L. Huczko, V. H. Engelhard, J. Shabanowitz, and D. F. Hunt. 1997. The application of mass spectrometry to the analysis of peptides bound to MHC molecules. In *MHC: A Practical Approach*, Vol. 1. N. Fernandez, and G. Butcher, eds. Oxford University Press, Inc., New York, p. 141.

Dalakas, M. C., and R. Hohlfeld. 2003. Polymyositis and dermatomyositis. *Lancet* 362:971-982.

DiLorenzo, T. P., R. T. Graser, T. Ono, G. J. Christianson, H. D. Chapman, D. C. Roopenian, S. G. Nathenson, and D. V. Serreze. 1998. Major histocompatibility complex class I-restricted T cells are required for all but the end stages of diabetes development in nonobese diabetic mice and use a prevalent T cell receptor a chain gene rearrangement. *Proc. Natl. Acad. Sci. U.S.A.* 95:12538.

DiLorenzo, T. P., S. M. Lieberman, T. Takaki, S. Honda, H. D. Chapman, P. Santamaria, D. V. Serreze, and S. G. Nathenson. 2002. During the early prediabetic period in NOD mice, the pathogenic CD8+ T-cell population comprises multiple antigenic specificities. *Clin. Immunol.* 105:332.

Falk, K., O. Rotzschke, S. Stevanovic, G. Jung, and H. G. Rammensee. 1991. Allele-specific motifs revealed by sequencing of self-peptides eluted from MHC molecules. *Nature* 351:290.

Fleischhauer, K., S. Tanzarella, H. J. Wallny, C. Bordignon, and C. Traversari. 1996. Multiple HLA-A alleles can present an immunodominant peptide of the human melanoma antigen Melan-A/MART-1 to a peptide-specific HLA-A*0201+ cytotoxic T cell line. *J. Immunol.* 157:787.

Gammon et al., 1986. *Nature* (London) 319, 413.

Graser, R. T., C. E. Mathews, E. H. Leiter, and D. V. Serreze. 1999. MHC characterization of ALR and ALS mice: respective similarities to the NOD and NON strains. *Immunogenetics* 49:722.

Graser, R. T., T. P. DiLorenzo, F. Wang, G. J. Christianson, H. D. Chapman, D. C. Roopenian, S. G. Nathenson, and D. V. Serreze. 2000. Identification of a CD8 T cell that can independently mediate autoimmune diabetes development in the complete absence of CD4 T cell helper functions. *J. Immunol.* 164:3913.

Groenen, P., and B. Wieringa. 1998. Expanding complexity in myotonic dystrophy. *BioEssays* 20:901-912.

Groenen, P. J., D. G. Wansink, M. Coerwinkel, W. van den Broek, G. Jansen, and B. Wieringa. 2000. Constitutive and regulated modes of splicing produce six major myotonic dystrophy protein kinase (DMPK) isoforms with distinct properties. *Hum. Mol. Genet.* 9:605-616.

Gurlo, T., K Kawamura, and H. von Grafenstein. 1999. Role of inflammatory infiltrate in activation and effector function of cloned islet reactive nonobese diabetic $CD8^+$ T cells: involvement of a nitric oxide-dependent pathway. *J. Immunol.* 163:5770-5780.

Hamaguchi, K., H. R Gaskins, and E. H. Leiter. 1991. NIT-1, a pancreatic β-cell line established from a transgenic NOD/Lt mouse. *Diabetes* 40:842.

Hartemann, A. H. et al. 1999. *Clin, Exper. Immunol.* 116, 225.

Heath, W. R., C. Kurts, J. F. Miller, and F. R. Carbone. 1998. Cross-tolerance: a pathway for inducing tolerance to peripheral tissue antigens. *J. Exp. Med.* 187:1549-1553.

Hemmer, B., M. Vergelli C. Pinilla, R. Houghten, and R. Martin. 1998. Probing degeneracy in T-cell recognition using peptide combinatorial libraries. *Immunol. Today* 19:163.

Hoglund, P., J. Mintem, C. Waltzinger, W. Heath, C. Benoist, and D. Mathis. 1999. Initiation of autoimmune diabetes by developmentally regulated presentation of islet cell antigens in the pancreatic lymph nodes. *J. Exp. Med.* 189:331-339.

Hugues, S., E. Mougneau, W. Ferlin, D. Jeske, P. Hofman, D. Homann, L. Beaudoin, C. Schrike, M. Von Herrath, A. Lehuen, and N. Glaichenhaus. 2002. Tolerance to islet antigens and prevention from diabetes induced by limited apoptosis of pancreatic β cells. *Immunity* 16:169-181.

Ishibashi, H., M. Nakamura, S. Shimoda, and M. E. Gershwin. 2003. T cell immunity and primary biliary cirrhosis. *Autoimmun. Rev.* 2:19-24.

Jameson, S. C. 2002. Maintaining the norm: T-cell homeostasis. *Nat. Rev. Immunol.* 2:547.

Jansen, G., M. Mahadevan, C. Amemiya, N. Wormsskamp, B. Segers, W. Hendriks, K. O'Hoy, S. Baird, L. Sabourin, G. Lennon, P. L. Jap, D. Iles, M. Coerwinkel, M. Hofker, A. V. Carrano, P. J. de Jong, R. G. Korneluk, and B. Wieringa. 1992. Characterization of the myotonic dystrophy region predicts multiple protein isoform-encoding mRNAs. *Nat. Genet.* 1:261-266.

Jin, S., M. Shimizu, A. Balasubramanyam, and H. F. Epstein. 2000. Myotonic dystrophy protein kinase (DMPK) induces actin cytoskeletal reorganization and apoptotic-like blebbing in lens cells. *Cell Motil. Cytoskeleton* 45:133-148.

Kalyuzhny, A., and S. Stark. 2001. A simple method to reduce the background and improve well-to-well reproducibility of staining in ELISPOT assays. *J. Immunol. Methods* 257:93-97.

Karre, K., H. G. Ljunggren, G. Piontek, and R. Kiessling. 1986. Selective rejection of H-2-deficient lymphoma variants suggests alternative immune defence strategy. *Nature* 319:675.

Karttunen, J., S. Sanderson, and N. Shastri. 1992. Detection of rare antigen-presenting cells by the lacZ T-cell activation assay suggests an expression cloning strategy for T-cell antigens. *Proc. Natl. Acad. Sci. U.S.A.* 89:6020-6024.

Kurts, C., R. M. Sutherland, G. Davey, M. Li, A. M. Lew, E. Blanas, F. R. Carbone, J. F. Miller, and W. R. Heath. 1999. CD8 T cell ignorance or tolerance to islet antigens depends on antigen dose. *Proc. Natl. Acad. Sci. U.S.A.* 96:12703-12707.

Lang, H. L., H. Jacobsen, S. Ikemizu, C. Andersson, K. Harlos, L. Madsen, P. Hjorth, L. Sondergaard, A. Svejgaard, K. Wucherpfennig, D. I. Stuart, J. I. Bell, E. Y. Jones, and L. Fugger. 2002. A functional and structural basis for TCR cross-reactivity in multiple sclerosis. *Nat. Immunol.* 3:940.

Leiter, E. H. 1997. The NOD mouse: A model for insulin-dependent diabetes mellitus. In *Current Protocols in Immunology.* J. E. Coligan, A. M. Kruisbeek, D. H. Margulies, E. M. Shevach, and W. Strober, eds. John Wiley & Sons, Inc., Hoboken, p. 15.9.1.

Leung, T., X. Q. Chen, I. Tan, E. Manser, and L. Lim. 1998. Myotonic dystrophy kinase-related Cdc42-binding kinase acts as a Cdc42 effector in promoting cytoskeletal reorganization. *Mol. Cell. Biol.* 18:130-140.

Lieberman, S. M., and T. P. DiLorenzo. 2003. A comprehensive guide to antibody and T-cell responses in type 1 diabetes. *Tissue Antigens* 62:359.

Lieberman, S. M., A. M. Evans, B. Han, T. Takaki, Y. Vinnitskaya, J. A. Caldwell, D. V. Serreze, J. Shabanowitz, D. F. Hunt, S. G. Nathenson, P. Santamaria, and T. P. DiLorenzo. 2003. Identification of the β cell antigen targeted by a prevalent population of pathogenic $CD8^+$ T cells in autoimmune diabetes. *Proc. Natl. Acad. Sci. U.S.A.* 100:8384.

Liblau, R. S., F. S. Wong, L. T. Mars, and P. Santamaria. 2002. Autoreactive CD8 T cells in organ-specific autoimmunity: emerging targets for therapeutic intervention. *Immunity* 17:1.

Lindahi, K. F., and D. B. Wilson. 1977a. Histocompatibility antigen-activated cytotoxic T lymphocytes. L. Estimates of the absolute frequency of killer cells generated in vitro. *J. Exp. Med.* 145:500.

Lindahl, K. F., and D. B. Wilson. 1977b. Histocompatibility antigen-activated cytotoxic T lymphocytes. II. Estimates of the frequency and specificity of precursors. *J. Exp. Med.* 145:508.

Mandik-Nayak, L., B. T. Wipke, F. F. Shih, E. R. Unanue, and P. M. Allen. 2002. Despite ubiquitous autoantigen expression, arthritogenic autoantibody response initiates in the local lymph node. *Proc. Natl. Acad. Sci. U.S.A.* 59:14368-14373.

Martinez, N. R., P. Augstein, A. K. Moustakas, G. K. Papadopoulos, S. Gregori, L. Adorini, D. C. Jackson, and L. C. Harrison. 2003. Disabling an integral CTL epitope allows suppression of autoimmune diabetes by intranasal proinsulin peptide. *J. Clin. Invest.* 111:1365.

Matsumoto, I., A. Staub, C. Benoist, and D. Mathis. 1999. Arthritis provoked by linked T and B cell recognition of a glycolytic enzyme. *Science* 286:1732-1735.

Moncrieff, C. L., M. E. Bailey, N. Morrison, and K. J. Johnson. 1999. Cloning and chromosomal localization of human Cdc42-binding protein kinase β. *Genomics* 57:297-300.

Morgan, D. J., C. T. Nugent, B. J. Raveney, and L. A. Sherman. 2004. In a transgenic model of spontaneous autoimmune diabetes, expression of a protective class II MHC molecule results in thymic deletion of diabetogenic $CD8^+$ T cells. *J. Immunol.* 172:1000.

Nagata, M., P. Santamaria, T. Kawamura, T. Utsugi, and J. W. Yoon. 1994. Evidence for the role of $CD8^+$ cytotoxic T cells in the destruction of pancreatic β-cells in nonobese diabetic mice. *J. Immunol.* 152:2042-2050.

O'Dwyer, D. T., A. I. Smith, M. L. Matthew, N. M. Andronicos, M. Ranson, P. J. Robinson, and P. A. Crock. 2002. Identification of the 49-kDa autoantigen associated with lymphocytic hypophysitis as α-enolase. *J. Clin. Enidocrinol. Metab.* 87:752-757.

Oldstone, M. B., A. Tishon, R. Geckeler, H. Lewicki, and J. L. Whitton. 1992. A common antiviral cytotoxic T-lymphocyte epitope for diverse major histocompatibility complex haplotypes: implications for vaccination. *Proc. Nat. Acad. Sci. U.S.A.* 89:2752.

Ostrov, D. A., M. M. Roden, W. Shi, E. Palmieri, G. J. Christianson, L. Mendoza, G. Villaflor, D. Tilley, N. Shastri, H. Grey, S. C. Almo, D. Roopenian, and S. G. Nathenson. 2002. How H13 histocompatibility peptides differing by a single methyl group and lacking conventional MHC binding anchor motifs determine self-nonself discrimination. *J. Immunol.* 168:283.

Pall, G. S., K. J. Johnson, and G. L. Smith. 2003. Abnormal contractile activity and calcium cycling in cardiac myocytes isolated from DMPK knockout mice. *Physiol. Genomics* 13:139-146.

Prochazka, M., D. V. Serreze, S. M. Worthen, and E. H. Leiter. 1989. Genetic control of diabetogenesis in NOD/Lt mice. Development and analysis of congenic stocks. *Diabetes* 38:1446.

Quinn, A., M. F. McInerney, and E. E. Sercarz. 2001. MHC class I-restricted determinants on the glutamic acid decarboxylase 65 molecule induce spontaneous CTL activity. *J. Immunol.* 167:1748.

Reddy, S., D. J. Mistry, Q. C. Wang, L. M. Geddis, H. C. Kutchai, J. R. Moorman, and J. P. Mounsey. 2002. Effects of age and gene dose on skeletal muscle sodium channel gating in mice deficient in myotonic dystrophy protein kinase. *Muscle Nerve* 25:850-857.

Roep, B. O. 2003. The role of T-cells in the pathogenesis of Type 1 diabetes: from cause to cure. *Diabetologia* 46:305-321.

Salomon, B., L. Rhee, H. Bour-Jordan, H. Hsin, A. Montag, B. Soliven, J. Arcella, A. M. Girvin, J. Padilla, S. D. Miller, and J. A. Bluestone. 2001. Development of spontaneous autoimmune peripheral polyneuropathy in B7-2-deficient NOD mice. *J. Exp. Med.* 194:677-684.

Salter, R. D., D. N. Howell, and P. Cresswell. 1985. Genes regulating HLA class I antigen expression in T-B lymphoblast hybrids. *Immunogenetics* 21:235.

Santamaria, P., T. Utsugi, B. J. Park, N. Averill, S. Kawazu, and J. W. Yoon. 1995. Beta-cell-cytotoxic $CD8^+$ T cells from nonobese diabetic mice use highly homologous T cell receptor α-chain CDR3 sequences. *J. Immunol.* 154:2494-2503.

Saravia-Fernandez, F., C. Faveeuw, C. Blasquez-Bulant, M. Tappaz, M. Throsby, G. Pelletier, H. Vaudry, M. Dardenne, and F. Homo-Delarche. 1996. Localization of γ-aminobutyric acid and glutamic acid decarboxylase in the pancreas of the nonobese diabetic mouse. *Endocrinology* 137:3497-3506.

Schaller, M., D. R. Burton, and H. J. Ditzel. 2001. Autoantibodies to GPI in rheumatoid arthritis: linkage between an animal model and human disease. *Nat. Immunol.* 2:746-753.

Schulz, P. E., A. D. McIntosh, M. R. Kasten, B. Wieringa, and H. F. Epstein. 2003. A role for myotonic dystrophy protein kinase in synaptic plasticity. *J. Neurophysiol.* 89:1177-1186.

Serreze, D. V., and E. H. Leiter. 1991. Development of diabetogenic T cells from NOD/Lt marrow is blocked when an allo-H-2 haplotype is expressed on cells of hemopoietic origin, but not on thymic epithelium. *J. Immunol.* 147:1222.

Serreze, D. V., and E. H. Leiter. 2001a. Genes and pathways underlying autoimmune diabetes in NOD mice. In *Molecular Pathology of Insulin Dependent Diabetes Mellitus*. M. G. von Herrath, ed. Karger Press, New York, p. 31.

Serreze, D. V., and E. H. Leiter. 2001b. Genes and cellular requirements for autoimmune diabetes susceptibility in nonobese diabetic mice. *Curr. Dir. Autoimmun.* 4:31-67.

Serreze, D. V., E. H. Leiter, G. J. Christianson, D. Greiner, and D. C. Roopenian. 1994. Major histocompatibility complex class I-deficient $NOD-B2m^{null}$ mice are diabetes and insulitis resistant. *Diabetes* 43:505.

Serreze, D. V., E. H. Leiter, M. S. Hanson, S. W. Christianson, L. D. Shultz, R. M. Hesselton, and D. L. Greiner. 1995. $Eniv30^{null}$ NOD-scid mice. An improved host for adoptive transfer of autoimmune diabetes and growth of human lymphohematopoietic cells. *Diabetes* 44:1392.

Serreze, D. V., M. A. Pierce, C. M. Post, H. D. Chapman, H. Savage, R. T. Bronson, P. B. Rothman, and G. A. Cox. 2003. Paralytic autoimmune myositis develops in nonobese diabetic mice made Th1 cytokine-deficient by expression of an IFN-γ receptor β-chain transgene. *J. Immunol.* 170:2742-2749

Serreze, D. V., T. M. Holl, M. P. Marron, R. T. Graser, E. A. Johnson, C. Choisy-Rossi, R. M. Slattery, S. M. Lieberman, and T. P. DiLorenzo. 2004. MHC class II molecules play a role in the selection of autoreactive class I-restricted CD8 T cells that are essential contributors to type 1 diabetes development in nonobese diabetic mice. *J. Immunol.* 172:871.

Shimizu, J., O. Kanagawa, and E. R. Unanue. 1993. Presentation of β-cell antigens to $CD4^+$ and $CD8^+$ T cells of non-obese diabetic mice. *J. Immunol.* 151:1723-1730.

Shirai, M., M. S. Vacchio, R. J. Hodes, and J. A. Berzofsky. 1993. Preferential Vβ usage by cytotoxic T cells cross-reactive between two epitopes of HIV-1 gp160 and degenerate in class I MHC restriction. *J. Immunol.* 151:2283.

Shultz, L. D., P. A. Schweitzer, E. J. Hall, J. P. Sundberg, S. Taylor, and P. D. Walzer. 1989. *Pneumocystis carinii* pneumonia in scid/scid mice. *Curr. Top. Microbiol. Immunol.* 152:243.

Skinner, M. A., and J. Marbrook. 1976. An estimation of the frequency of precursor cells which generate cytotoxic lymphocytes. *J. Exp. Med.* 143:1562.

Sparbier, K., and P. Walden. 1999. T cell receptor specificity and mimotopes. *Curr. Opin. Immunol.* 11:214.

Starr, T. K., S. C. Jameson, and K. A. Hogquist. 2003. Positive and negative selection of T cells. *Annu. Rev. Immunol.* 21:139.

Takaki, T., S. M. Lieberman, T. M. Holl, B. Han, P. Santamaria, D. V. Serreze, and T. P. DiLorenzo. 2004. Requirement for both $H-2D^b$ and $H-2K^d$ for the induction of diabetes by the promiscuous $CD8^+$ T cell clonotype AI4. *J. Immunol.* 173:2530 (Published Jul. 30, 2004; also provided herewith as Example 1).

Tallquist, M. D., and L. R. Pease. 1995. Alloreactive 2C T cells recognize a self peptide in the context of the mutant $K^{bm3}$ molecule. *J. Immunol.* 155:2419.

Threlkeld, S. C., P. A. Wentworth, S. A. Kalams, B. M. Wilkes, D. J. Ruhl, E. Keogh, J. Sidney, S. Southwood, B. D. Walker, and A. Sette. 1997. Degenerate and promiscuous recognition by CTL of peptides presented by the MHC class I A3-like superfamily: implications for vaccine development. *J. Immunol.* 159:1648.

Trudeau, J. D., J. P. Dutz, E. Arany, D. J. Hill, W. E. Fieldus, and D. T. Finegood. 2000. Neonatal β-cell apoptosis: a trigger for autoimmune diabetes? *Diabetes* 49:1-7.

Trudeau, J. D., C. Kelly-Smith, C. B. Verchere, J. F. Elliott, J. P. Dutz, D. T. Finegood, P. Santamaria, and R. Tan. 2003. Prediction of spontaneous autoimmune diabetes in NOD mice by quantification of autoreactive T cells in peripheral blood. *J. Clin. Invest.* 111:217.

Turley, S., L. Poirot, M. Hattori, C. Benoist, and D. Mathis. 2003. Physiological β cell death triggers priming of self-reactive T cells by dendritic cells in a type-1 diabetes model. *J. Exp. Med.* 198:1527-1537.

Ueno, T., H. Tomiyama, and M. Takiguchi. 2002. Single T cell receptor-mediated recognition of an identical HIV-derived peptide presented by multiple HLA class I molecules. *J. Immunol.* 169:4961.

Utsugi, T., J. W. Yoon, B. J. Park, M. Imamura, N. Averill, S. Kawazu, and P. Santamaria. 1996. Major histocompatibility complex class I-restricted infiltration and destruction of pancreatic islets by NOD mouse-derived β-cell cytotoxic CD8$^+$ T-cell clones in vivo. *Diabetes* 45:1121-1131.

Valmori, D., A. Sabbatini, A. Lanzavecchia, G. Corradin, and P. M. Matricardi. 1994. Functional analysis of two tetanus toxin universal T cell epitopes in their interaction with DR1101 and DR1104 alleles. *J. Immunol.* 152:2921.

Verdaguer, J., D. Schmidt, A. Amrani, B. Anderson, N. Averill, and P. Santamaria. 1997. Spontaneous autoimmune diabetes in monoclonal T cell nonobese diabetic mice. *J. Exp. Med.* 186:1663.

Wang, B., A. Gonzalez, C. Benoist, and D. Mathis. 1996. The role of CD8$^+$ T cells in the initiation of insulin-dependent diabetes mellitus. *Eur. J. Immunol.* 26:1762-1769.

Wansink, D. G., R. E. van Herpen, M. M. Coerwinkel-Driessen, P. J. Groenen, B. A. Hemmings, and B. Wieringa. 2003. Alternative splicing controls myotonic dystrophy protein kinase structure, enzymatic activity, and subcellular localization. *Mol. Cell. Biol.* 23:5489-5501.

Wicker, L. S., M. C. Appel, F. Dotta, A. Pressey, B. J. Miller, N. H. DeLarato, P. A. Fischer, R. C. Boltz, Jr., and L. B. Peterson. 1992. Autoimmune syndromes in major histocompatibility complex (MHC) congenic strains of nonobese diabetic (NOD) mice. The NOD MHC is dominant for insulitis and cyclophosphamide-induced diabetes. *J. Exp. Med.* 176:67.

Wicker, L. S., E. H. Leiter, J. A. Todd, R. J. Renjilian, E. Peterson, P. A. Fischer, P. L. Podolin, M. Zijlstra, R. Jaenisch, and L. B. Peterson. 1994. β$_2$-microglobulin-deficient NOD mice do not develop insulitis or diabetes. *Diabetes* 43:500.

Winer, S., H. Tsui, A. Lau, A. Song, X. Li, R. K. Cheung, A. Sampson, F. Afifiyan, A. Elford, G. Jackowski, D. J. Becker, P. Santamaria, P. Ohashi, and H. M. Dosch. 2003. Autoimmune islet destruction in spontaneous type 1 diabetes is not β-cell exclusive. *Nat. Med.* 9:198-205.

Wong, F. S., I. Visintin, L. Wen, R. A. Flavell, and C. A. Janeway, Jr. 1996. CD8 T cell clones from young nonobese diabetic (NOD) islets can transfer rapid onset of diabetes in NOD mice in the absence of CD4 cells. *J. Exp. Med.* 183:67.

Wong, F. S., J. Karttunen, C. Dumont, L. Wen, I. Visintin, I. M. Pilip, N. Shastri, E. G. Pamer, and C. A. Janeway, Jr. 1999. Identification of an MHC class I-restricted autoantigen in type 1 diabetes by screening an organ-specific cDNA library. *Nat Med.* 5:1026.

Wong, F. S., A. K. Moustakas, L. Wen, G. K. Papadopoulos, and C. A. Janeway, Jr. 2002. Analysis of structure and function relationships of an autoantigenic peptide of insulin bound to H-2K$^d$ that stimulates CD8 T cells in insulin-dependent diabetes mellitus. *Proc. Natl. Acad. Sci. U.S.A.* 99:5551

Yamanouchi, J., J. Verdaguer, B. Han, A. Amrani, P. Serra, and P. Santamaria. 2003. Cross-priming of diabetogenic T cells dissociated from CTL-induced shedding of β cell autoantigens. *J. Immunol.* 171:6900-6909.

Yeaman, S. J., J. A. Kirby, and D. E. Jones. 2000. Autoreactive responses to pyruvate dehydrogenase complex in the pathogenesis of primary biliary cirrhosis. *Immunol. Rev.* 174:238-249.

Young, A. C., W. Zhang, J. C. Sacchettini, and S. G. Nathenson. 1994. The three-dimensional structure of H-2D$^b$ at 2.4 Å resolution: implications for antigen-determinant selection. *Cell* 76:39.

Yui, M. A., K. Muralidharan, B. Moreno-Altamirano, G. Perrin, K. Chestnut, and E. K. Wakeland. 1996. Production of congenic mouse strains carrying NOD-derived diabetogenic genetic intervals: an approach for the genetic dissection of complex traits. *Mamm. Genome* 7:331.

Zhang, Y., B. O'Brien, J. Trudeau, R. Tan, P. Santamaria, and J. P. Dutz. 2002. In situ β cell death promotes priming of diabetogenic CD8 T lymphocytes. *J. Immunol.* 168:1466-1472.

Zuberi, A. R., G. J. Christianson, L. M. Mendoza, N. Shastri, and D. C. Roopenian. 1998. Positional cloning and molecular characterization of an immunodominant cytotoxic determinant of the mouse H3 minor histocompatibility complex. *Immunity* 9:687.

In both humans and NOD mice, type 1 diabetes (T1D) is an autoimmune disease that results from T cell-mediated destruction of insulin-producing pancreatic β cells and involves complex interactions among developmental, genetic, and environmental factors (Serreze and Leiter, 2001a; 2001b; Roep, 2003). In the NOD mouse model, spontaneous autoimmune diabetes development requires both CD4$^+$ and CD8$^+$ T cells (Christianson et al., 1993; Serreze et al., 1994; Wicker et al., 1994; Wang et al., 1996; DiLorenzo et al., 1998), with evidence suggesting that CD8$^+$ T cells are required for the initial stages of β cell destruction (Wang et al., 1996; DiLorenzo et al., 1998). Although there are multiple susceptibility loci, the strong association of particular MHC class II molecules with disease has led to extensive investigation of CD4$^+$ T cells in T1D (Lieberman and DiLorenzo, 2003). However, several studies in NOD mice have documented the importance of pathogenic CD8$^+$ T cells in the initial stages of β cell destruction (DiLorenzo et al., 1998, Serreze et al., 1994; Wong et al., 1996; Wicker et al., 1994).

Several NOD-derived, β cell-autoreactive CD8$^+$ T cell clones have been reported (DiLorenzo et al., 1998; 2002; Gurlo et al., 1999; Nagata et al., 1994; Wong et al., 1996; Shimizu et al., 1993); however, only three of these (designated G9C8, 8.3, and AI4) have demonstrated in vivo pathogenicity.

The 8.3 clone represents a prevalent population of islet-specific glucose-6-phosphatase catalytic subunit-related protein$_{206-214}$ (IGRP$_{206-214}$)-reactive T cells present in NOD islets throughout disease development and progression to overt diabetes (DiLorenzo et al., 1998; Santamaria et al., 1995; Lieberman et al., 2003; Amrani et al., 2000; Trudeau et al., 2003). The pathogenicity of 8.3 is demonstrated by the accelerated rate of diabetes development observed in 8.3 TCR transgenic NOD mice that is enhanced by CD4$^+$ T cell help (Verdaguer et al., 1997), and by adoptive transfer studies (Nagata et al., 1994; Utsugi et al., 1996).

The insulin B$_{15-23}$-reactive pathogenic CD8$^+$ T cell clone G9C8 has been shown to cause diabetes in the absence of CD4+ T cell help, but these experiments involved transfer of previously activated G9C8 T cells into recipient mice; thus, their ability to develop and mature in the absence of CD4+ T cell help is unknown (Wong et al., 1996; 1999).

Both the 8.3 clone and the G9C8 clone are H-2K$^d$-restricted (Wong et al., 1999; Lieberman et al., 2003).

The AI4 CD8+ T cell clone, originally isolated from the islets of a 5-week-old female NOD mouse (DiLorenzo et al., 1998), represents one of these β cell-autoreactive specificities. NOD mice transgenically expressing the AI4 TCR (designated NOD.AI4αβ Tg) progress to overt diabetes significantly earlier than nontransgenic NOD mice (Graser et al., 2000). Strikingly, this accelerated diabetes development is also observed in NOD-scid.AI4αβ Tg, NOD.CD4$^{null}$.AI4αβ Tg (Graser et al., 2000), and NOD.Rag1$^{null}$.AI4αβ Tg mice (DiLorenzo et al., 2002), all of which lack CD4+ T cells. Hence, naïve AI4 T cells are able to develop, mature, and mediate sufficient β cell destruction to cause accelerated disease in the complete absence of CD4+ T cell help. AI4 represents the only diabetogenic CD8+ T cell clone known to be capable of doing so.

We recently showed that AI4 recognizes a β cell peptide (still unidentified) that is distinct from these two (DiLorenzo et al., 2002). Thus, AI4 represents a third antigenic specificity contributing to early β cell destruction in NOD mice. However, to date, only mimotope ligands for AI4 have been identified (Serreze et al., 2004).

There is thus a need to characterize the AI4 clone, by identifying mimotopes capable of activating AI4-like T cells and allowing β cell destruction, and by identifying the β cell antigen having that binding specificity.

SUMMARY OF THE INVENTION

Accordingly, the inventors have identified β cell antigens to the AI4 clone, and have demonstrated its importance in type 1 diabetes. See Examples.

Thus, in some embodiments, the invention is directed to isolated and purified oligopeptides or polypeptides comprising a sequence of less than 552 amino acids. These peptides comprise an amino acid sequence selected from the group consisting of XX(I/D/F/L)ENY(I/L)(E/W/Y)(L/M) (SEQ ID NO:16) and VMLENYTHL (SEQ ID NO:12). In these embodiments, if the sequence is VMLENYTHL (SEQ ID NO:12), then the oligopeptide or polypeptide is less than 51 amino acids.

In other embodiments, the invention is directed to isolated and purified oligopeptides 9-10 amino acids in length, completely homologous with a mammalian DMK, MRCKβ, TrEMBL accession Q8C1H3 or a mammalian analog thereof, Swiss-Prot accession Q9D4H1 or a mammalian analog thereof, or TrEMBL accession P97871 or a mammalian analog thereof. In these embodiments, the oligopeptides have at least 90% homology to at least one of SEQ ID NO:1, SEQ ID NO:2, SEQ ID NO:3, SEQ ID NO:4, SEQ ID NO:5, SEQ ID NO:6 or SEQ ID NO:7. The oligopeptides of these embodiments are capable of binding an MHC class I molecule of the mammal.

The present invention is also directed to kits comprising a sterile preparation comprising the above-described oligopeptides, in a container.

Additionally, the invention is directed to antisense molecules, ribozymes, and RNAi molecules complementary to at least a portion of a mammalian mRNA encoding a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof. In these embodiments, the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof is at least 90% homologous to at least one of SEQ ID NO:1, SEQ ID NO:2, SEQ ID NO:3, SEQ ID NO:4, SEQ ID NO:5, SEQ ID NO:6, or SEQ ID NO:7. These antisense molecules, ribozymes, and RNAi molecules are capable of inhibiting translation of the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof.

In additional embodiments, the invention is directed to cDNAs having the nucleotide sequence of SEQ ID NO:8 or SEQ ID NO:15, vectors comprising those cDNAs, and cells transfected with those vectors.

The invention is also directed to mammalian pancreatic islet β cells comprising any of the antisense molecules, ribozymes, or RNAi molecules described above.

In further embodiments, the invention is directed to methods of treating a mammal that is at risk for or has type 1 diabetes. The methods comprise administering an oligopeptide to the mammal in a manner sufficient to reduce CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal. In these embodiments, the oligopeptide is 9-10 amino acids in length, and comprises the amino acid sequence XX(I/D/F/L)ENY(I/L)(E/W/Y)(L/M) (SEQ ID NO:16) or VMLENYTHL (SEQ ID NO:12).

The invention is additionally directed to methods of treating a mammal that is at risk for or has type 1 diabetes. The methods comprise administering the above-described oligopeptide to the mammal in a manner sufficient to reduce CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal.

In additional embodiments, the invention is directed to methods of treating a mammal that is at risk for or has type 1 diabetes. The methods comprise administering an oligopeptide 9-10 amino acids in length to the mammal, where the oligopeptide is a medium- or low-affinity ligand to an AI4-like T cell, and the oligopeptide is homologous to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal.

The invention is further directed to methods of preventing a CD8+ T cell that is cytotoxic to pancreatic islet β cells from killing a β cell. The methods comprise treating the β cell with a compound capable of specifically binding the above-described oligopeptide.

In further embodiments, the invention is directed to methods of preventing CD8+ T cells that are cytotoxic to pancreatic islet β cells from killing a mammalian β cell. The methods comprise treating the CD8+ T cells with an oligopeptide 9-10 amino acids in length in a manner sufficient to reduce CD8+ T cells reactive to the mammalian βcell. In these embodiments, the oligopeptide comprises an amino acid sequence selected from the group consisting of XX(I/D/F/L)ENY(I/L)(E/W/Y)(L/M) (SEQ ID NO:16) and VMLENYTHL (SEQ ID NO:12).

Additionally, the invention is directed to methods of treating a mammal that is at risk for or has type 1 diabetes. The method comprises administering to the mammal the above-described antisense molecule, ribozyme, or RNAi molecule, where the antisense molecule, ribozyme, or RNAi molecule is administered in a manner sufficient to decrease expression of a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal.

In additional embodiments, the invention is directed to methods of treating a mammal having type 1 diabetes. The methods comprise transplanting a pancreatic islet β cell into the pancreas of the mammal, where the β cell is transfected with a vector that expresses an antisense molecule, a ribozyme, or an RNAi molecule that is capable of specifically inhibiting translation of a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal.

The invention is further directed to methods for determining whether a mammal is at risk for or has type 1 diabetes. The methods comprise determining the presence of CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal by a. obtaining a sample of lymphocytes comprising CD8+ T cells from the mammal;

b. combining the lymphocytes with an oligopeptide and an MHC class I molecule that is capable of binding the oligopeptide, where the oligopeptide or the MHC molecule further comprises a detectable label and where the oligopeptide is 9-10 amino acids in length and comprises an amino acid sequence selected from the group consisting of XX(I/D/F/L)ENY(I/L)(E/W/Y)(L/M) (SEQ ID NO:16) and VMLENYTHL (SEQ ID NO:12); and c. determining whether any CD8+ T cells specifically bind to the oligopeptide. In these embodiments, CD8+ T cell binding to the oligopeptide indicates that the mammal is at risk for or has type 1 diabetes.

In further embodiments, the invention is directed to methods for determining whether a mammal is at risk for or has type 1 diabetes. The methods comprise determining the presence of CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal by a. obtaining a sample of lymphocytes comprising CD8+ T cells from the mammal;

b. combining the lymphocytes with an oligopeptide and an MHC class I molecule that is capable of binding the oligopeptide, where the oligopeptide or the MHC molecule further comprises a detectable label and wherein the oligopeptide is 9-10 amino acids and is completely homologous with a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal; and c. determining whether any CD8+ T cells specifically bind to the oligopeptide. In these embodiments, CD8+ T cell binding to the oligopeptide indicates that the mammal is at risk for or has type 1 diabetes.

DETAILED DESCRIPTION OF THE INVENTION

Figure 1:
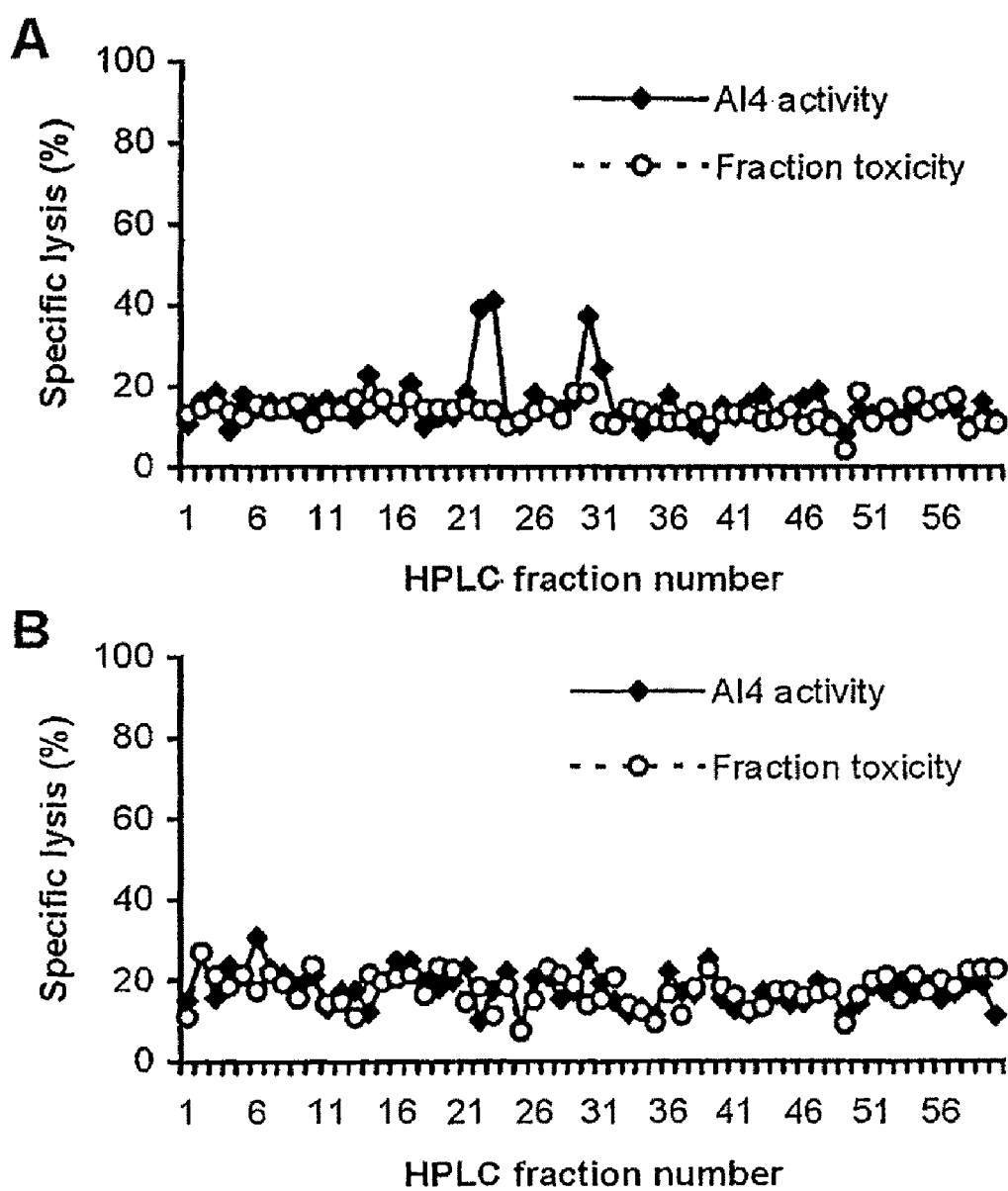
FIG. 1 is graphs of experimental results demonstrating that AI4 recognizes a NIT-1β cell peptide in the context of H-2D$^b$. The graphs show AI4 cytotoxic activity towards (A) RMA-S target cells pulsed with HPLC fractions of β cell peptides eluted from H-2D$^b$ or (B) RMA-S/K$^d$ target cells pulsed with HPLC fractions of β cell peptides eluted from H-2K$^d$. Class I MHC molecules were separately immunoaffinity purified from IFN-γ-treated NIT-1β cells. MHC class I-bound peptides were eluted, fractionated by reverse-phase HPLC, and 1.6×10$^9$ NIT-1 cell equivalents of peptide were tested for epitope reconstitution activity by $^{51}$Cr-release cytotoxicity assay at an E:T ratio of 40. Fraction toxicity was determined by incubating HPLC peptide fraction-pulsed target cells in the absence of AI4 T cells. AI4-mediated lysis of non-peptide-pulsed target cells was 4.2% (RMA-S) and 8.5% (RMA-S/K$^d$).

The present invention is based on the identification of several mouse antigens that are recognized by AI4-like T cells. The identification of these antigens are disclosed in Example 2 (see Table 2 in particular). These antigens are present on:

dystrophia myotonica kinase (DMK), having the AI4 peptide antigen with the amino acid sequence FQDENYLYL ("FNL9") (SEQ ID NO:9) using the commonly accepted single letter amino acid abbreviations;

myotonic dystrophy kinase-related Cdc42-binding protein kinase β (MRCKβ), having the same peptide antigen as DMK (SEQ ID NO:9);

exocyst complex component Sec5, published as Swiss-Prot accession Q9D4H1, having antigen amino acid sequence RLFENYIEL ("RIL9") (SEQ ID NO:10);

aquarius, published as TrEMBL accession P97871, having antigen amino acid sequence QYLENYLWM ("QM9") (SEQ ID NO:11); and similar to KRAB zinc finger protein, published as TrEMBL accession Q8C1H3, having antigen amino acid sequence VMLENYTEL ("VML9") (SEQ ID NO:12).

Additionally, two artificial AI4 mimotopes are described, YFIENYLEL ("Mim") (SEQ ID NO:14), and YAENYLEL ("MimA2")(SEQ ID NO:13). The latter sequence (MimA2) elicits the strongest AI4 CTL response of all of the peptides.

Both DMK and MRCKβ are expressed in islets, and cells transfected with DMK are capable of inducing an AI4 CTL response (Example 2).

As used herein, an amino acid sequence of a DMK, an MRCKβ, a Swiss-Prot accession Q9D4H1 or mammalian analog thereof, a TrEMBL accession P97871 or mammalian analog thereof, or a TrEMBL accession Q8C1H3 or mammalian analog thereof includes any naturally occurring mammalian amino acid sequence that is at least 90% identical to SEQ ID NO:1 or SEQ ID NO:2 (NOD or human DMK amino acid sequence, respectively), SEQ ID NO:3 or SEQ ID NO:4 (NOD or human MRCKβ amino acid sequence, respectively), SEQ ID NO:6 (Swiss-Prot accession Q9D4H1), SEQ ID NO:7 (TrEMBL accession P97871), or SEQ ID NO:5 (TrEMBL accession Q8C1H3), respectively. The identification of any such mammalian amino acid sequence can be readily made without undue experimentation, e.g., by identifying mRNA sequences that are highly (i.e., >90%) homologous to already-identified mRNA sequences and determining the amino acid sequence of the expressed protein.

Taking all of the above AI4-reacting amino acid sequences, as well as similar but nonreacting sequences described in Example 2 (HL9, FSL9, TL9, EL9, RLL9, DM9 and VTL9—see Table 2), we have deduced that AI4 CTL cells are likely to react with oligopeptides having the sequence XX(I/D/F/L)ENY(I/L)(E/W/Y)(L/M) (SEQ ID NO:16) or VMLENYTHL (SEQ ID NO:12), where X is any amino acid, and slashes separate alternative amino acids for a given position.

Thus, in some embodiments, the invention is directed to isolated and purified oligopeptides or polypeptides comprising a sequence of less than 552 amino acids. The oligopeptides or polypeptides of these embodiments comprise the amino acid sequence) XX(I/D/F/L)ENY(I/L)(E/W/Y)(L/M) (SEQ ID NO:16) or VMLENYTHL, (SEQ ID NO:12) where if the sequence is VMLENYTHL (SEQ ID NO:12), then the oligopeptide or polypeptide is less than 51 amino acids.

As used herein, "isolated and purified" means present in a greater concentration than would be found in nature. Preferably, an isolated and purified oligopeptide or polypeptide is at least about 10% of the peptide component of the preparation; more preferably at least about 25%; even more preferably at least about 50%; still more preferably at least about 75%; and most preferably at least about 90% of the peptide component of a preparation.

In preferred embodiments, these oligopeptides or polypeptides comprise the amino acid sequence (Y/F)(F/A/Q)(I/D)ENYL(E/Y)L (SEQ ID NO:20); in other preferred embodiments, the oligopeptides or polypeptides comprise the amino acid sequence X(A/Q/L/Y)(I/D/F/L)ENY(I/L)(F/W/Y)(L/M) (SEQ ID NO:21). In additional preferred embodiments, the oligopeptides or polypeptides comprise the amino acid sequence (Y/F)(A/Q)(I/D)ENYL(E/Y)L (SEQ ID NO:22). In more preferred embodiments, the oligopeptides or polypeptides comprise one of the amino acid sequences YAIENYLEL (SEQ. ID NO:13), FQDENYLYL (SEQ ID NO:9), RLFENYIEL (SEQ ID NO:10), or QYLENYLWM (SEQ ID NO:11). In other preferred embodiments, the oligopeptides or polypeptides comprise the amino acid sequence RLFENYIEL (SEQ ID NO:10), QYLENYLWM (SEQ ID NO:11), or VMLENYTHL (SEQ ID NO:12). The latter sequences are antigens that activate AI4-like CTLs more weakly than SEQ ID NOs:9, 13 or 14, and are useful in certain therapeutic regimes involving treatment with weak antigens (see PCT patent application PCT/US04/15752, filed May 20, 2004, incorporated by reference in its entirety; see also discussion below).

In other more preferred embodiments, the oligopeptide or polypeptide comprises the amino acid sequence YFIE-NYLEL (Mim, SEQ ID NO:14). In additional more preferred embodiments, the oligopeptide or polypeptide comprises the amino acid sequence YAIENYLEL (MimA2, SEQ ID NO:13), or FQDENYLYL (FNL9, SEQ ID NO:9) or RLFE-NYIEL (RIL9, SEQ ID NO:10), or QYLENYLWM (QM9, SEQ ID NO:1) or VMLENYTHL (VML9, SEQ ID NO:12).

In some preferred embodiments, the oligopeptide or polypeptide is completely homologous to a mammalian DMK or MRCKβ polypeptide having at least 90% homology to at least one of SEQ ID NO:1, SEQ ID NO:2, SEQ ID NO:3 or SEQ ID NO:4. More preferably, the oligopeptide or polypeptide is homologous to a mammalian DMK oligopeptide or polypeptide having at least 90% homology to at least one of SEQ ID NO:1 or SEQ ID NO:2.

In other preferred embodiments, the oligopeptide or polypeptide is homologous to TrEMBL accession Q8C1H3 or a mammalian analog thereof, Swiss-Prot accession Q9D4H1 or a mammalian analog thereof, or TrEMBL accession P97871 or a mammalian analog thereof In other preferred embodiments, the oligopeptides or polypeptides comprise 100 amino acids or less, more preferably 25 amino acids or less, even more preferably 13-25 amino acids, and most preferably 9-10 amino acids, since AI4-like CD8+ T cells generally only bind oligopeptides of 9-10 amino acids.

In further aspects of these embodiments, the oligopeptide or polypeptide also comprises an antigenic carrier, in order to more effectively use the peptides in immunization protocols, to tolerize a mammal to DMK, MRCKβ, TrEMBL accession Q8C1H3 or a mammalian analog thereof, Swiss-Prot accession Q9D4H1 or a mammalian analog thereof, or TrEMBL accession P97871 or a mammalian analog thereof, preventing development of type 1 diabetes, e.g., as was achieved in Example 2 of PCT/US04/15752 using an 8.3-like T cell antigen. A nonlimiting example of an antigenic carrier is incomplete Freund's adjuvant. See also Gammon et al., 1986.

In other aspects, the oligopeptides or polypeptides further comprise a detectable label. Such labeled peptides are useful in diagnostic protocols, e.g., to determine the presence of AI4-like CD8+ T cells, to identify a mammal that has, or is at risk for, type 1 diabetes. The invention is not limited to any particular detectable label, and the skilled artisan can select a label most appropriate for any particular application without undue experimentation. Examples include a fluorescent moiety, a radioactive molecule, and an assayable enzyme (e.g., β-galactosidase or streptavidin). Methods for labeling peptides with any of these detectable moieties are well known.

In further aspects, the above-identified oligopeptides of 9-10 amino acids can be usefully combined with an MHC class I molecule that is capable of binding the oligopeptide, for example a mouse H-2D$^b$ molecule, which binds the above-described antigens. Since CD8+ T cells only bind to an antigen in the context of an MHC class I molecule, the oligopeptide-MHC class I mixtures are useful for creating a T cell ligand. The MHC class I molecules are preferably employed in the form of tetramers. See, e.g., Altman et al., 1996; Trudeau et al., 2003. In some applications, e.g., diagnostics, the oligopeptide of the oligopeptide-MHC class I mixtures further comprises a detectable label, such as those previously discussed, conjugated to the oligopeptide. Alternatively or additionally, the MHC class I molecule could employ a detectable label.

In some methods of treatment, directed toward eliminating AI4-like CD8+ T cells, the oligopeptide or the MHC class I molecule can also include a cytotoxic molecule. In these methods, the cytotoxic oligopeptide-MHC class I mixture binds to the AI4-like T cell, where the cytotoxic molecule kills the T cell.

The invention is not narrowly limited to any particular cytotoxic molecule that is bound to the oligopeptide or MHC class I molecule. The skilled artisan could identify various cytotoxic molecules useful in these aspects, and could select the appropriate cytotoxic molecule for any particular application without undue experimentation. Examples of potentially useful cytotoxic molecules include radioactive molecules (e.g., $^{131}$I, $^{90}$Y), and toxic chemicals or proteins (e.g., 5-fluorouridine or ricin).

Since CD4+ T cells are also involved in the pathogenic process of type 1 diabetes, and since CD4+ T cells bind oligopeptides that are 13-25 amino acids, and only when presented on MHC class II molecules, mixtures of oligopeptides with MHC class II molecules are also within the scope of the invention. In these embodiments, the oligopeptides are 13-25 amino acids and comprise one of the sequences described above, e.g., XX(I/D/F/L)ENY(I/L)(E/W/Y)(L/M) (SEQ ID NO:16), (Y/F)(F/A/Q)(I/D)ENY(E/Y)L (SEQ ID NO:20), X(A/Q/L/Y)(I/D/F/L)ENY(I/L)(E/W/Y)(L/M) (SEQ ID NO:21), (Y/F)(A/Q)(I/D)ENYL(E/Y)L (SEQ ID NO:22), YAIENYLEL (SEQ ID NO:13), FQDENYLYL (SEQ ID NO:9), RLFENYIEL (SEQ ID NO:10), QYLE-NYLWM (SEQ ID NO:11), or VMLENYTHL (SEQ ID NO:12). Analogous to previously described oligopeptide-MHC class I mixtures, the oligopeptides or MHC class II molecules of the oligopeptide-MHC class II mixtures can also usefully comprise a detectable label or a cytotoxic molecule.

It is also envisioned that any of the above-described oligopeptides or polypeptides are usefully provided in a sterile pharmaceutical preparation, particularly when the oligopeptide or polypeptide is to be utilized for therapeutic treatments. Thus, in some embodiments, the oligopeptide or polypeptide in a sterile pharmaceutical preparation is capable of tolerizing a mammal to reduce CD8+ T cells reactive to DMK, MRCKβ, TrEMBL accession Q8C1H3 or a mammalian analog thereof, Swiss-Prot accession Q9D4H1 or a mammalian analog thereof, or TrEMBL accession P97871 or a mammalian analog thereof. Also included as useful in a sterile pharmaceutical preparation is the mammalian protein DMK, MRCKβ, TrEMBL accession Q8C1H3 or a mammalian analog thereof, Swiss-Prot accession Q9D4H1 or a mammalian analog thereof, or TrEMBL accession P97871 or a mammalian analog thereof, i.e., having at least 90% homology to SEQ ID NOs:1, 2, 3, 4, 5, 6, or 7. Preferably, the protein is a mouse or human protein. The oligopeptide or polypeptide in these sterile pharmaceutical preparation preferably comprises the amino acid sequence YAIENYLEL (SEQ ID NO:13), YFIE-NYLEL (SEQ ID NO:14), FQDENYLYL (SEQ ID NO:9), RLFENYIEL (SEQ ID NO:10), QYLENYLWM (SEQ ID NO:11), or VMLENYTHL (SEQ ID NO:12). In more preferred embodiments, the oligopeptide or polypeptide is homologous to a mammalian DMK or MRCKβ oligopeptide or polypeptide having at least 90% homology to at least one of SEQ ID NO:1, SEQ ID NO:2, SEQ ID NO:3 or SEQ ID NO:4; in even more preferred embodiments, the oligopeptide or polypeptide is homologous to a mammalian DMK oligopeptide or polypeptide having at least 90% homology to at least one of SEQ ID NO:1 or SEQ ID NO:2. In other embodiments, the oligopeptide or polypeptide is homologous to TrEMBL accession Q8C1H3 or a mammalian analog thereof, Swiss-Prot accession Q9D4H1 or a mammalian analog thereof, or TrEMBL accession P97871 or a mammalian analog thereof.

Thus, the invention is also directed to isolated and purified oligopeptides 9-10 amino acids in length, completely homologous with a mammalian DMK or MRCKβ or TrEMBL accession Q8C1H3 or a mammalian analog thereof, Swiss-Prot accession Q9D4H1 or a mammalian analog thereof, or TrEMBL accession P97871 or a mammalian analog thereof. In these embodiments, the oligopeptide has at least 90% homology to at least one of SEQ ID NO:1, SEQ ID NO:2, SEQ ID NO:3, SEQ ID NO:4, SEQ ID NO:5, SEQ ID NO:6 or SEQ ID NO:7, where the oligopeptide is capable of binding an MHC class I molecule of the mammal. As with embodiments described above, the oligopeptide preferably comprises the amino acid sequence XX(I/D/F/L)ENY(I/L)(E/W/Y)(L/M) (SEQ ID NO:16), (Y/F)(F/A/Q)(I/D)ENYL(E/Y)L (SEQ ID NO:20), X(A/Q/L/Y)(I/D/F/L)ENY(I/L)(E/W/Y)(L/M) (SEQ ID NO:21), (Y/F)(A/Q)(I/D)ENYL(E/Y)L (SEQ ID NO:22), YAIENYLEL (SEQ ID NO:13), YFIENYLEL(SEQ ID NO:14), FQDENYLYL (SEQ ID NO:9), RLFENYIEL (SEQ ID NO:10), QYLENYLWM (SEQ ID NO:11), or VMLENYTHL (SEQ ID NO:12).

In some preferred embodiments, particularly where the peptide is to be used diagnostically, the oligopeptide further comprises a detectable label as described above, e.g., a fluorescent molecule, a radioactive molecule, or an enzyme. These oligopeptides, either with or without the detectable label, can also comprise an MHC class I molecule that is capable of binding the oligopeptide, preferably H-2D$^b$. As with previously discussed embodiments, the oligopeptide-MHC class I mixture can also comprise a cytotoxic molecule, for example a radioactive molecule, conjugated to the oligopeptide or to the MHC class I molecule.

In additional embodiments, the invention is directed to kits comprising a sterile preparation comprising an isolated and purified oligopeptide 9-10 amino acids in length, where the peptide is completely homologous with a mammalian DMK, MRCKβ, TrEMBL accession Q8C1H3 or a mammalian analog thereof, Swiss-Prot accession Q9D4H1 or a mammalian analog thereof, or TrEMBL accession P97871 or a mammalian analog thereof, where the oligopeptide has at least 90% homology to at least one of SEQ ID NO:1, SEQ ID NO:2, SEQ ID NO:3, SEQ ID NO:4, SEQ ID NO:5, SEQ ID NO:6 or SEQ ID NO:7, and where the oligopeptide is capable of binding an MHC class I molecule of the mammal. In these embodiments, the sterile preparation is in a container. As with embodiments described above, the oligopeptide preferably comprises the amino acid sequence XX(I/D/F/L)ENY(I/L)(E/W/Y)(L/M) (SEQ ID NO:16), (Y/F)(F/A/Q)(I/D)ENYL(E/Y)L (SEQ ID NO:20), X(A/Q/D/Y)(T/F/L)ENY(I/L)(E/W/Y)(L/M) (SEQ ID NO:21), (Y/F)(A/Q)(I/D)ENYL(E/Y)L (SEQ ID NO:22), YAIENYLEL (SEQ ID NO:13), YFIENYLEL(SEQ ID NO:14), FQDENYLYL (SEQ ID NO:9), RLFENYIEL (SEQ ID NO:10), QYLENYLWM (SEQ ID NO:11), or VMLENYTHL (SEQ ID NO:12).

In some of these embodiments, the kits further comprise a second oligopeptide, where the second oligopeptide is capable of binding an MHC class I molecule of the mammal. In these embodiments, the first oligopeptide may be in a separate container from the second oligopeptide, or the first oligopeptide and second oligopeptide may be mixed in the same sterile preparation. The second oligopeptide may be an antigen to an AI4-like T cell, such as XX(I/D/F/L)ENY(I/L)(E/W/Y)(L/M) (SEQ ID NO:16), (Y/F)(F/A/Q)(I/D)ENYL(E/Y)L (SEQ ID NO:20), X(A/Q/D/Y)(T/F/L)ENY(I/L)(E/W/Y)(L/M) (SEQ ID NO:21), (Y/F)(A/Q)(I/D)ENYL(E/Y)L (SEQ ID NO:22), YAIENYLEL (SEQ ID NO:13), YFIENYLEL (SEQ ID NO:14), FQDENYLYL (SEQ ID NO:9), RLFENYIEL (SEQ ID NO:10), QYLENYLWM (SEQ ID NO:11), or VMLENYTHL (SEQ ID NO:12). In other embodiments, the second oligopeptide is an antigen to an 8.3-like T cell, as would be expected, for example, with oligopeptides comprising an amino acid sequence selected from the group consisting of YLKTN(A/I/L/V)FL (SEQ ID NO:47), FLWSVFWLI (SEQ ID NO:48), (T/A)YY(G/T)FLNFM (SEQ ID NO:49), LR(L/V)(F/L)(G/N)IDLL (SEQ ID NO:50), KWCANPDWI (SEQ ID NO:51), SFCKSASIP (SEQ ID NO:52), and YNIANWFL (SEQ ID NO:53). See PCT/US04/15752, incorporated by reference. In additional embodiments, the second oligopeptide is an antigen to a G9C8-like T cell, for example LYLVCGERG (SEQ ID NO:19).

The kits of these embodiments can further comprise a third, fourth, etc. oligopeptide that is capable of binding an MHC class I molecule of the mammal. The kits can also further comprise a tetramer of an MHC class I molecule, for example mouse H-2D$^b$.

In some of these embodiments, the oligopeptide in the kit is a medium- or low-affinity ligand to an AI4 CTL, for example RLFENYIEL(SEQ ID NO:10), QYLENYLWM (SEQ ID NO:11), or VMLENYTHL (SEQ ID NO:12).

Therapy to reduce or eliminate expression of proteins bearing AI4-like T cell antigens on islet cells is beneficial in reducing or eliminating pathogenic islet cell destruction in type 1 diabetes, since such a therapy would eliminate the target ligand for the autoimmune reactions leading to type 1 diabetes. The reduction or elimination of expression of these proteins can be achieved by treatment with antisense molecules, ribozymes, or RNAi molecules that target the mRNA of the protein. In these embodiments, the antisense molecule, ribozyme, or RNAi molecules can be comprised of nucleic acid (e.g., DNA or RNA) or nucleic acid mimetics (e.g., phosphorothionate mimetics) as are known in the art.

Thus, in some embodiments, the invention is directed to antisense molecules complementary to at least a portion of a mammalian (preferably mouse or human) mRNA encoding a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof In these embodiments, the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof is at least 90% homologous to at least one of SEQ ID NO:1, SEQ ID NO:2, SEQ ID NO:3, SEQ ID NO:4, SEQ ID NO:5, SEQ ID NO:6, or SEQ ID NO:7. The antisense molecule in these embodiments is capable of inhibiting translation of the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof. In preferred embodiments, the mammalian mRNA encodes a DMK. Sequences of NOD mouse DMK and MRCKβ cDNAs are provided herewith as SEQ ID NO:8 and SEQ ID NO:15, respectively. Other relevant sequences are known in the art.

In other embodiments, the invention is directed to ribozymes specific for a portion of a mammalian (preferably mouse or human) mRNA encoding a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof, where the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof is at least 90% homologous to at least one of SEQ ID NO:1, SEQ ID NO:2, SEQ ID NO:3, SEQ ID NO:4, SEQ ID NO:5, SEQ ID NO:6, or SEQ ID NO:7. In these embodiments, the ribozyme is capable of inhibiting translation of the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof. Preferably, the mammalian mRNA encodes a DMK.

In additional embodiments, the invention is directed to RNAi molecules homologous to a portion of a mammalian (preferably mouse or human) mRNA encoding a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof, where the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof is at least 90% homologous to at least one of SEQ ID NO:1, SEQ ID NO:2, SEQ ID NO:3, SEQ ID NO:4, SEQ ID NO:5, SEQ ID NO:6, or SEQ ID NO:7. In these embodiments, the RNAi molecule is capable of inhibiting translation of the mammalian DMK, MRCKβ, TrEMBL accession Q8C1H3 or mammalian analog thereof, Swiss-Prot accession Q9D4H1 or mammalian analog thereof, or TrEMBL accession P97871 or mammalian analog thereof. Preferably, the mammalian mRNA encodes a DMK.

The inventors have also discovered that cDNAs of the NOD mouse DMK and MRCKβ, provided herewith as SEQ ID NO:8 and SEQ ID NO:15, respectively, have a nucleotide sequence that differs from the published mouse DMK and MRCKβ cDNA sequences. These cDNAs also encode NOD DMK or MRCKβ proteins (SEQ ID NO:1 and 3, respectively) that differ from published mouse DMK or MRCKβ amino acid sequences.

Thus, in some embodiments, the invention is directed to cDNAs having the nucleotide sequence of SEQ ID NO:8 or SEQ ID NO:15, and isolated and purified proteins having the amino acid sequence of SEQ ID NO:1 or SEQ ID NO:3. Vectors comprising the NOD DMK or MRCKβ cDNA sequences are also within the scope of the invention, as are cells transfected with those vectors. The cells can be prokaryotic, archaeal, or eukaryotic cells. Preferably, they are mammalian cells. Such cells can be in culture or can be part of a living mammal.

The invention is further directed to mammalian pancreatic islet β cells comprising any of the antisense molecules, the ribozymes, or the RNAi molecules described above. These transfected β cells can also be transplanted in a mammal, preferably a mammal that has type 1 diabetes. The mammals of these embodiments are preferably mice or humans.

Many of the above-described compositions are useful in methods of treating mammals (including but not limited to humans and rodents such as mice) that are at risk for, or have type 1 diabetes. As such, the above-described compositions can be formulated without undue experimentation for administration to a mammal, including humans, as appropriate for the particular application. Additionally, proper dosages of the compositions can be determined without undue experimentation using standard dose-response protocols.

Accordingly, the compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

The compositions of the present invention can easily be administered parenterally such as for example, by intravenous, intramuscular, intrathecal or subcutaneous injection. Parenteral administration can be accomplished by incorporating the compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

The present invention includes nasally administering to the mammal a therapeutically effective amount of the composition. As used herein, nasally administering or nasal administration includes administering the composition to the mucous membranes of the nasal passage or nasal cavity of the patient. As used herein, pharmaceutical compositions for nasal administration of a composition include therapeutically effective amounts of the composition prepared by well-known methods to be administered, for example, as a nasal spray, nasal drop, suspension, gel, ointment, cream or powder. Administration of the composition may also take place using a nasal tampon or nasal sponge.

Accordingly, in some embodiments, the invention is directed to methods of treating a mammal that is at risk for or has type 1 diabetes. The methods comprise administering an oligopeptide or polypeptide to the mammal in a manner sufficient to reduce CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal. In these methods, the oligopeptide or polypeptide comprises the amino acid sequence XX(I/D/F/L)ENY(I/L)(E/W/Y)(L/M) (SEQ ID NO:16) or VMLENYTHL (SEQ ID NO:12). In some preferred embodiments, the oligopeptide or polypeptide comprises the amino acid sequence (Y/F)(F/A/Q)(I/D)ENYL(E/Y)L (SEQ ID NO:22), X(A/Q/L/Y)(I/D/F/L)ENY(I/L)(E/W/Y)(L/M) (SEQ ID NO:21), or (Y/F)(A/Q)(I/D)ENYL(E/Y)L (SEQ ID NO:22). In more preferred embodiments, the oligopeptide or polypeptide comprises the amino acid sequence YAIENYLEL (SEQ ID NO:13), YFIENYLEL(SEQ ID NO:14), FQDENYLYL (SEQ ID NO:9), RLFENYIEL (SEQ ID NO:10), QYLENYLWM (SEQ ID NO:11), VMLENYTHL (SEQ ID NO:12).

In some aspects of these methods, the oligopeptide or polypeptide treatment tolerizes the mammal to eliminate the T cells. Where the T cells are $CD8^+$, these methods would reduce or eliminate T cells reactive to the proteins in β cells that have an antigen to an AI4-like T cell. The oligopeptides or polypeptides of these embodiments are described above. They can be any size considered appropriate by the skilled artisan as appropriate for tolerization protocols, including 8-10 mers, 13-25 mers, or less than 25, or less than 50, or less than 100, or less than 300, or even larger, including an entire DMK, MRCKβ, TrEMBL accession Q8C1H3 or analog thereof in the mammal, Swiss-Prot accession Q9D4H1 or analog thereof in the mammal, or TrEMBL accession P97871 or analog thereof in the mammal, or several of the peptides conjugated to an inert or immunogenic carrier. Protocols for tolerizing a mammal to T cell reactivity are well known. See, e.g., Gammon et al., 1986.

These methods include embodiments where more than one of the above-identified oligopeptides is used in the treatment, in order to eliminate other reactive $CD8^+$ T cells.

In preferred embodiments of these methods, the oligopeptide or polypeptide is an oligopeptide having 9-10 amino acids, such that the oligopeptide is capable of binding to a AI4-like T cell in the context of an MHC molecule, e.g., an MHC tetramer or an antigen presenting cell (APC), making the T cell unavailable for binding to a β cell, thus reducing or eliminating β cell destruction. The oligopeptide in these embodiments can further comprise a cytotoxic molecule, in order to kill the AI4-like T cells.

These methods can also comprise treating the mammal with a second oligopeptide, where the second oligopeptide is 840 amino acids in length and is capable of binding to an MHC class I molecule of the mammal. These second oligopeptides can also be antigens of AI4-like T cells, such as YAIENYLEL (SEQ ID NO:13), YFIENYLEL (SEQ ID NO:14), FQDENYLYL (SEQ ID NO:9), RLFENYIEL (SEQ ID NO:10), QYLENYLWM (SEQ ID NO:11), or VMLENYTHL (SEQ ID NO:12). Alternatively, the second oligopeptide is an antigen of an 8.3-like T cell, for example YLKTN(A/I/L/V)FL (SEQ ID NO:47), FLWSVFWLI (SEQ ID NO:48), (T/A)YY(G/T)FLNFM (SEQ ID NO:49), LR(L/V)(F/L)(G/N)IDLL (SEQ ID NO:50), KWCANPDWI (SEQ ID NO:51), SFCKSASIP (SEQ ID NO:52), or YNIANWFL (SEQ ID NO:53). The second oligopeptide can also be an antigen of a G9C8 T cell clone. An example of such an oligonucleotide comprises the amino acid sequence LYLVCGERG (SEQ ID NO:19).

The mammal can also be treated with a third or fourth oligopeptide, where the third oligopeptide is capable of binding an MHC class I molecule of the mammal.

Any of the oligopeptides used in these methods can further comprise a cytotoxic molecule, such that the oligopeptide can kill AI4-like T cells upon binding in the context of an MHC molecule.

In some of these methods, a class I MHC molecule capable of binding the oligopeptide is also included with the oligopeptide, in such a manner as to cause oligopeptide-MHC binding. The oligopeptide and/or the class I MHC molecule in these embodiments can further comprise a cytotoxic molecule, as described above. The oligopeptide-cytotoxic molecule is administered to the mammal in a manner sufficient to reduce AI4-like $CD8^+$ T cells. The reduction in $CD8^+$ T cells is achieved when the peptide-MHC molecule-cytotoxic molecule binds to the AI4-like T cell, which is killed by the cytotoxic molecule. As with the embodiments described above, more than one oligopeptide can be administered.

In these embodiments, the MHC class I molecules are preferably employed in the form of tetramers. See, e.g., Altman et al., 1996; Trudeau et al., 2003. However, the MHC class I molecule can also be present as part of an antigen-presenting cell. Such compositions are particularly useful for measuring cytokine (particularly interferon-γ) production from $CD8^+$ T cells.

In related embodiments, the invention is directed to additional methods of treating a mammal, where the mammal is at risk for or has type 1 diabetes. These methods comprise administering to the mammal an oligopeptide 9-10 amino acids in length that is completely homologous with a mammalian DMK, MRCKβ, a TrEMBL accession Q8C1H3 or mammalian analog thereof, a Swiss-Prot accession Q9D4H1 or mammalian analog thereof, or a TrEMBL accession P97871 or mammalian analog thereof, and is capable of binding a mammalian MHC class I molecule, as described above. The oligopeptide is preferably completely homologous with a mammalian DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof having at least 90% homology to SEQ ID NOs:1, 2, 3, 4, 5, 6 or 7. In these methods, a class I MHC molecule capable of binding the oligopeptide can also be included with the oligopeptide, in such a manner as to cause oligopeptide-MHC binding. In these embodiments, the oligopeptide and/or the class I MHC molecule can further comprise a cytotoxic molecule, as described above. The oligopeptide-cytotoxic molecule is administered to the mammal in a manner sufficient to reduce $CD8^+$ T cells reactive to a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof. The reduction in $CD8^+$ T cells is achieved when the peptide-MHC molecule-cytotoxic molecule binds to the AI4-like T cell, which is then killed by the cytotoxic molecule.

As shown in PCT/US04/15752, a particularly effective type 1 diabetes treatment is with an oligopeptide that has medium- or low-affinity binding to the cytotoxic $CD8^+$ T cell. Thus, the invention is also directed to additional methods of treating a mammal, wherein the mammal is at risk for or has type 1 diabetes. The methods comprise administering an oligopeptide 8-10 amino acids in length to the mammal, wherein the oligopeptide is a medium- or low-affinity ligand to an AI4-like T cell, and the oligopeptide is homologous to a $CD8^+$ T cell that is reactive to a DMK, an MRCKβ, a TrEMBL accession Q8C1H3 or mammalian analog thereof, a Swiss- Prot accession Q9D4H1 or mammalian analog thereof, or a TrEMBL accession P97871 or mammalian analog thereof. Preferred examples of useful oligonucleotides for these methods are RLFENYIEL (SEQ ID NO:10), QYLENYLWM (SEQ ID NO:11), and VMLENYTHL (SEQ ID NO:12).

In further embodiments, the invention is directed to methods of preventing an AI4-like CD8+ T cell that is cytotoxic to pancreatic islet β cells from destroying a β cell. These methods comprise treating the β cell with a compound capable of binding an oligopeptide that is 9-10 amino acids in length and completely homologous with a mammalian DMK, MRCKβ, a TrEMBL accession Q8C1H3 or mammalian analog thereof, a Swiss-Prot accession Q9D4H1 or mammalian analog thereof, or a TrEMBL accession P97871 or mammalian analog thereof, as described above. By binding antigens presented on the β cell that react with AI4-like T cells, reaction of the AI4-like T cells with the antigen can be prevented, thus preventing destruction of the β cell. The oligopeptide is preferably completely homologous to a mammalian DMK, MRCKβ, a TrEMBL accession Q8C1H3 or mammalian analog thereof, a Swiss-Prot accession Q9D4H1 or mammalian analog thereof, or a TrEMBL accession P97871 or mammalian analog thereof having at least 90% homology to SEQ ID NOs:1, 2, 3, 4, 5, 6 or 7. In these embodiments, the oligopeptide-binding compound prevents binding of the oligopeptide to the MHC, or prevents binding of the oligopeptide-MHC complex to a CD8+ T cell.

In preferred embodiments, the compound can bind an oligopeptide or polypeptide comprising the sequence (Y/F)(F/A/Q)(I/D)ENYL(E/Y)L (SEQ ID NO:22), X(A/Q/L/Y)(I/D/F/L)ENY(I/L)(E/W/Y)(L/M) (SEQ ID NO:21), or (Y/F)(A/Q)(I/D)ENYL(E/Y)L (SEQ ID NO:22). In more preferred embodiments, the oligopeptide or polypeptide comprises the amino acid sequence YAIENYLEL (SEQ ID NO:13), YFIENYLEL (SEQ ID NO:14), FQDENYLYL (SEQ ID NO:9), RLFENYIEL (SEQ ID NO:10), QYLENYLWM (SEQ ID NO:11), VMLENYTHL (SEQ ID NO:12).

In these embodiments, the compound capable of binding the oligopeptide can be any compound capable of interfering with the CD8+ binding to the β cell, either by reducing the numbers of oligopeptide-MHC binding, or by causing a physical interference to the T cell binding to the oligopeptide-MHC complex. In preferred embodiments, the compound is an antibody or an aptamer.

Methods of making antibodies to an oligopeptide are routine, and the skilled artisan would expect that such an antibody could be made to any of the above-described oligopeptides without undue experimentation. The antibodies can be from a polyclonal, monoclonal, or recombinant source. As used herein, "antibodies" also include a fragment of a whole antibody that comprises a typical immunoglobulin antigen binding site (e.g., Fab or Fab2). The antibodies can also be of any vertebrate (e.g., mouse, chicken, rabbit, goat or human), or of a mixture of vertebrates (e.g., humanized mouse).

Aptamers are single stranded oligonucleotides or oligonucleotide analogs that bind to a particular target molecule, such as a protein or a small molecule (e.g., a steroid or a drug, etc.). Thus, aptamers are the oligonucleotide analogy to antibodies. However, aptamers are smaller than antibodies, generally in the range of 50-100 nt. Their binding is highly dependent on the secondary structure formed by the aptamer oligonucleotide. Both RNA and single stranded DNA (or analog), aptamers are known.

Aptamers that bind to virtually any particular target can be selected by using an iterative process called SELEX, which stands for Systematic Evolution of Ligands by EXponential enrichment. Several variations of SELEX have been developed which improve the process and allow its use under particular circumstances. See the references cited in PCT/US04/15752, all of which are incorporated by reference. Thus, the production of aptamers to any particular oligopeptide, including the oligopeptide antigens to AI4-like T cells described above, requires no undue experimentation.

Additionally, the pancreatic islet β cell in these methods can be treated ex vivo or in vitro (e.g., on islet β cells that are for transplanting into a patient having type 1 diabetes). In preferred embodiments, the islet β cell is part of a pancreas of a mammal at risk for or having type 1 diabetes. While the methods are not limited to the use with any particular mammal, a mouse or a human is preferred.

The present invention is also directed to methods of preventing AI4-like T cells that are cytotoxic to pancreatic islet β cells from killing a β cell. The methods comprise treating the T cells with an oligopeptide of 940 amino acids comprising XX(I/D/F/L)ENY(I/L)(E/W/Y)(L/M) (SEQ ID NO:16) and VMLENYTHL (SEQ ID NO:12) as described above. Preferably, the oligopeptide comprises the amino acid sequence X(A/Q/L/Y)(I/D/F/L)ENY(I/L)(E/W/Y)(L/M) (SEQ ID NO:21) or (Y/F)(A/Q)(I/D)ENYL(E/Y)L (SEQ ID NO:22), also as described above. In some of these embodiments, the oligopeptide farther comprises a cytotoxic molecule, in order to kill the AI4-like T cell. In preferred embodiments, the pancreatic islet β cell is part of a pancreas of a mammal at risk for or having type 1 diabetes.

Additionally, the present invention is directed to methods of treating a mammal at risk for type 1 diabetes. The methods of these embodiments comprise administering to the mammal a compound capable of specifically decreasing expression of a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof in the mammal. In these embodiments, the compound is the antisense molecule, the ribozyme, or the RNAi molecule previously described, where the compound is administered in a manner sufficient to decrease expression in the mammal of a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal. While the methods are not limited to the use with any particular mammal, a mouse or a human is preferred.

A known method of treatment of mammals (including humans) having type 1 diabetes is transplanting pancreatic islet β cells into the pancreas of the mammal. However, since β cell-autoreactive CD8+ T cells are generally present after transplant, the transplanted β cells are often also destroyed. The present invention provides methods for reducing or eliminating this destruction of the transplanted β cells. The methods involve transfecting the β cells with a vector expressing a nucleic acid that reduces or eliminates expression of a DMK, an MRCKβ, a TrEMBL accession Q8C1H3 or mammalian analog thereof, a Swiss-Prot accession Q9D4H1 or mammalian analog thereof, or a TrEMBL accession P97871 or mammalian analog thereof in the cells. The transfected cells, which after treatment express little or no antigen to an AI4-like T cell, are then transplanted into the mammal. Since those cells express little or no antigen to an AI4-like T cell, autoreactive CD8+ T cells are not able to bind to and destroy the β cells.

Thus, in these embodiments, the invention is directed to additional methods of treating a mammal having type 1 diabetes. The methods comprise transplanting pancreatic islet β cells into the pancreas of the mammal, where the β cells are transfected with a vector that expresses a nucleic acid. The nucleic acid is any of the antisense molecules described above, the ribozymes described above, or the RNAi molecules described above. In these embodiments, the nucleic acid is expressed in a manner sufficient to decrease expression of an AI4-like T cell antigen in the β cells.

These embodiments are not limited to any particular type of vector. As is well known in the art, examples of suitable vectors include a naked DNA vector and a viral vector (e.g., adenoviral or lentiviral). The skilled artisan can select and synthesize an appropriate vector without undue experimentation. As with other embodiments, the methods are also not limited to use with any particular mammal. In preferred embodiments, the mammal is a mouse or a human.

The discovery of antigens to AI4-like T cells suggests several diagnostic methods.

Accordingly, in some embodiments, the invention is directed to methods for determining whether a mammal is at risk for or has type 1 diabetes. The methods comprise determining the presence of CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal by a. obtaining a sample of lymphocytes comprising CD8+ T cells from the mammal;

b. combining the lymphocytes with an oligopeptide and an MHC class I molecule that is capable of binding the oligopeptide, where the oligopeptide or the MHC molecule further comprises a detectable label and where the oligopeptide is 9-10 amino acids in length and comprises a selected from the group consisting of XX(I/D/F/L)ENY(I/L)(E/W/Y)(L/M) (SEQ ID NO:16) and VMLENYTHL (SEQ ID NO:12); and c. determining whether any CD8+ T cells specifically interact with the oligopeptide. In these embodiments, CD8+ T cell binding to the oligopeptide indicates that the mammal is at risk for or has type 1 diabetes.

In some preferred embodiments, the oligopeptide comprises the amino acid sequence X(A/Q/L/Y)(I/D/L/Y)ENY (I/L)(E/W/Y)(L/M) (SEQ ID NO:21) or (Y/F)(A/Q)(I/D) ENYL(E/Y)L (SEQ ID NO:22). Other preferred oligopeptides have SEQ ID NOs:9-14.

These methods can be used with any mammal, although the mammal is preferably a mouse or a human.

The determination step (c.) can be by any known means. In some preferred embodiments, the determination step is performed by counting labeled CD8+ T cells using a cell sorter (e.g., a fluorescence activated cell sorter) or labeled cell counter (e.g., Coulter counter). In other preferred embodiments, the determination step is performed by microscopic observation of the lymphocytes under conditions where the label can be observed, e.g., with a fluorescence microscope if a fluorescent label is used, or light microscope if an enzyme label and colored enzyme substrate is used to visualize the bound T cells. In additional preferred embodiments, the determination step is performed by measuring activation of the CD8+ T cells, preferably by measuring interferon-γ production by known methods, for example using an ELISpot assay (see, e.g., Hartemann et al., 1999).

The invention is also directed to other methods for determining whether a mammal is at risk for or has type I diabetes. The methods comprise determining the presence of CD8+ T cells reactive to a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal by a. obtaining a sample of lymphocytes comprising CD8+ T cells from the mammal;

b. combining the lymphocytes with an oligopeptide and an MHC class I molecule that is capable of binding the oligopeptide, wherein the oligopeptide or the MHC molecule further comprises a detectable label and wherein the oligopeptide is 9-10 amino acids and is completely homologous with the a DMK, an MRCKβ, a TrEMBL accession Q8C1H3 or analog thereof in the mammal, a Swiss-Prot accession Q9D4H1 or analog thereof in the mammal, or a TrEMBL accession P97871 or analog thereof in the mammal; and c. determining whether any CD8+ T cells specifically bind to the oligopeptide, wherein CD8+ T cell binding to the oligopeptide indicates that the mammal is at risk for or has type I diabetes.

Preferred embodiments of the invention are described in the following Examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims, which follow the Examples.

Example 1

Requirement for Both H-2D$^b$ and H-2K$^d$ for the Induction of Diabetes by the Promiscuous CD8+ T Cell Clonotype AI4

Example Summary

The NOD mouse is a model for autoimmune type 1 diabetes in humans. CD8+ T cells are essential for the destruction of the insulin-producing pancreatic β cells characterizing this disease. AI4 is a pathogenic CD8+ T cell clone, isolated from the islets of a 5-week-old female NOD mouse, which is capable of mediating overt diabetes in the absence of CD4+ T cell help. Recent studies using MHC-congenic NOD mice revealed marked promiscuity of the AI4 TCR, as the selection of this clonotype can be influenced by multiple MHC molecules, including some class II variants. The present work was designed, in part, to determine whether similar promiscuity also characterizes the effector function of mature AI4 CTL. Using splenocyte and bone marrow disease transfer models and in vitro islet-killing assays, we report that efficient recognition and destruction of β cells by AI4 requires the β cells to simultaneously express both H-2D$^b$ and H-2K$^d$ class I MHC molecules. The ability of the AI4 TCR to interact with both H-2D$^b$ and H-2K$^d$ was confirmed using recombinant peptide libraries. This approach also allowed us to define a mimotope peptide recognized by AI4 in an H-2D$^b$-restricted manner. Using ELISPOT and mimotope/H-2D$^b$ tetramer analyses, we demonstrate for the first time that AI4 represents a readily detectable T cell population in the islet infiltrates of prediabetic NOD mice. Our identification of a ligand for AI4-like T cells will facilitate further characterization and manipulation of this pathogenic and promiscuous T cell population.

Introduction

Crosses between NOD.AI4αβ Tg mice and NOD stocks congenic for a variety of MHC haplotypes were recently used to determine whether the development of pathogenic CD8+ T cells could be affected by MHC variants within haplotypes known to dominantly inhibit T1D (Serreze et al., 2004). This work revealed that, when expressed on bone marrow-derived APC, MHC molecules within the H2$^{nb1}$ and H2$^b$ haplotypes, including one or both of the H2$^{nb1}$-encoded class II molecules, could influence AI4 T cell selection through the induction of thymic deletion or anergy. Thus, the AI4 TCR is capable of tolerogenic interactions with a number of different MHC molecules during T cell development. We now demonstrate that mature AI4 CTL also exhibit promiscuous recognition of multiple peptide/MHC complexes and report the surprising finding that β cell co-expression of both H-2D$^b$ and H-2K$^d$ is required for their efficient recognition and destruction by AI4 T cells. Further, we have identified a synthetic ligand for AI4, and we have used this advance to demonstrate that, as has been previously shown for 8.3- and G9C8-like T cells, AI4-like T cells constitute a readily detectable population within the islets of prediabetic NOD mice. This brings to three the number of pathogenic CD8$^+$ T cell populations in NOD mice that can now be manipulated and monitored.

Materials and Methods

Mice. NOD/Lt mice (H2$^{g7}$ MHC haplotype, i.e., K$^d$, A$^{g7}$, E$^{null}$, D$^b$) are maintained by brother-sister mating. Previously described T1D-resistant strains of lymphocyte-deficient NOD-scid.Emv30$^{null}$ mice (Serreze et al., 2994) and class I MHC-deficient NOD.β2m$^{null}$ mice (Serreze et al., 1994) are all maintained at the N11 backcross generation. Previously described stocks (Prochazka et al., 1989; Wicker et al., 1992) of T1D-resistant NOD mice congenic for the H2$^{nb1}$ (K$^b$, A$^{nb1}$, E$^k$, D$^b$) or H2$^b$ (K$^b$, A$^b$, E$^{null}$, D$^b$) haplotypes are designated NOD.H2$^{nb1}$ or NOD.H2$^b$ and are maintained at the N21 or N15 backcross generation, respectively. T1D-resistant NOD mice congenic for a previously described (Cosgrove et al., 1991) class II-deficient H2$^b$ haplotype (K$^b$, A$^{null}$, E$^{null}$, D$^b$) are maintained at the N11 backcross generation (designated NOD.H2$^b$-Ab$^0$ mice). A newly developed N10 backcross generation stock of NOD mice congenic for the ALR-derived H2$^{gx}$ haplotype (K$^d$, A$^{g7}$, E$^{null}$, D$^{dx}$) (Graser et al., 1999) is partially T1D-resistant (female incidence of 35% at 25 weeks of age compared to 90% for standard NOD females at The Jackson Laboratory). These NOD.H2$^{gx}$ mice were obtained from E. Leiter (The Jackson Laboratory, Bar Harbor, Me.). NOD-K$^b$ Tg mice have been previously described (Serreze et al., 2004). Expression of the H-2K$^b$ transgene does not alter the incidence of T1D development in these mice. NOD mice transgenically expressing the TCR of the β cell-autoreactive CD8$^+$ T cell clone AI4 (Vα8/Vβ2), and a substock congenic for a functionally inactivated Rag1 gene (designated NOD.AI4αβ Tg or NODRag1$^{null}$.AI4αβ Tg mice), have also both been previously described (DiLorenzo et al., 2002; Graser et al., 2000). 8.3-NOD mice transgenically express the TCR of the β cell-autoreactive CD8$^+$ T cell clone 8.3 (Vα17/Vβ8S1) (Verdaguer et al., 1997). C57BL/6 mice congenic for the H2$^{g7}$ haplotype are maintained at the N8 backcross generation and designated B6.H2$^{g7}$ (Yui et al., 1996). Lymphocyte-deficient CB17-scid (K$^d$, A$^d$, E$^d$, D$^d$) (Shultz et al., 1989) and B6-scid (K$^b$, A$^b$, E$^{null}$, D$^b$) stocks (Christianson et al., 1996) have been previously described. C57BL/10 mice congenic for the H2$^d$ haplotype (K$^d$, A$^d$, E$^d$, D$^d$) derived from the DBA/2 strain were obtained from The Jackson Laboratory (Bar Harbor, Me.) and are designated B10.D2. All mice are maintained under specific pathogen-free conditions and used in accordance with institutional guidelines for animal welfare. All scid mice receive a sulfamethoxazole-trimethoprim mixture in their drinking water on alternate weeks to prevent infection by Pneumocystis carinii (Shultz et al., 1989).

Cell lines. RMA-S/K$^d$ (generously provided by M. Bevan, University of Washington, Seattle, Wash.) was derived from the TAP-deficient cell line RMA-S (Karre et al., 1986) and engineered to express H-2K$^d$ in addition to the endogenous H-2K$^b$ and H-2D$^b$. The TAP-deficient cell line T2 (Salter et al., 1985) was obtained from the American Type Culture Collection (Manassas, Va.). T2-K$^d$ (generously provided by J. Yewdell, NIAID, Bethesda, Md.) was derived from T2 and engineered to express H-2K$^d$ in addition to the endogenous HLA-A2.1. The NIT-1β cell line, established from an adenoma that arose in an NOD mouse transgenically expressing SV40 T antigen under the control of a rat insulin promoter, was maintained in a complete medium previously described (Hamaguchi et al., 1991). For IFN-γ treatment, NIT-1 cells were cultured overnight in this complete medium supplemented with 10 U/ml IFN-γ (murine recombinant; PeproTech, Inc., Rocky Hill, N.J.).

Isolation of peptides from immunoaffinity purified MHC class I. H-2K$^d$ and H-2D$^b$ molecules were immunoaffinity purified from $4 \times 10^9$ IFN-γ-treated NIT-1 pancreatic β cells using the mAbs SF1-1.1 (anti-H-2K$^d$) and 28-14-8 (anti-H-2D$^b$) (hybridomas from the American Type Culture Collection, Manassas, Va.) and their associated peptides extracted as previously described (Cox et al., 1997). Peptide extracts were fractionated by reverse-phase HPLC as described (DiLorenzo et al., 2002).

Peptide libraries and synthetic peptides. Positional scanning combinatorial peptide libraries (Borras et al., 2002), mimotope candidate peptides (including YFIENYLEL (SEQ ID NO:14), designated Mim), and alanine-substituted Mim peptides (including the F2A variant, designated MimA2) were purchased from Mimotopes (Victoria, Australia). NRP-V7 (KYNKANVFL) (SEQ ID NO:17), INS-19 (G9I variant of murine insulin B$_{15-23}$; LYLVCGERI (SEQ ID NO:54)), INS BC (murine insulin 2 B$_{25}$-C$_{34}$; FYTPMSRREV (SEQ ID NO:23)), GAD65$_{206}$ (murine glutamic acid decarboxylase (GAD) 65$_{206-214}$; TYEIAPVFV (SEQ ID NO:24)), GAD65$_{546}$ (murine GAD65$_{546-564}$; SYQPLGDKV (SEQ ID NO:25)), and TRL9 (a negative control H-2D$^b$-binding peptide; TSPRNSTVL (SEQ ID NO:26)) peptides were synthesized by standard solid-phase methods using fluorenylmethoxycarbonyl chemistry in an automated peptide synthesizer (model 433A; Applied Biosystems, Foster City, Calif.), and their identities were confirmed by mass spectrometry.

Pancreatic islet isolation and culture. Islet isolation by collagenase P perfusion of the common bile duct was modified from a previously described protocol (Leiter, 1997). Briefly, the bile duct was cannulated and the pancreas perfused with collagenase P (Boehringer Mannheim, Mannheim, Germany). The inflated pancreas was removed, and incubated at 37° C. to digest exocrine tissue. Following dispersion of digested tissue and three washes with HBSS, islets were resuspended in HBSS containing DNase I (Worthington Biochemical Corporation, Lakewood, N.J.) and handpicked using a silanized micropipet under a dissecting microscope. Isolated islets were washed with FBS-containing HBSS, resuspended in RPMI medium supplemented with 10% FBS (Hyclone, Logan, Utah) and 50 U/ml recombinant human IL-2 (PeproTech, Inc., Rocky Hill, N.J.), and cultured in 24-well tissue culture plates (~50 islets/well) at 37° C., 5% CO$_2$ for 7 days. The incubation of NOD islets in IL-2-supplemented medium allows for the expansion of β cell-autoreactive CD8$^+$ T cells (Amrani et al., 2000).

Splenocyte adoptive transfer. Aliquots of $1 \times 10^7$ splenic leukocytes isolated as described (Christianson et al., 1993) from prediabetic female NOD.Rag1$^{null}$.AI4αβ Tg donors were injected intravenously into irradiated (700-750 rad from a $^{137}$Cs source) mice or non-irradiated scid mice as indicated in the figures. Recipient mice were monitored for diabetes development for up to 20 weeks after transfer. At diabetes onset or the end of the observation period, recipient splenocytes were analyzed by multicolor flow cytometry for extent of AI4 T cell reconstitution.

Bone marrow transfer. Mice were lethally irradiated (1200-1400 rad from a $^{137}$Cs source) at 4-6 weeks of age and reconstituted as previously described (Serreze and Leiter, 1991) with $5 \times 10^6$ bone marrow cells from prediabetic female NOD.Rag1$^{null}$.AI4αβ Tg donors. Recipient mice were monitored for diabetes development for up to 20 weeks after reconstitution. At diabetes onset or at the end of the observation period, recipient splenocytes were analyzed by multicolor flow cytometry for extent of AI4 T cell reconstitution.

Cytotoxicity assays using intact islets as targets. NOD pancreatic islets (10/well) were allowed to adhere in 96-well plates during a 7-10 day incubation at 37° C. in low-glucose DMEM medium (DiLorenzo et al., 1998). Adherent islets were then labeled with 5 μCi/well of $^{51}$Cr for 3 hours at 37° C. Islets were washed and overlaid with 100 μl of medium containing various numbers of T cells from NOD.AI4αβ Tg mice that had been pre-activated for 72 hours with the mimotope peptide YFIENYLEL (SEQ ID NO:14) at a concentration of 10 nM. For establishing E:T ratios, each islet was assumed to contain ~800 cells. A minimum of three wells were set up for each E:T ratio. Controls consisted of at least six wells of labeled NOD islets cultured in the absence of T cells. Following an overnight incubation at 37° C., the radioactivity in two fractions from each well was measured. The first fraction was the culture supernatant, and the second was obtained by solubilizing the remaining islets in 100 μl of 2% SDS. The % $^{51}$Cr release for each well was calculated by the formula [(supernatant cpm)/(supernatant cpm+SDS lysate cpm)]×100. In turn, % specific lysis was calculated by subtracting the % $^{51}$Cr release from islets cultured in medium alone (i.e., spontaneous release) from the release by each well of islets cultured with a given number of T cells.

Cytotoxicity assays for screening of HPLC fractions and peptide libraries. AI4 CTL were generated by culturing splenocytes from NOD.AI4αβTg mice with IFN-γ-treated NIT-1 cells and 12.5 U/ml IL-2 as described (DiLorenzo et al., 2002). NY8.3 CTL were generated by culturing splenocytes from 8.3-NOD mice with mitomycin C-treated NOD splenocytes pulsed with 10 nM NRP-A7 peptide as described (DiLorenzo et al., 2002). CTL were used in 16 h $^{51}$Cr-release cytotoxicity assays to test for recognition of peptide-pulsed target cells at an E:T ratio of 40:1 as described (DiLorenzo et al., 2002). TAP-deficient cell lines RMA-S, RMA-S/K$^d$, T2, and T2-K$^d$ were used as targets. Synthetic peptides or peptide library mixes were used at concentrations indicated in the figures, and $1.6 \times 10^9$ NIT-1 cell equivalents of peptide were used for HPLC fraction screening assays.

H-2D$^b$ stabilization assay. RMA-S cells, cultured overnight at 28° C., were pulsed with peptides in DMEM medium with 10% FBS for 1 h at 28° C., incubated at 37° C. for 3 h, washed, stained with anti-H-2D$^b$ mAb 28-14-8, counterstained with FITC-conjugated polyclonal goat anti-mouse Ab (BD Biosciences Pharmingen, San Diego, Calif.), and analyzed by flow cytometry. Data were calculated by subtracting mean fluorescence intensity (MFI) of H-2D$^b$ on non-peptide-pulsed cells from that on peptide-pulsed cells.

Tetramer staining and flow cytometry. PE-conjugated MimA2/H-2D$^b$ tetramers were obtained through the NIMAD Tetramer Facility and titrated to determine optimal concentration. PE-conjugated NRP-V7/H-2K$^d$ and INS-L9/H-2K$^d$ tetramers were prepared as previously described (Trudeau et al., 2003). INS-L9 (LYLVCGERL) (SEQ ID NO:18) is the G9L variant of murine insulin B$_{15-23}$. FITC-conjugated anti-CD8α Ab was purchased from BD Biosciences Pharmingen (San Diego, Calif.). Cells were prepared to the appropriate cell density and incubated with tetramer and anti-CD8α Ab in 96-well V-bottom plates at 4° C. for 45 min. Samples were analyzed by flow cytometry using a FACS Calibur instrument and Cell Quest software (BD Biosciences Immunocytometry Systems, San Jose, Calif.). All samples were gated on live cells as determined by propidium iodide labeling.

ELISPOT assay. ELISPOT plates (MAHA S45 10; Millipore, Billerica, Mass.) were precoated with anti-murine IFN-γ Ab (R4-6A2; BD Biosciences Pharmingen, San Diego, Calif.) and blocked with 1% BSA (Fraction V, Sigma-Aldrich, St. Louis, Mo.) in PBS. APC (Mitomycin C-treated NOD splenocytes) were added at $2 \times 10^4$ cells/well and pulsed for 1 h with 1 μM of each peptide (MimA2, NRP-V7, INS-19, INS BC, GAD65$_{206}$, GAD65$_{546}$). Cultured islet T cells were added at $2 \times 10^4$ cells/well and plates were incubated at 37° C. for 40 h. IFN-γ secretion was detected with a second, biotinylated anti-murine IFN-γ Ab (XMG1.2; BD Biosciences Pharmingen, San Diego, Calif.). Spots were developed using streptavidin-alkaline phosphatase (Zymed Laboratories, Inc., South San Francisco, Calif.) and 5-bromo-4-chloro-3-indolyl-phosphate/nitroblue tetrazolium chloride substrate (Sigma-Aldrich, St. Louis, Mo.).

Results

AI4 T cells target a β cell peptide in the context of H-2D$^b$. AI4 was originally reported to be restricted to the MHC class I molecule H-2K$^d$ based on its cytotoxic activity against pancreatic islet cells from NOD-scid (expressing H-2K$^d$ and H-2D$^b$ class I MHC molecules) but not NOD.H2$^{nb1}$ mice (expressing H-2K$^b$ and H-2D$^b$) (DiLorenzo et al., 1998). We have previously shown that AI4 CTL recognize an NOD-derived β cell peptide distinct from those targeted by the other diabetogenic CD8 T cell clones 8.3 and G9C8 (DiLorenzo et al., 2002). This was done through mild acid stripping of the NOD-derived β cell line NIT-1, resulting in a mixture of β cell peptides eluted from both cell-surface H-2K$^d$ and H-2D$^b$ combined. In this earlier work, we then fractionated the peptides by HPLC and performed $^{51}$Cr-release cytotoxicity assays using target cells expressing both H-2D$^b$ and H-2K$^d$. However, in subsequent experiments, an epitope recognized by AI4 was surprisingly reconstituted using a target cell line lacking H-2K$^d$ expression but expressing H-2D$^b$ (TP DiLorenzo, unpublished observations).

In an attempt to resolve the apparent contradiction between the islet cytotoxicity and epitope reconstitution data, we next assayed peptides eluted separately from H-2K$^d$ and H-2D$^b$ molecules immunoaffinity-purified from NIT-1β cells (FIG. 1). The positive peak previously noted in HPLC fraction 22 of the acid-stripped combined peptide pool (DiLorenzo et al., 2002) was clearly reproduced when HPLC fractions of peptides purified from H-2D$^b$ (FIG. 1A), but not H-2K$^d$ (FIG. 1B), were assayed. A second active peak, possibly representing a modified version of the antigenic peptide detected in fractions 22 and 23, was also detected when the H-2D$^b$-eluted peptide fractions were examined (FIG. 1A). Thus, AI4 recognizes a peptide from NIT-1β cells in an H-2D$^b$-restricted fashion.

Figure 2:
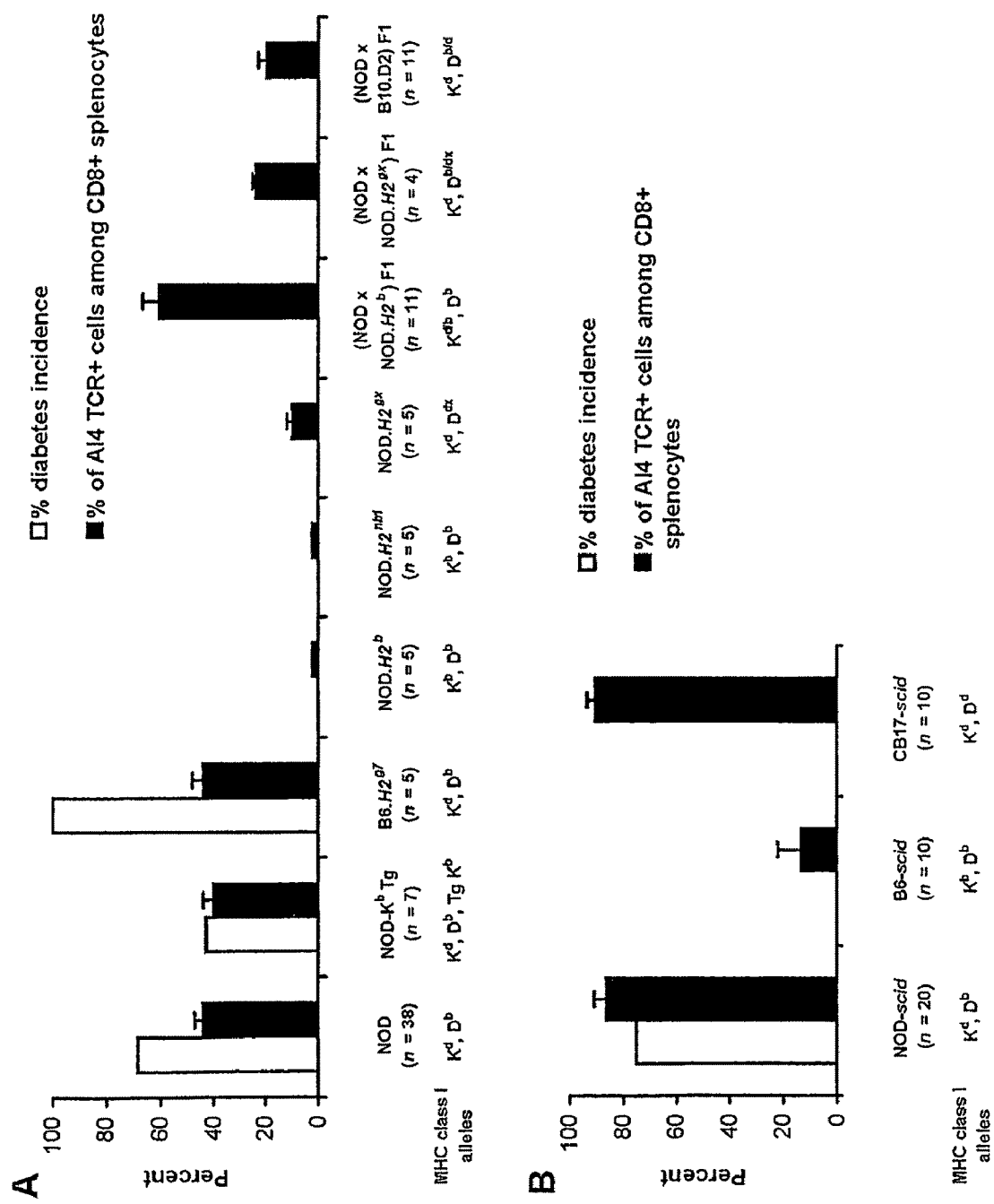
FIG. 2 is graphs of experimental results demonstrating that both H-2K$^d$ and H-2D$^b$ are required for recipient mice to develop diabetes after transfer of splenocytes from NOD.Rag1$^{null}$.AI4αβ Tg mice. Aliquots of 1×10$^7$ splenic leukocytes isolated from prediabetic female NOD.Rag1$^{null}$.AI4αβ Tg donors were injected intravenously into irradiated (700-750 rad) mice (A) or non-irradiated scid mice (B) as indicated. Recipient mice were monitored for diabetes development for up to 20 weeks after reconstitution. Recipient splenocytes were assessed for proportions of AI4 TCR-positive (Vα8) CD8+ T cells by costaining with Vα8- and CD8-specific antibodies at diabetes onset or at the end of the observation period.

Both H-2K$^d$ and H-2D$^b$ molecules are required for AI4 T cells to cause diabetes. To test whether AI4 CTL are also restricted to H-2D$^b$ in terms of their in vivo effector function, we employed a splenocyte transfer model of disease. Splenocytes were isolated from prediabetic female NOD.Rag1$^{null}$.AI4αβ Tg donors and transferred to a variety of mouse strains as indicated (FIG. 2). NOD.Rag1$^{null}$.AI4αβ Tg mice were used as the AI4 T cell source, because T cells from these mice can only express the transgenic AI4 TCR due to their inability to rearrange endogenous TCR genes. As expected, at 20 weeks post-transfer, the majority of standard NOD recipients had developed disease (FIG. 2A). Surprisingly, however, congenic strains expressing H-2D$^b$ in the absence of H-2K$^d$ (NOD.H2$^b$ and NOD.H2$^{nbl}$) remained disease-free, as did NOD.H2$^{gx}$ recipients, which express H-2K$^d$ in the absence of H-2D$^b$. Disease could only be transferred to recipients homozygously expressing both H-2K$^d$ and H-2D$^b$ (NOD, NOD-K$^b$ Tg and B6-H2$^{g7}$). Failure to transfer disease did not correlate with the overall genetic T1D resistance of the recipient strains. For example, 100% of the B6.H2$^{g7}$ recipients developed diabetes upon AI4 T cell transfer even though unmanipulated B6.H2$^{g7}$ mice are T1D-resistant. Also, although the NOD.H2$^{gx}$ strain is only partially genetically resistant to spontaneous diabetes, none of these recipients of AI4 T cells developed disease. Failure to transfer disease did not correlate with the presence of non-NOD class II MHC molecules, as the only class II molecule expressed by NOD.H2$^{gx}$ recipients is H-2A$^{g7}$, yet they did not develop disease upon AI4 transfer. The presence of the non-NOD class I MHC molecule H-2K$^b$ also cannot explain the failure to transfer disease to NOD.H2$^b$ and NOD.H2$^{nbl}$ recipients, as disease was efficiently transferred to the NOD-K$^b$ Tg strain.

Our finding that disease could only be transferred to recipients expressing both H-2K$^d$ and H-2D$^b$ is most consistent with the idea that efficient destruction of islets by AI4 requires recognition of two peptide/MHC complexes, one containing H-2D$^b$ and the other H-2K$^d$. Individually, each of the complexes is apparently of too low an abundance on the surface of 1 cells to trigger sufficient AI4 T cell activation for T1D development, but together they provide a sufficient antigenic stimulus for disease induction. To further explore this idea, we next transferred AI4 splenocytes to (NOD X NOD.H2$^b$) F$_1$, (NOD X NOD.H2$^{gx}$)F$_1$, or (NOD X B10.D2)F$_1$ recipients, all of which express both H-2K$^d$ and H-2D$^b$. However, all of the F$_1$ mice are heterozygous for either H-2K$^d$ or H-2D$^b$, thus presumably leading to a decrease in the abundance of the corresponding antigenic peptide/MHC complexes recognized by AI4. Interestingly, despite efficient AI4 T cell reconstitution, diabetes did not develop in any of the F$_1$ recipients. This finding is consistent with the hypothesis that the AI4 ligands are of low abundance, and that heterozygous expression of H-2K$^d$ or H-2D$^b$ reduces them to a level that is insufficient to lead to β cell elimination by AI4. This is consistent with the earlier suggestion that low-avidity interactions between T cells and 1 cells may not be pathogenic (Amrani et al., 2000).

Although NOD.H2$^{nbl}$, NOD.H2$^b$, and NOD.H2$^{gx}$ mice were poorly reconstituted with AI4 T cells (FIG. 2A), perhaps due to allogeneic rejection of the transferred cells, the splenocyte transfer data (taken in sum) suggested that both H-2K$^d$ and H-2D$^b$ are required for AI4 T cells to cause diabetes. However, to eliminate the possible complications of allogeneic rejection of the transferred AI4 cells or regulatory effects from recipient lymphocytes, we next did splenocyte transfers to scid recipients (FIG. 2B). Here again, no diabetes development was observed if either H-2K$^d$ or H-2D$^b$ were expressed alone. Unfortunately, however, B6-scid recipients were poorly reconstituted, perhaps due to NK cell-mediated rejection of the transferred cells or a requirement for H-2K$^d$ for homeostatic expansion (Jameson, 2002) by AI4 in this strain.

In an attempt to minimize the problems of poor reconstitution due to rejection or lack of expansion, we next employed a bone marrow transfer model of disease. Bone marrow from prediabetic female NOD.Rag1$^{null}$.AI4αβ Tg donors was reconstituted into lethally irradiated mice as indicated (Table 1). In all recipients, AI4 T cells represented at least 30% of CD8$^+$ splenocytes at the time of T1D development or at 20 weeks post-transfer. As before, diabetes development was only observed in recipients that homozygously expressed both H-2K$^d$ and H-2D$^b$. Note that heterozygous expression of H-2K$^d$ led to failure to transfer disease in (NOD X NOD.H2$^b$-Ab$^0$) F$_1$ mice, again supporting the idea that abundances of the AI4 ligands are low, and heterozygous expression results in an insufficient level of β cell destruction by AI4 for T1D to develop. Importantly, both NOD.H2$^b$-Ab$^0$ and (NOD X NOD.H2$^b$-Ab$^0$) F$_1$ recipients did not develop disease. This suggests that the presence of non-NOD MHC class II molecules in NOD.H2$^b$ and NOD.H2$^{nbl}$ mice is not responsible for the lack of disease development in these recipients.

TABLE 1

Both H-2K$^d$ and H-2D$^b$ are required for recipient mice to develop diabetes after transfer of bone marrow from NOD.Rag1$^{null}$.AI4αβ Tg mice

| Recipient | MHC class I alleles | MHC class II alleles | % diabetes incidence$^a$ (%) | % of AI4 TCR$^+$ cells among CD8$^+$ splenocytes$^b$ (% ± SEM) |
|---|---|---|---|---|
| NOD (n = 13) | K$^d$, D$^b$ | A$^{g7}$, E$^{null}$ | 53.8 | 49.0 ± 6.6 |
| NOD-K$^b$Tg (n = 8) | K$^d$, D$^b$, TgK$^b$ | A$^{g7}$, E$^{null}$ | 87.5 | 30.5 ± 5.0 |
| NOD.H2$^b$ (n = 7) | K$^b$, D$^b$ | A$^b$, E$^{null}$ | 0 | 75.2 ± 3.5 |
| NOD.H2$^{nbl}$ (n = 5) | K$^b$, D$^b$ | A$^{nbl}$, E$^k$ | 0 | 66.4 ± 0.71 |
| NOD.H2$^{gx}$ (n = 9) | K$^d$, D$^{dx}$ | A$^{g7}$, E$^{null}$ | 0 | 40.0 ± 6.9 |
| NOD.H2$^b$-Ab$^0$ (n = 4) | K$^b$, D$^b$ | A$^{null}$, E$^{null}$ | 0 | 77.4 ± 5.1 |
| (NOD × NOD.H2$^b$-Ab$^0$) F$_1$(n = 4) | K$^{d/b}$, D$^b$ | A$^{g7}$, E$^{null}$ | 0 | 70.2 ± 2.2 |

$^a$All recipient mice were followed for diabetes development for up to 20 weeks after bone marrow transfer.
$^b$Splenocytes were assessed for proportions of AI4 TCR-positive (Vα8) CD8 T cells by costaining with Vα8- and CD8-specific Abs at diabetes onset or at the end of the observation period (20 weeks after bone marrow transfer).

Figure 3:
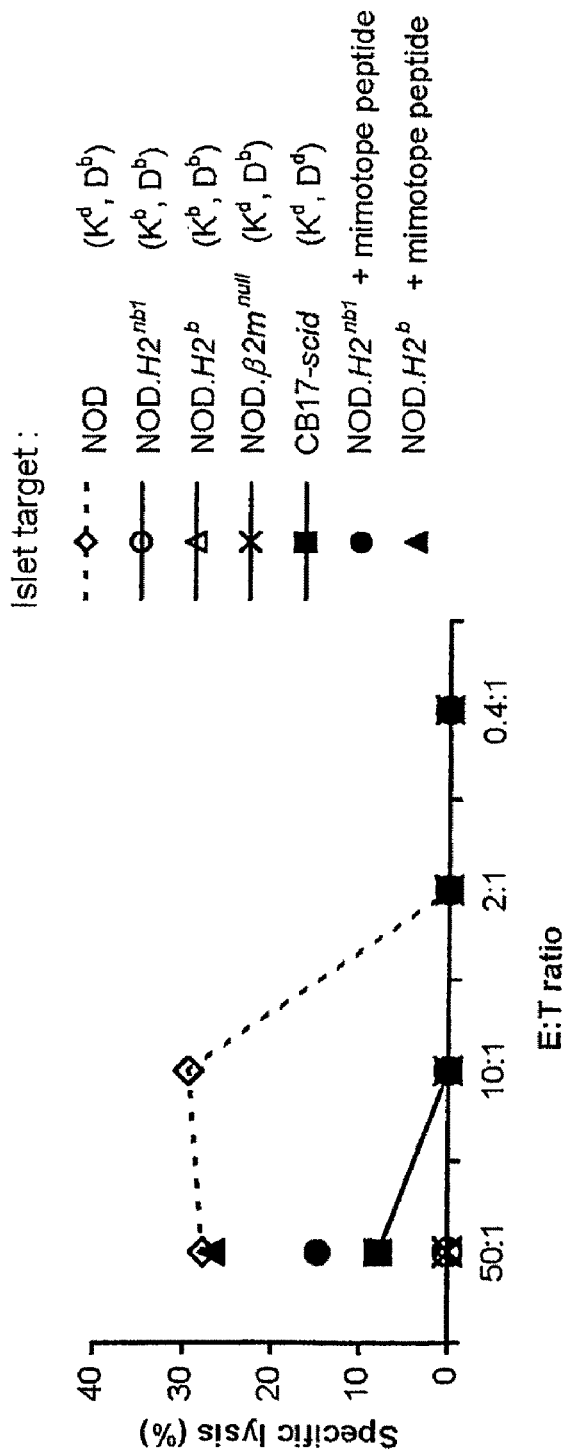
FIG. 3 is a graph of experimental results demonstrating that AI4 T cells only show in vitro cytotoxic responses to islets expressing both H-2K$^d$ and H-2D$^b$. Splenocytes from NOD.AI4αβ Tg mice were cultured for 72 hours in the presence of the AI4 mimotope peptide YFIENYLEL (SEQ ID NO:14) (10 nM) and 5 U/ml of IL-2. Effector AI4 T cells were seeded at the indicated E:T ratios into wells containing $^{51}$Cr-pulsed islets from the indicated mice. % specific lysis was determined as described in Example 1 Materials and Methods. Two single data points for the E:T ratio of 50 indicate cytotoxic responses to the NOD.H2$^{nb1}$ (●) and NOD.H$^{2b}$ (▲) islets pulsed with the mimotope peptide.

We also used in vitro islet-killing assays to examine more directly the MHC requirements for AI4 T cell recognition of β cells (FIG. 3). These experiments confirmed the necessity for both H-2K$^d$ and H-2D$^b$ expression on the β cell surface for efficient killing by AI4 T cells. Interestingly, if we added a mimotope peptide recognized by AI4 in the context of H-2D$^b$ (described below), AI4 T cells could efficiently kill islet β cells in the presence of only H-2D$^b$, indicating that these islets are not intrinsically resistant to CTL lysis.

AI4 T cells exhibit promiscuous peptide recognition behavior. Because our ongoing attempts to identify AI4's target antigen(s) by sequence analysis of peptides eluted from purified MHC or by cDNA expression cloning have not yet been successful, we used positional scanning synthetic combinatorial peptide libraries in order to identify mimotope peptides recognized by AI4 CTL. For T cells of unknown antigenic specificities, mimotope peptides have proven their utility. For example, mimotope peptides were used to demonstrate the importance of the diabetogenic 8.3-like T cell population even before IGRP was identified as its antigen (Amrani et al., 2000; Trudeau et al., 2003). Mimotope peptides can also be used to study thymic selection of specific T cells and may even help to identify natural peptide ligands.

We screened a peptide library designed to bind H-2D$^b$, namely, peptides of nine amino acids with anchors N at position 5 and L at position 9 (Falk et al., 1991). The library is composed of seven peptide sets (one for each non-anchor position), each containing 19 different peptide mixes. In each mix, one amino acid is fixed at a non-anchor position; thus, the 19 mixes in each set cover all natural amino acids (cysteine excluded) at the specified position. The six remaining, non-fixed positions in each mix are composed of equimolar amounts of the 19 amino acids under consideration. Using this positional scanning format, the potential contribution of each of the 19 amino acids to T cell recognition can be evaluated at each position of the peptide individually, and, ideally, a dominant amino acid can be identified for each non-anchor position (Blake et al., 1996). With three of the nine positions of the peptide fixed as single amino acids, and an equimolar mixture of the 19 amino acids at each of the other six positions, each peptide mix is composed of $19^6$, or $4.7 \times 10^7$, different peptides. A positive response to any one mix is likely due to T cell recognition of multiple peptides within that mix, and suggests that the fixed non-anchor amino acid in that mix is important for T cell recognition. Screening of our H-2D$^b$-binding peptide library in a $^{51}$Cr-release cytotoxicity assay with AI4 CTL and a total peptide concentration of 60 μg/ml per mix resulted in the activity profile shown in FIG. 4A. AI4 showed high reactivity to most amino acids fixed at positions 1, 2, 3, 7, and 8. When peptide position 6 was fixed, AI4 tolerated only large, hydrophobic amino acids with aromatic side chains (F, W, or Y). The AI4 response to amino acids fixed at position 4 was also somewhat restricted.

Figure 4:
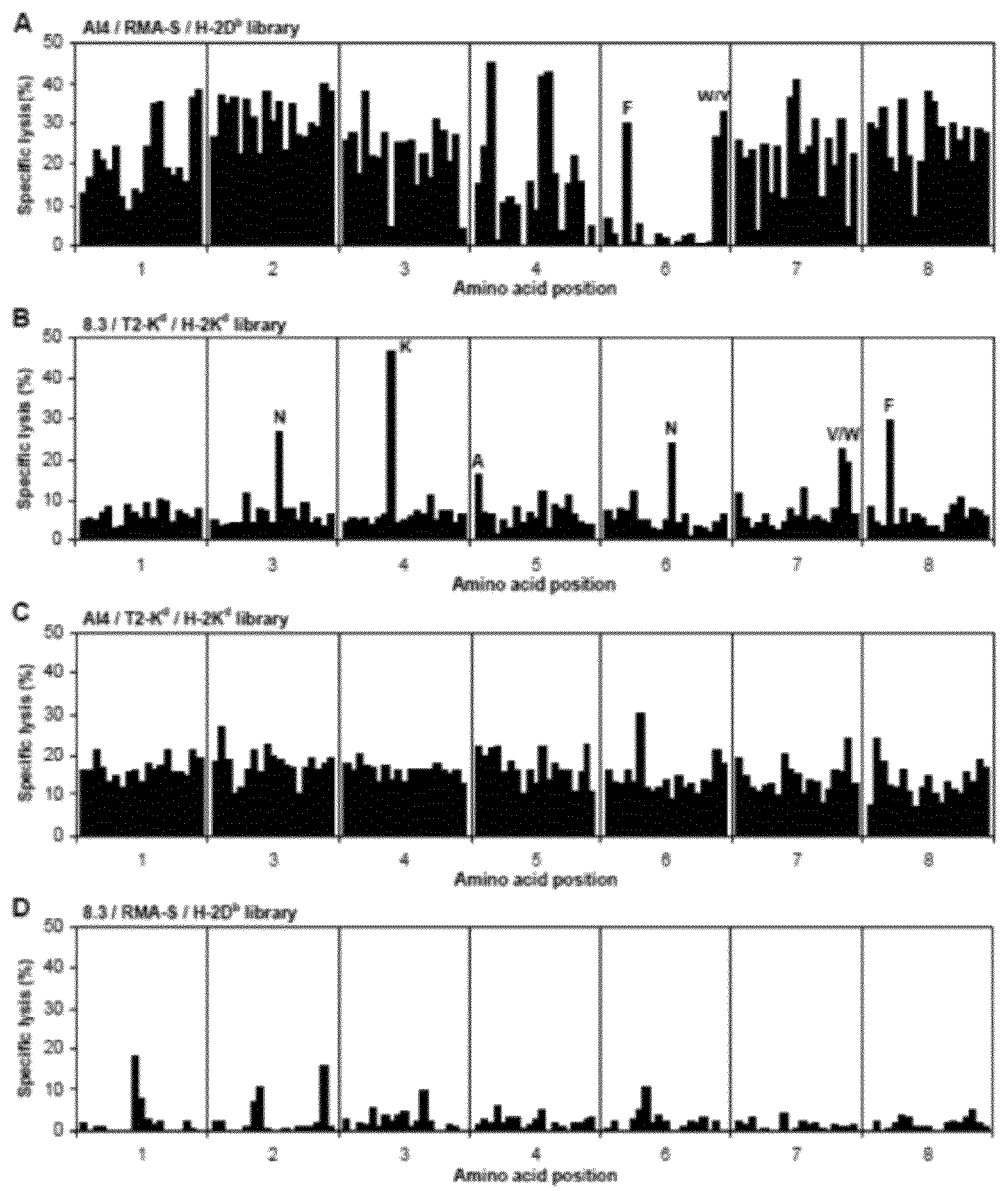
FIG. 4 is graphs of experimental results demonstrating that AI4 exhibits promiscuous peptide recognition behavior. AI4 (A) and 8.3 (D) cytotoxic responses towards RMA-S target cells pulsed with peptide mixes from the H-2D$^b$-binding peptide library. 8.3 (B) and AI4 (C) cytotoxic responses towards T2-K$^d$ target cells pulsed with peptide mixes from the H-2K$^d$-binding peptide library. Lysis of RMA-S by AI4 and 8.3 in the absence of peptide was 5.3% and 2.8%, respectively. Lysis of T2-K$^d$ by AI4 and 8.3 in the absence of peptide was 5.3% and 7%, respectively. For all panels, 19 different peptide mixes were tested for each amino acid position, and one amino acid was fixed at each non-anchor position in each mix (A, D, E, F, G, H, I, K, L, M, N, P, Q, R, S, T, V, W, and Y, in order from left to right). Each black bar represents the cytotoxic response toward the corresponding peptide mix. Peptide recognition was determined by $^{51}$Cr-release assay at an E:T ratio of 40. Letters in panels A and B denote the AI4- and 8.3-preferred amino acids at the indicated positions, based on those mixes eliciting the highest CTL responses. Each peptide mix was tested at a final total peptide concentration of 60 μg/ml. No lysis was observed when peptide pulsed-target cells were cultured in the absence of T cells.

The initial peptide concentration of 60 μg/ml was chosen based on previous peptide library screens such as was used to identify the mimotope peptide recognized by 8.3 CTL (Anderson et al., 1999). However, the library used in that study was designed slightly differently in that each fixed position consisted of an equimolar mix of two similar amino acids rather than an individual amino acid as in our library. To test whether the concentration was appropriate with our library design, we screened a peptide library designed to bind H-2K$^d$ (anchor residues fixed as Y at position 2 and L at position 9 (Falk et al., 1991)) with H-2K$^d$-restricted 8.3 CTL. This library was similar to our H-2D$^b$-binding peptide library except for the differences in fixed anchor residues. Upon screening this H-2K$^d$-binding peptide library with 8.3 CTL at a concentration of 60 μg/ml, we observed a dramatically different activity profile (FIG. 4B) than that seen when we screened the H-2D$^b$ library with AI4 CTL. Whereas AI4 responded to almost all mixes tested (FIG. 4A), the 8.3 response resulted in clear dominant amino acid contributions at six of seven positions tested, and the one position that did not show obvious dominance among the amino acids fixed at that position (position 1) resulted in a profile with no activity rather than with activity towards all mixes (FIG. 4B). In fact, only one or two mixes elicited clearly positive 8.3 lysis responses for positions 3, 4, 5, 6, 7, and 8. Importantly, our results agree with the sequences of the superagonist 8.3 mimotope NRP-V7 (KYNKANVFL) (SEQ ID NO:17) (Trudeau et al., 2003) and the original 8.3 mimotope NRP (KYNKANWFL) (SEQ ID NO:27) (Anderson et al., 1999) at all positions other than position 1.

Considering our splenocyte and bone marrow transfer data (FIG. 2 and Table 1), along with our in vitro islet-killing results (FIG. 3), all of which suggested that AI4 recognizes β cell peptides in the context of both H-2D$^b$ and H-2K$^d$, we next screened the H-2K$^d$-binding peptide library with AI4 CTL to independently test whether AI4 can interact with peptide/H-2K$^d$ complexes. The results showed that an AI4 response could indeed be elicited by H-2K$^d$-bound peptides (FIG. 4C) although, in this case, the responses were not as robust as those observed in the H-2D$^b$-binding peptide library screen (FIG. 4A). However, while not as robust as the H-2D$^b$-mediated responses, AI4 also responded to H-2K$^d$-bound peptides in a promiscuous fashion. For the sake of comparison, we also tested the H-2D$^b$-binding peptide library with 8.3 CTL, but we could not detect any reproducible significant responses in this screening (FIG. 4D). Taken together, these results indicate that AI4 is a promiscuous clonotype. While degeneracy in antigen recognition by TCRs is now well accepted (Hemmer et al., 1998; Sparbier and Walden, 1999), the extreme promiscuity demonstrated here by AI4 is clearly not characteristic of all autoreactive T cells, as diabetogenic 8.3 CTL exhibited a far more restricted response.

Figure 5:
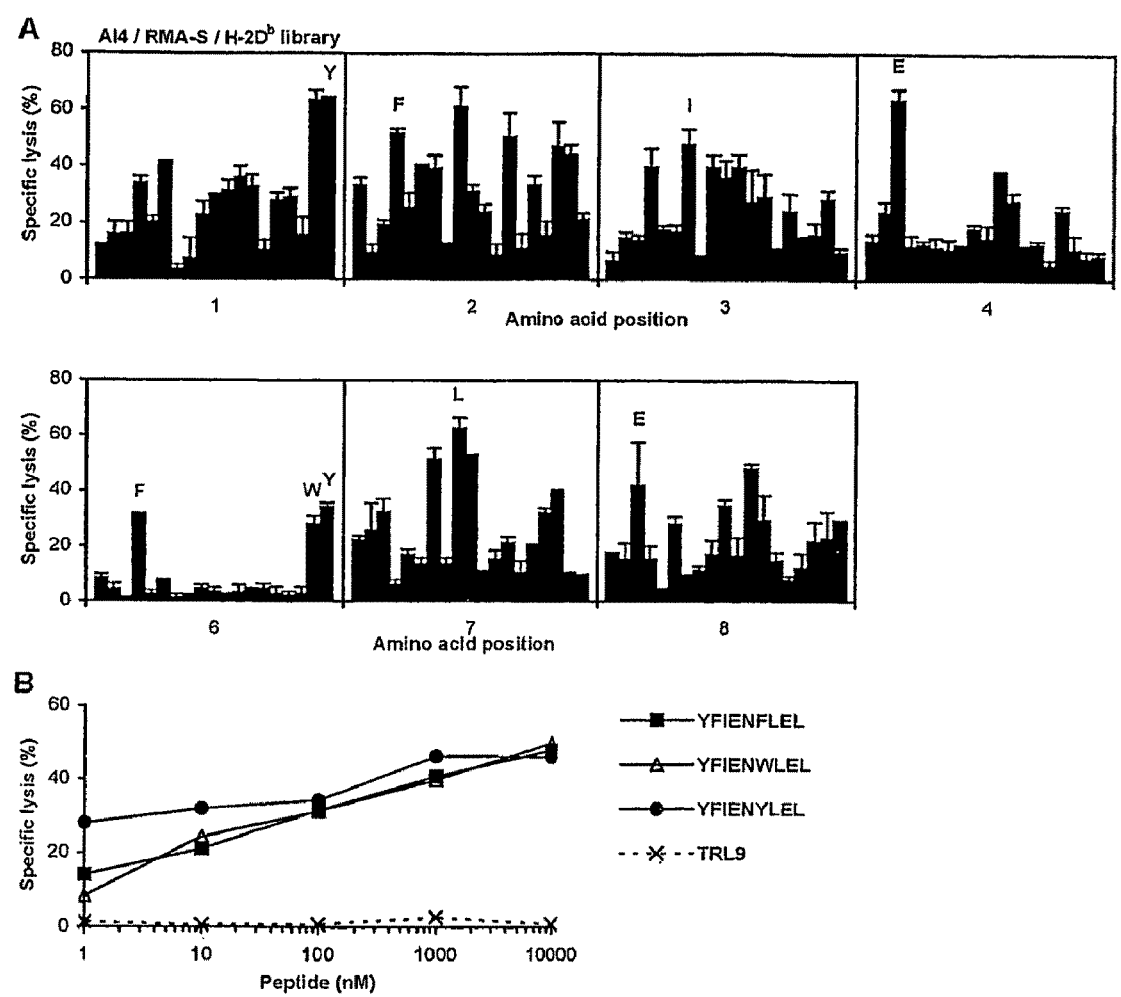
FIG. 5 is graphs of experimental results showing the identification of a mimotope peptide recognized by AI4 in the context of H-2D$^b$ A, AI4 cytotoxic response towards RMA-S target cells pulsed with peptide mixes from the H-2D$^b$-binding peptide library at a final total peptide concentration of 0.24 µg/ml. Lysis of target cells by AI4 in the absence of peptide was 7%. Nineteen different peptide mixes were tested for each amino acid position, and one amino acid was fixed at each non-anchor position in each mix (A, D, E, F, G, H, I, K, L, M, N, P, Q, R, S, T, V, W, and Y, in order from left to right). Each black bar represents the cytotoxic response toward the corresponding peptide mix. Peptide recognition was determined by $^{51}$Cr-release assay at an E:T ratio of 40. Letters denote amino acids chosen to be included in candidate mimotope peptides. B, AI4 cytotoxic response towards RMA-S target cells pulsed with varying concentrations of candidate mimotope peptides (SEQ ID NOS: 28, 29 and 14, respectively, top to bottom) or an H-2D$^b$-binding, negative control peptide (TRL9). The cytotoxic activity of the T cells was determined by $^{51}$Cr-release assay at an E:T ratio of 40.

Identification of mimotope peptides recognized by AI4 CTL in the context of H-2D$^b$. Since our data suggested that AI4 recognizes a NIT-1β cell peptide in the context of H-2D$^b$ (FIG. 1A), we continued to screen the H-2D$^b$-binding peptide library to identify a mimotope peptide recognized by AI4. To do this, we reduced the peptide concentration by 250-fold dilution (0.24 μg/ml) compared to the initial screen (60 μg/ml). Even at this greatly reduced concentration (FIG. 5A), the AI4 response was still more broad than that seen when 8.3 CTL were used to screen the H-2K$^d$ library at 60 μg/ml (FIG. 4B). Despite the lack of single dominant amino acids for each position, however, this screen did result in a smaller set of AI4-preferred amino acids at each position compared to the initial screen. Again, AI4 demonstrated a clear preference for F, W, or Y at position 6 (FIG. 5A). In addition, E was dominant at position 4 (FIG. 5A). To choose amino acids for each of the other non-anchor positions to include in our candidate mimotope peptides, we considered reproducibility among the top responders in multiple screens. However, we avoided combinations of residues that would result in highly hydrophobic peptides, as their lack of solubility in culture medium would make them difficult to assay. Using these criteria, three mimotope peptide candidates, differing only at position 6, were chosen: YFIENFLEL (SEQ ID NO:28), YFIENWLEL (SEQ ID NO:29), and YFIENYLEL (SEQ ID NO:14). These peptides were synthesized and tested for recognition by AI4 CTL (FIG. 5B). All peptides demonstrated dose-dependent recognition by AI4 compared to an irrelevant H-2D$^b$-binding peptide, TRL9 (TSPRNSTVL) (SEQ ID NO:26) (Zuberi et al., 1998). However, YFIENYLEL (SEQ ID NO:14) demonstrated the best response from AI4 CTL, as it elicited greater specific lysis at concentrations of 10 and 1 nM compared to the other candidate peptides. Thus, YFIENYLEL (SEQ ID NO:14) (Mim) is the most active AI4 mimotope peptide of the three examined. Recognition of Mim was restricted to H-2D$^b$, as AI4 did not lyse Mim-pulsed T2-K$^d$ cells (data not shown).

Figure 6:
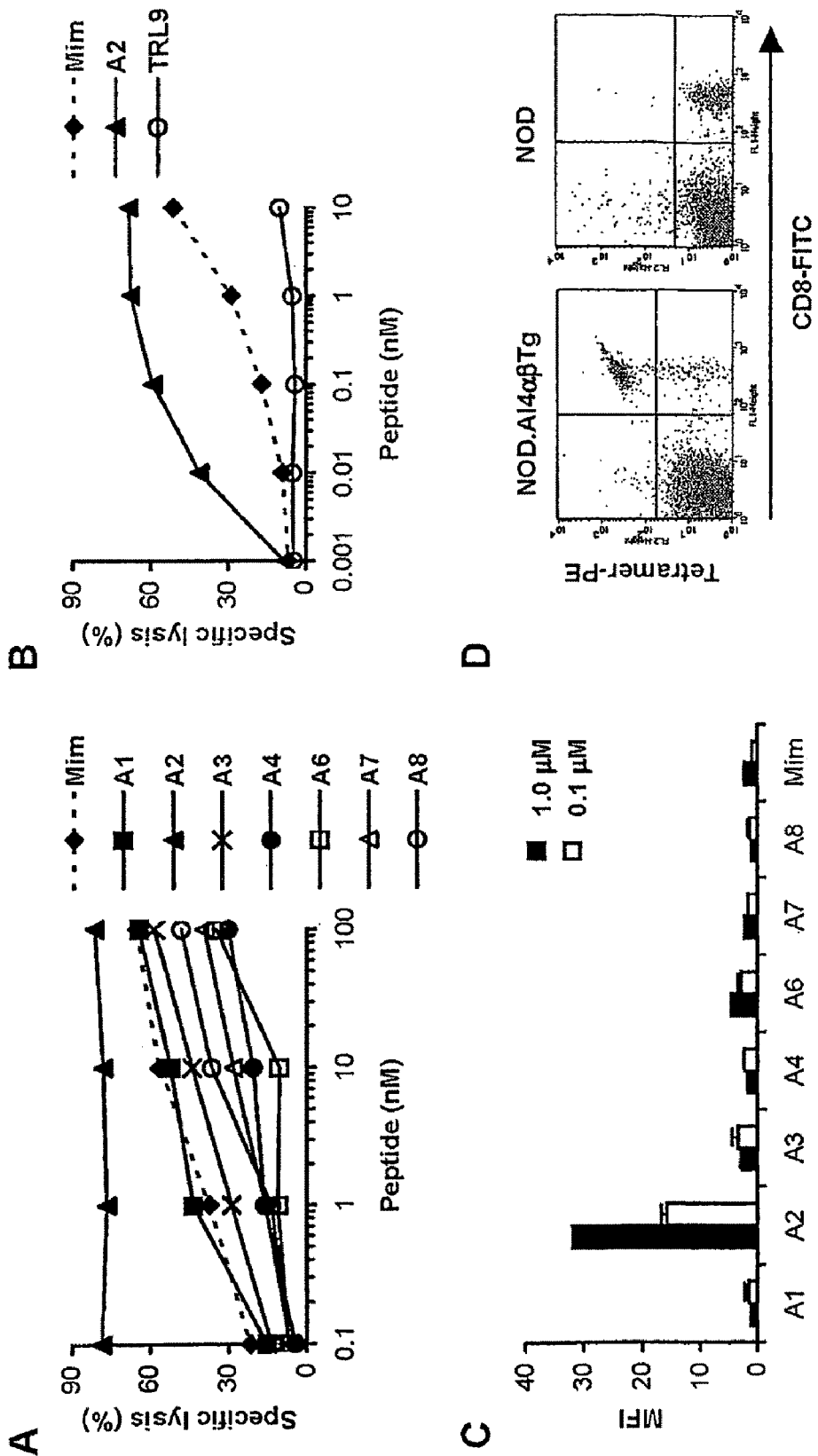
FIG. 6 is graphs of experimental results showing the identification and characterization of a superagonist mimotope peptide for AI4. A, AI4 cytotoxic response towards RMA-S target cells pulsed with varying concentrations of alanine-substituted mimotope peptides in which each amino acid of the original mimotope peptide (YFIENYLEL, Mim) (SEQ ID NO:14) was individually substituted with alanine. The cytotoxic activity of T cells was determined by $^{51}$Cr-release assay at an E:T ratio of 40. B, AI4 cytotoxic response towards RMA-S target cells pulsed with lower concentrations of the original mimotope peptide, the A2-substituted variant (YAIENYLEL, A2) (SEQ ID NO:13), or a negative control peptide (TRL9). C, H-2D$^b$ stabilization assay for the alanine-substituted mimotope peptides. RMA-S cells were pulsed with the indicated peptides, stained with an anti-H-2D$^b$ Ab, and analyzed by flow cytometry as described in Materials and Methods. Each bar represents mean fluorescence intensity (MF1). D, YAIENYLEL (SEQ ID NO:13)/H-2D$^b$ tetramer staining of AI4 T cells. Splenocytes were isolated from NOD.AI4αβ Tg or NOD mice, stained with FITC-conjugated anti-CD8 Ab and PE-conjugated YAIENYLEL (SEQ ID NO:13)/H-2D$^b$ tetramers, and analyzed by flow cytometry.

To better understand the contributions of each amino acid position within this AI4 mimotope peptide, we tested a set of alanine-substituted mimotope peptides (FIG. 6A). As expected, A substituted for Y at position 6 (designated A6 in the figure) and A substituted for E at position 4 (A4 in the figure) resulted in significantly lower responses compared to the original Mim peptide. Similarly, the responses towards A7- and A8-substituted peptides were decreased compared to the original Mim peptide response. Based on crystallographic data, amino acids at positions 4, 6, 7, and 8 of peptides bound to H-2D$^b$ are expected to point away from the MHC molecule and, thus, are expected to contact the TCR (Ostrov et al., 2002; Young et al., 1994). Strikingly, the A2 substitution resulted in a peptide that elicited a near maximal lysis response at all concentrations tested (as low as 0.1 nM). This response was confirmed to be dose-dependent upon screening lower concentrations, with half-maximal activity at a concentration of 10 pM (FIG. 6B). Position 2 is not expected to be a key TCR contact residue, so we hypothesized that alanine at position 2 allows for a more stable peptide-MHC interaction. To evaluate this possibility, we tested the ability of these alanine-substituted mimotope peptides, along with the original Mim peptide, to bind to H-2D$^b$ in an MHC stabilization assay. The A2-substituted mimotope peptide clearly demonstrated a much greater ability to stabilize H-2D$^b$ (FIG. 6C). It is possible that steric interactions involving the bulky F side chain at position 2 in the original and all other alanine-substituted mimotope peptides hindered their ability to bind MHC as tightly as the A2-substituted mimotope peptide. Interestingly, F appeared favored over A when the position 2 peptide mixes of the H-2D$^b$-binding peptide library were tested (FIGS. 4A and 5A). This suggests that the number of individual peptides recognized by AI4 within the mix where position 2 is fixed as A may be limited, whereas the number of peptides recognized by AI4 within the mix where position 2 is fixed as F may be higher.

Peptide/MHC tetramers composed of YAIENYLEL (SEQ ID NO:13)/H-2D$^b$ complexes were shown to specifically stain splenocytes from NOD.AI4αβTg mice, with minimal staining of nontransgenic NOD splenocytes (FIG. 6D). Thus, YAIENYLEL (SEQ ID NO:13) (MimA) is a superagonist mimotope peptide recognized by the diabetogenic AI4 T cell clone, and M-A/H-2D$^b$ tetramers may be used to detect AI4-like T cells.

Characterization of the AI4-like T cell population in NOD islet infiltrates. Until now, AI4 was only known to be present within the islet infiltrates of the one nondiabetic 5-week-old NOD mouse from which it was originally isolated (DiLorenzo et al., 1998). Whether the AI4 clonotype represents a population of T cells detectable in islet infiltrates of other NOD mice was unknown. The use of MimA2/H-2D$^b$ tetramers allowed us to address this issue. To do this, we cultured islets from four nondiabetic, 11-week-old female NOD mice for 7 days in the presence of 50 U/ml IL-2. The expanded T cells were stained with FITC-conjugated anti-CD8 antibody and PE-conjugated tetramers, and analyzed by flow cytometry. In addition to the MimA2/H-2D$^b$ tetramer, NRP-V7/H-2K$^d$ and INS-L9/H-2K$^d$ tetramers were included to detect the IGRP$_{206-214}$-reactive 8.3-like (Lieberman et al., 2003) and INS B$_{15-23}$-reactive G9C8-like CD8$^+$ T cell populations (Wong et al., 1999), respectively. Of the CD8$^+$ cells, 8% were stained with the MimA2/H-2D$^b$ tetramer, clearly indicating that AI4-like T cells constitute a detectable population in the islet infiltrates of NOD mice (FIG. 7A). In addition to the AI4-like T cells, IGRP-reactive T cells accounted for 41% of the CD8$^+$ cells, and insulin-reactive T cells accounted for 3%. Thus, >50% of the CD8$^+$ T cells are accounted for with these three antigenic specificities.

Detecting antigen specific CD8$^+$ T cell populations with peptide/MHC tetramers is a widely used method. However, it is important to know, in addition, if the tetramer positive cells are functional. We thus set out to determine if the tetramer positive CD8$^+$ cells isolated from NOD islets were able to produce IFN-γ in response to peptide. To do this, we incubated an aliquot of the same T cells used for the tetramer analysis in IFN-γ ELISPOT plates along with peptide-pulsed APC. Importantly, the ELISPOT data agreed with the tetramer staining (FIG. 7B). Spots were detectable in response to NRP-V7 (8.3-like T cells), MimA2 (AI4-like), and INS-L9 (G9C8-like). The relative numbers of spots detected for each of these were consistent with the tetramer staining data. No spots were detected in response to a second insulin peptide (INS BC), proposed to be a potentially important CD8$^+$ T cell epitope in NOD mice (Martinez et al., 2003), or to either of two H-2K$^d$-binding GAD65 peptides previously shown to be recognized by NOD splenocytes (Quinn et al., 2001). Thus, the pathogenic AI4-like, 8.3-like, and G9C8-like T cells detected in islet infiltrates with tetramers represent functional IFN-γ-producing CD8$^+$ T cell populations.

Preferred residues in H-2K$^d$-binding peptides recognized by AI4. We have defined an H-2D$^b$-binding AI4 mimotope peptide, but data presented above also suggested the existence of a peptide(s) recognized by AI4 in the context of H-2K$^d$ (FIGS. 2, 3, 4C and Table 1). Next we used a more elaborate screening of the H-2K$^d$-binding peptide library with AI4 CTL to obtain further evidence for the existence of such a peptide. For this H-2K$^d$ screening, we employed both T2 and T2-K$^d$ as APC to insure that responses seen to peptide-pulsed T2-K$^d$ cells were indeed dependent on this class I variant. At a 10-fold dilution (6 µg/ml) of the peptide concentration used for the initial screening depicted in FIG. 4C, it remained difficult to choose a dominant amino acid for each position using T2-K$^d$ as APC (FIG. 8A). However, now AI4 did demonstrate a preference for G, H, or W at position 6, and the recognition profile became more clear at positions 5, 7, and 8. In contrast, AI4 did not show any significant response when T2 cells were used as APC (FIG. 8B). Taken together, our results indicate that AI4 is a promiscuous clonotype capable of productively interacting with both H-2K$^d$ and H-2D$^b$ peptide/MHC complexes.

Discussion

Figure 7:
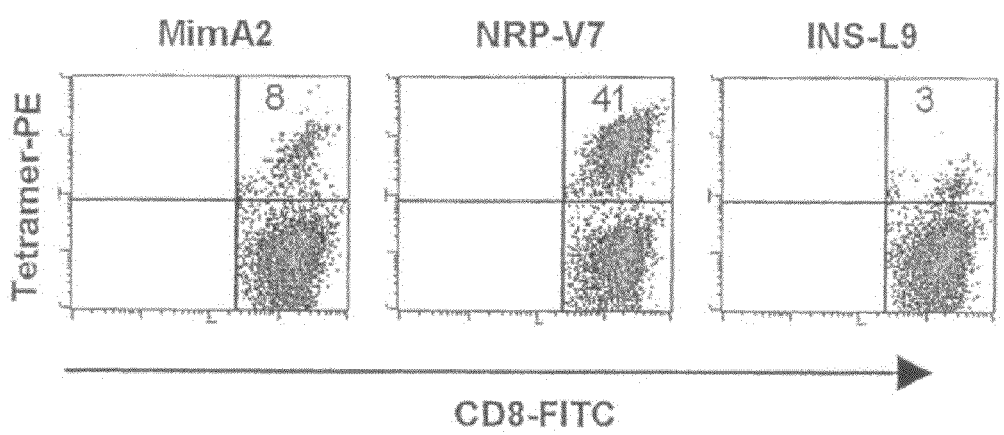
FIG. 7 is graphs and photographs of experimental results demonstrating that AI4-like T cells form a detectable population in cultured islet infiltrates from NOD mice. A, Profile of T cells cultured from pooled islets of 11-week-old NOD mice. Intact islets were isolated from four 11-week-old, non-diabetic, female NOD mice, pooled, cultured in the presence of 50 U/ml IL-2, stained with FITC-conjugated anti-CD8 Ab and PE-conjugated tetramer as indicated, and analyzed by flow cytometry. Samples are gated on CD8$^+$ cells, and numbers indicate percent of CD8$^+$ cells staining with the indicated tetramer. MimA2, YAIENYLEL (SEQ ID NO:13)/H-2D$^b$; NRP-V7, KYNKANVFL (SEQ ID NO:17)/H-2K$^d$; INS-L9, LYLVCGERL/H-2K$^d$ (SEQ ID NO:46). INS-L9 is the G9L variant of the insulin B$_{15-23}$ (LYLVCGERG) (SEQ ID NO:19) peptide. B, IFN-γ ELISPOT assay of T cells cultured from pooled islets of 11-week-old NOD mice. Mitomycin C-treated NOD splenocytes were seeded at 2×10$^4$/well into a 96-well ELISPOT plate and pulsed with 1 µM peptide as indicated. Cultured islet infiltrates were seeded at 2×10$^4$/well. Separate aliquots of the same islet culture were used in both A and B. After incubation at 37° C. for 40 h, the plate was developed as described in Materials and Methods. MimA2, YAIENYLEL (SEQ ID NO:13); NRP-V7, KYNKANVFL (SEQ ID NO:17); INS-I9, G9I variant of insulin B$_{15-23}$; INS-BC, insulin 2 B$_{25}$-C$_{34}$; GAD65$_{206}$, GAD65$_{206-214}$; GAD65$_{546}$, GAD65$_{546-554}$. Both INS-I9 and INS-L9 show more stable binding to H-2K$_d$ than insulin B$_{15-23}$ (Wong et al., 2002).
Figure 7:
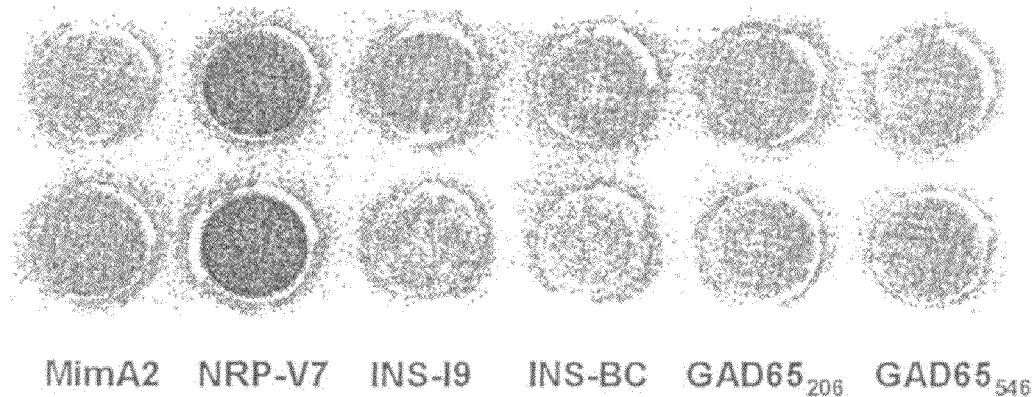

AI4 is one of a panel of β cell-autoreactive CD8$^+$ T cell clones that we previously isolated from the earliest insulitic lesions of young NOD mice (DiLorenzo et al., 1998). It is able to mediate β cell destruction sufficient to cause overt diabetes development even in the complete absence of CD4$^+$ T cell help or CD8$^+$ T cells of other antigenic specificities (Graser et al., 2000). Here we have shown, using ELISPOT and peptide/MHC tetramer analyses, that AI4 represents a clearly measurable population among islet-infiltrating T cells in NOD mice (FIG. 7).

We recently reported that the H-2A$^{nb1}$ and/or H-2E$^k$ class II MHC molecules encoded by the diabetes-protective H2$^{nb1}$ haplotype can mediate the negative selection of AI4 when expressed on bone marrow-derived APC, and that this clonotype is anergized when developing in the presence of H-2K$^b$ class I molecules (Serreze et al., 2004). Heterozygous expression of the H2$^q$ haplotype during AI4 T cell development results in reduced CD8 expression and functional impairment (Serreze et al., 2004). Thus, the AI4 TCR demonstrates remarkable promiscuity during T cell development. In this report, we have presented several independent lines of evidence indicating that mature AI4 CTL can interact with both H-2D$^b$ and H-2K$^d$, and that expression of both of these molecules is required for efficient recognition and destruction of islet β cells. Thus, the AI4 clonotype exhibits promiscuous behavior both during the selection process and while exerting its effector function.

Our results obtained using three different in vivo disease transfer models (Table 1, FIG. 2) all indicate that AI4 must interact with both an H-2D$^b$ and an H-2K$^d$ complex to efficiently destroy islet β cells. An alternative explanation for our disease transfer results is that non-NOD MHC molecules in certain of the recipients induced peripheral tolerance and rendered AI4 T cells unable to cause T1D. However, we do not favor this idea, as our in vitro islet cytotoxicity assays (FIG. 3), using AI4 CTL generated from NOD.Rag1$^{null}$.AI4αβ Tg mice, demonstrate that AI4 can only kill β cells that express both H-2K$^d$ and H-2D$^b$. Further, we previously reported that NOD-Rag1$^{null}$.AI4αβ Tg splenocytes are not stimulated in vitro by splenic APC from NOD.H2$^b$ or NOD.H2$^b$-Ab$^0$ mice (Serreze et al., 2004), suggesting that peripheral tolerance induction by the H2$^b$ or H2$^b$-Ab$^0$MHC haplotypes is unlikely.

Figure 8:
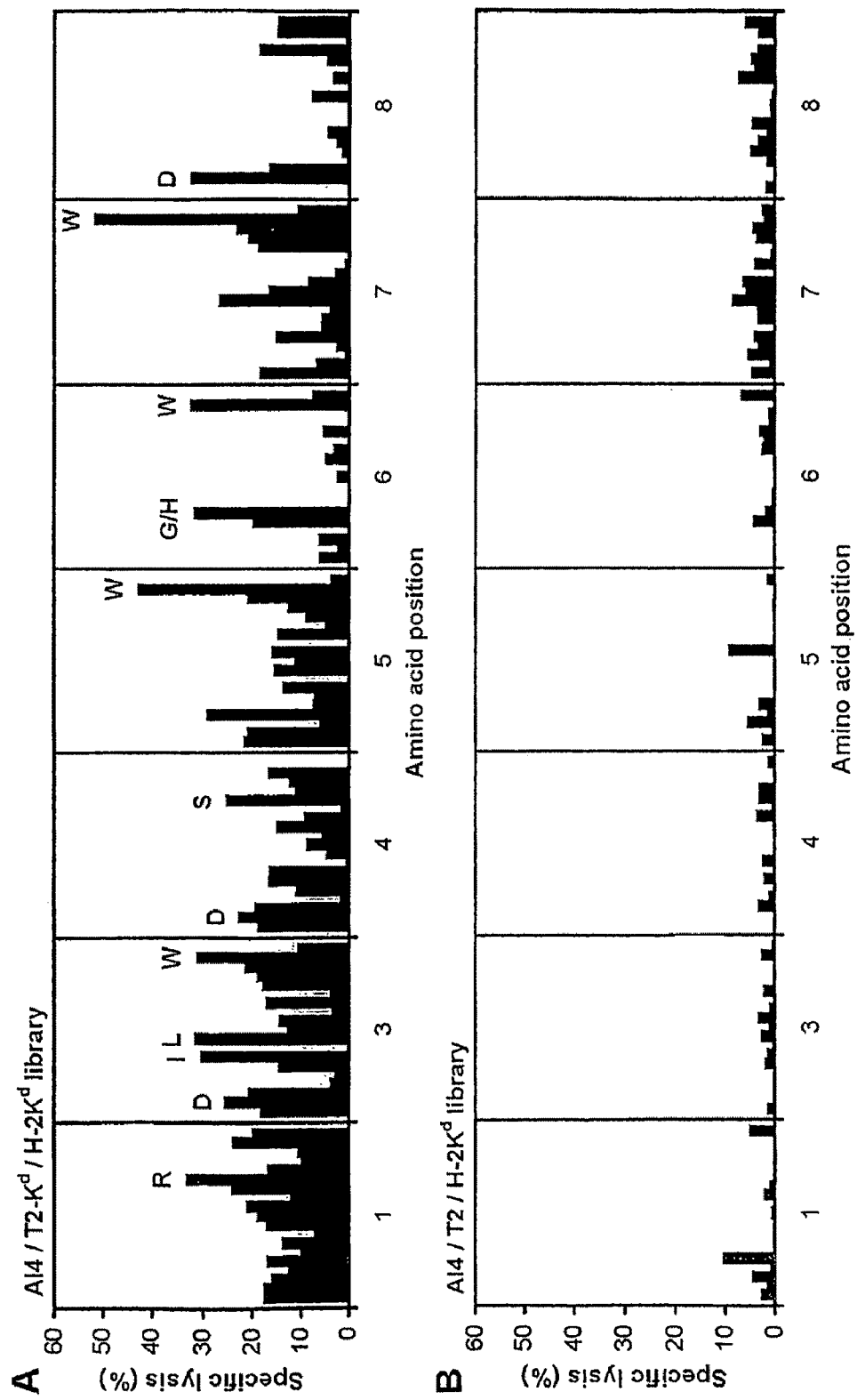
FIG. 8 is graphs of experimental results demonstrating that AI4 T cells can recognize peptides in the context of H-2K$^d$. AI4 cytotoxic responses towards T2-K$^d$ (A) or T2 (B) target cells pulsed with peptide mixes from the H-2K$^d$-binding peptide library at a final total peptide concentration of 6 µg/ml. Lysis of T2-K$^d$ and T2 cells by AI4 in the absence of peptide was 21.6% and 13.5%, respectively, and has been subtracted. Nineteen different peptide mixes were tested for each amino acid position, and one amino acid was fixed at each non-anchor position in each mix (A, D, E, F, G, H, I, K, L, M, N, P, Q, R, S, T, V, W, and Y, in order from left to right). Each black bar represents the cytotoxic response toward the corresponding peptide mix. Letters denote the AI4-preferred amino acids at the indicated positions based on those mixes eliciting the highest AI4 responses. No lysis was observed when peptide pulsed-target cells were cultured in the absence of T cells. The cytotoxic activity of T cells was determined by $^{51}$Cr-release assay at an E:T ratio of 40.

Our ability to detect a peak of activity when screening peptides eluted from purified H-2D$^b$ but not H-2K$^d$ molecules of NIT-1β cells (FIG. 1) is not necessarily at odds with our conclusion that AI4 must interact with both an H-2D$^b$ and an H-2K$^d$ complex to cause disease. The abundance of the antigenic peptide eluted from H-2K$^d$ molecules of NIT-1 cells might simply be too low to elicit an AI4 response in our assay system. Alternatively, the NIT-1 cell line might no longer express the β cell protein from which the antigenic H-2$^d$-binding peptide is derived, due to altered differentiation brought about by its transformation by SV40 T antigen (Hamaguchi et al., 1991) or repeated passage in culture. For example, expression of the β cell antigens recognized by two different diabetogenic CD4$^+$ T cell clones is rapidly lost from β cell adenoma cells upon growth in culture (Bergman and Haskins, 1994). Screening of the synthetic H-2K$^d$-binding peptide library clearly indicates that AI4 is able to productively interact with H-2K$^d$ complexes (FIGS. 4C and 8).

TCR crossreactivity or promiscuity (i.e., the ability of a single TCR to interact with more than one ligand) is now a well-documented phenomenon. The current understanding of the processes of T cell positive selection (Starr et al., 2003) and homeostasis (Jameson, 2002) indicates that some degree of crossreactivity is a requirement for T cell development and survival. In some cases, positive selection has been shown to be mediated by the same MHC molecule to which the T cell is restricted in terms of its recognition of a foreign peptide, but the selecting peptide is a different (self) peptide (Starr et al., 2003). Besides these and multiple other examples (Hemmer et al., 1998; Sparbier and Walden, 1999) of the ability of a TCR to recognize different peptides bound to the same MHC molecule, there are also examples of recognition of the same peptide presented by two different MHC molecules (Valmori et al., 1994; Tallquist and Pease, 1995; Oldstone et al., 1992; Shirai et al., 1993; Threlkeld et al., 1997; Ueno et al., 2002; Fleischhauer et al., 1996). In addition, the frequency of alloreactive T cells, which can respond to two different MHC molecules (one self and one not), is high (Lindahl and Wilson, 1977a; 1977b; Skinner and Marbrook, 1976. However, examples of recognition of two different peptides bound to two different self MHC molecules, as proposed here for AI4, are quite limited (Basu et al., 2000; Lang et al., 2002; Morgan et al., 2004). They include a recent report that negative selection of a particular CD8$^+$ T cell clonotype requires recognition of both an MHC class I and an MHC class II molecule (Morgan et al., 2004). Thus, there is some precedent, albeit limited, for our finding that AI4 can respond to β cell peptides bound to H-2D$^b$ as well as H-2K$^d$ self MHC molecules. We are not aware of any other example of a T cell that requires the simultaneous recognition of two different MHC molecules in order for its effector function to become apparent.

While the importance of CD8$^+$ T cells in T1D is becoming more widely recognized (Liblau et al., 2002), our knowledge of their antigenic specificities remains incomplete. Besides IGRP$_{206-214}$ and INS B$_{15-23}$, which are targeted by 8.3 and G9C8, respectively (Wong et al., 1999; Lieberman et al., 2003), no other natural peptide targets for islet-infiltrating CD8$^+$ T cells in NOD mice have been identified to date. Three other candidate peptides of potential relevance have previously been described (Martinet et al., 2003; Quinn et al., 2001). GAD65$_{206}$ and GAD65$_{546}$ have both been shown to bind H-2K$^d$ and to permit the generation of peptide-specific, IFN-γ-producing CTL from NOD splenocytes (Quinn et al., 2001). However, the ability of these GAD-reactive CD8$^+$ T cells to kill β cells was not evaluated. Compelling, though indirect, evidence for the importance of a third H-2K$^d$-binding peptide, INS BC, has also previously been provided (Martinez et al., 2003). Using T cells propagated from islet infiltrates and IFN-γ ELISPOT (FIG. 7B), we were unable to detect responses to GAD65$_{206}$, GAD65$_{546}$, or INS BC. However, we only tested T cells from a pool of islets from 11-week-old NOD mice, so it is still possible that these peptides are targets of islet-infiltrating T cells in mice of other ages. Our combined use of tetramers for the 8.3-, G9C8-, and AI4-like T cell populations has allowed us to account for greater than half of the CD8$^+$ T cells within cultured NOD islet infiltrates (FIG. 7A). Thus, IGRP, insulin, and AI4's antigen(s) clearly represent a considerable proportion of the antigens targeted by islet-infiltrating CD8$^+$ T cells, but additional specificities remain. Work is in progress to account for the balance of the CD8$^+$ T cells found within NOD islet infiltrates that cannot be individually enumerated and manipulated with the reagents currently available.

Example 2

Individual NOD Mice Exhibit Unique Patterns of CD8$^+$ T Cell Reactivity to Three Islet Antigens, Including the Newly Identified Widely Expressed Dystrophia Myotonica Kinase Example Summary Spontaneous autoimmune diabetes development in NOD mice requires both CD8$^+$ and CD4$^+$ T cells. Three pathogenic CD8$^+$ T cell populations (represented by the G9C8, 8.3, and AI4 clones) have been described. While the antigens for G9C8 and 8.3 are known to be insulin and islet-specific glucose-6-phosphatase catalytic subunit related-protein, respectively, only mimotope peptides had previously been identified for AI4. Here we used peptide/major histocompatibility complex tetramers to detect and quantify these three pathogenic populations among β cell-reactive T cells cultured from islets of individual NOD mice. Even within age-matched groups, each individual mouse exhibited a unique distribution of β cell-reactive CD8$^+$ T cells, both in terms of the number of tetramer-staining populations and the relative proportion of each population in the islet infiltrate. Thus, the inflammatory process in each individual follows its own distinctive course. Screening of a combinatorial peptide library in positional scanning format led to the identification of a peptide derived from dystrophia myotonica kinase (DMK) that is recognized by AI4-hike T cells. Importantly, the antigenic peptide is naturally processed and presented by DMK-transfected cells. DMK is a widely expressed protein that is nonetheless the target of a β cell-specific autoimmune response.

Introduction

Here we have used peptide/MHC tetramers to perform a detailed analysis of the three pathogenic CD8$^+$ T cell populations among T cells cultured from islets of individual NOD mice. Even within age-matched groups, individuals exhibited their own unique signature of β cell-specific autoreactivity. Thus, even within this inbred strain, spontaneous autoimmune responses show a variable developmental course.

Screening of a recombinant peptide library in positional scanning format, followed by pattern searches of the mouse protein database, revealed the unexpected finding that one target recognized by the AI4-like T cell population is a naturally processed and presented peptide from a protein that is not β cell-specific.

Materials and Methods

Mice. NOD/Lt mice were maintained by brother-sister mating. All NOD mice used for this work were bred at Albert Einstein College of Medicine; in this colony, 75% of females develop diabetes by 30 weeks of age. NOD.AI4αβ Tg mice, which transgenically express the TCR of the β cell-autoreactive CD8+ T cell clone AI4 (DiLorenzo et al., 1998), have been previously described (Graser et al., 2000). All mice were maintained under specific pathogen-free conditions and used in accordance with institutional guidelines for animal welfare.

Peptides. A positional scanning synthetic combinatorial peptide library (Borras et al., 2002) and the natural peptides listed in Table I were purchased from Mimotopes. Mim (YAIENYLEL) (SEQ ID NO:14), MimA2 (YAIENYLEL) (SEQ ID NO:13), GAD65$_{206-214}$ (murine glutamic acid decarboxylase 65$_{206-214}$; TYEIAPVFV) (SEQ ID NO:24) (Quinn et al., 2001), and TRL9 (TSPRNSTVL) (SEQ ID NO:26) peptides were synthesized by standard solid-phase methods using fluorenylmethoxycarbonyl chemistry in an automated peptide synthesizer (model 433A; Applied Biosystems) in the Laboratory for Macromolecular Analysis and Proteomics at Albert Einstein College of Medicine, and their identities were confirmed by mass spectrometry.

Islet T Cell Tetramer Analysis. Islet isolation by collagenase perfusion of the common bile duct was modified from a previously described protocol (Leiter, 1997). Briefly, the bile duct was cannulated and the pancreas perfused with collagenase P (Roche). The inflated pancreas was removed and incubated at 37° C. to digest exocrine tissue. Islets were washed and then resuspended in HBSS containing DNase I (Worthington Biochemical Corporation) and handpicked using a silanized micropipet. Isolated islets were resuspended in RPMI medium supplemented with 10% FBS (Hyclone) and 50 U/ml recombinant human IL-2 (PeproTech), and cultured intact in 24-well tissue culture plates (~50 islets/well) for 7-9 days.

PE-conjugated MimA2/H-2D$^b$ tetramers were obtained through the NIAID Tetramer Facility and titrated to determine optimal concentration. PE-conjugated NRP-V7/H-2K$^d$ and INS-L9/H-2K$^d$ tetramers were prepared as previously described (Amrani et al., 2000; Trudeau et al., 2003). MimA2 (YAIENYLEL) (SEQ ID NO:13) is a mimotope peptide recognized by AI4-like T cells (Takaki et al, 2003). NRP-V7 (KYNKANVFL) (SEQ ID NO:17) is a mimotope peptide recognized by 8.3-like T cells (Trudeau et al., 2003; Amrani et al., 2001). INS-L9 (LYLVCGERL) (SEQ ID NO:18) is the G9L variant of murine insulin B$_{15-23}$. INS-L9 shows more stable binding to H-2K$^d$ than insulin B$_{15-23S}$ but both are recognized by the G9C8 clone (Wong et al., 2002). FITC-conjugated anti-CD8α was purchased from BD Biosciences Pharmingen. Cells were incubated with tetramer and/or Ab in 96-well V-bottom plates at 4° C. for 45 min. Samples were analyzed by flow cytometry using a FACS Calibur instrument and Cell Quest software (BD Biosciences Immunocytometry Systems). All samples were gated on live cells as determined by propidium iodide labeling.

Cytotoxicity Assay. AI4 CTL were generated by culturing splenocytes from NOD.AI4αβ Tg mice with IFN-γ-treated NIT-1β cells (Hamaguchi et al., 1991) and IL-2 as described (DiLorenzo et al., 2002). CTL were used in 16 h $^{51}$Cr-release cytotoxicity assays to test for recognition of peptide-pulsed target cells at an effector to target ratio of 40:1 as described (DiLorenzo et al., 2002). TAP-deficient RMA-S cells (Kerre et al., 1986) were used as targets. Synthetic peptides or peptide library mixes were used at the concentrations indicated in the figures.

IFN-γ ELISPOT. ELISPOT plates (MAHA S45 10; Millipore) were coated with anti-murine IFN-γ Ab (R4-6A2; BD Biosciences Pharmingen) and blocked with 1% BSA (Sigma-Aldrich) in PBS. APC (Mitomycin C-treated NOD splenocytes) were added at $2\times10^4$ cells/well and pulsed with 1 μM peptide. Cultured islet T cells were added at $2\times10^4$ cells/well and plates were incubated at 37° C. for 40 h. Secreted IFN-γ was detected with a second, biotinylated anti-murine IFN-γ Ab (XMG1.2; BD Biosciences Pharmingen). Spots were developed using streptavidin-alkaline phosphatase (Zymed Laboratories) and 5-bromo-4-chloro-3-indolyl-phosphate/ nitroblue tetrazolium chloride substrate (Sigma-Aldrich). For all incubation steps, plate bottoms were covered with aluminum foil to distribute heat uniformly across the plate as described (Kalyuzhny and Stark, 2001).

RT-PCR and Molecular Cloning, Total RNA was isolated from IFN-γ-treated NIT-1β cells using the RNeasy Kit (Qiagen) and mRNA purified using the Oligotex mRNA Kit (Qiagen). First strand cDNA was synthesized using oligo(dT)$_{12-18}$ primers and M-MLV RT according to manufacturer's protocol (Invitrogen). For detection and cloning of full-length dystrophia myotonica kinase (DMK) cDNA (1.9 kb), sense (5'-AGCTTCCAACATGTCAGCCGAAGTG-3') (SEQ ID NO:30) and antisense (5'-GAATTCT-CAGGGGGCGAAGGTGG-3') (SEQ ID NO:31) primers containing HindRI and EcoRI restriction sites (italics), respectively, were used. For detection of full-length myotonic dystrophy kinase-related Cdc42-binding protein kinase β (MRCKβ) cDNA (5.6 kb), sense (5'-GCACCATGTCGGC-CAAGG-3') (SEQ ID NO:32) and antisense (5'-TCTATCTA-CAAACTGATTCTACAT-3') (SEQ ID NO:33) primers were used. cDNA was amplified using PfuTurbo hotstart DNA polymerase (Stratagene). For cloning of a 441 bp cDNA fragment of MRCKβ inclusive of exons 3 through 6, cDNA was amplified using KOD hotstart DNA polymerase (Novagen) and sense (5'-TTTGGTGAGGTTGCTGTTGTC-3') (SEQ ID NO:34) and antisense (5'-AGACTGAACAGT-GCCATCAT-3') (SEQ ID NO:35) primers corresponding to nt 259-279 and 699-680 of the murine MRCKβ. coding sequence, respectively.

For cloning of full-length DMK and the 441 bp fragment of MRCKβ, blunt-ended RT-PCR products were gel-purified using the QIAEX B Gel Extraction Kit (Qiagen) and ligated to the cloning vector pPCR-Script Amp SK(+) (Stratagene). The identities of the inserts were confirmed by sequencing at the DNA Sequencing Facility of the Albert Einstein College of Medicine. Full-length DMK cDNA was subsequently removed by HindIII/EcoRI digestion and transferred to the expression vector pcDNA3.1(+) (Invitrogen).

Transient Transfection. COS-7 cells were transfected, using a DEAE-dextran protocol (Karttunen et al., 1992), with varying concentrations of DMK/pcDNA3.1(+) and 10 ng/ml pcDNAI/H-2D$^b$ (generously provided by N. Shastri, University of California, Berkeley), with varying concentrations of pcDNA3.1(+) and 10 ng/ml pcDNAI/H-2D$^b$, or with varying concentrations of DMK/pcDNA3.1(+) alone. Separate cultures were transfected with pcDNAI/H-2D$^b$ alone and pulsed with varying concentrations of FNL9 (DMK$_{138-146}$) peptide as positive control (data not shown). Following co-culture with AI4 CTL, T cell response was measured as IFN-γ release by ELISA using capture (R4-6A2) and detecting (biotinylated XMG1.2) anti-murine IFN-γ Abs purchased from BD Biosciences Pharmingen. Plates were developed with streptavadin-conjugated horseradish peroxidase and 2,2'-azino-bis-[3-ethylbenzthiazoline-6-sulfonic acid] (Southern Biotechnology Associates).

Results

Figure 9:
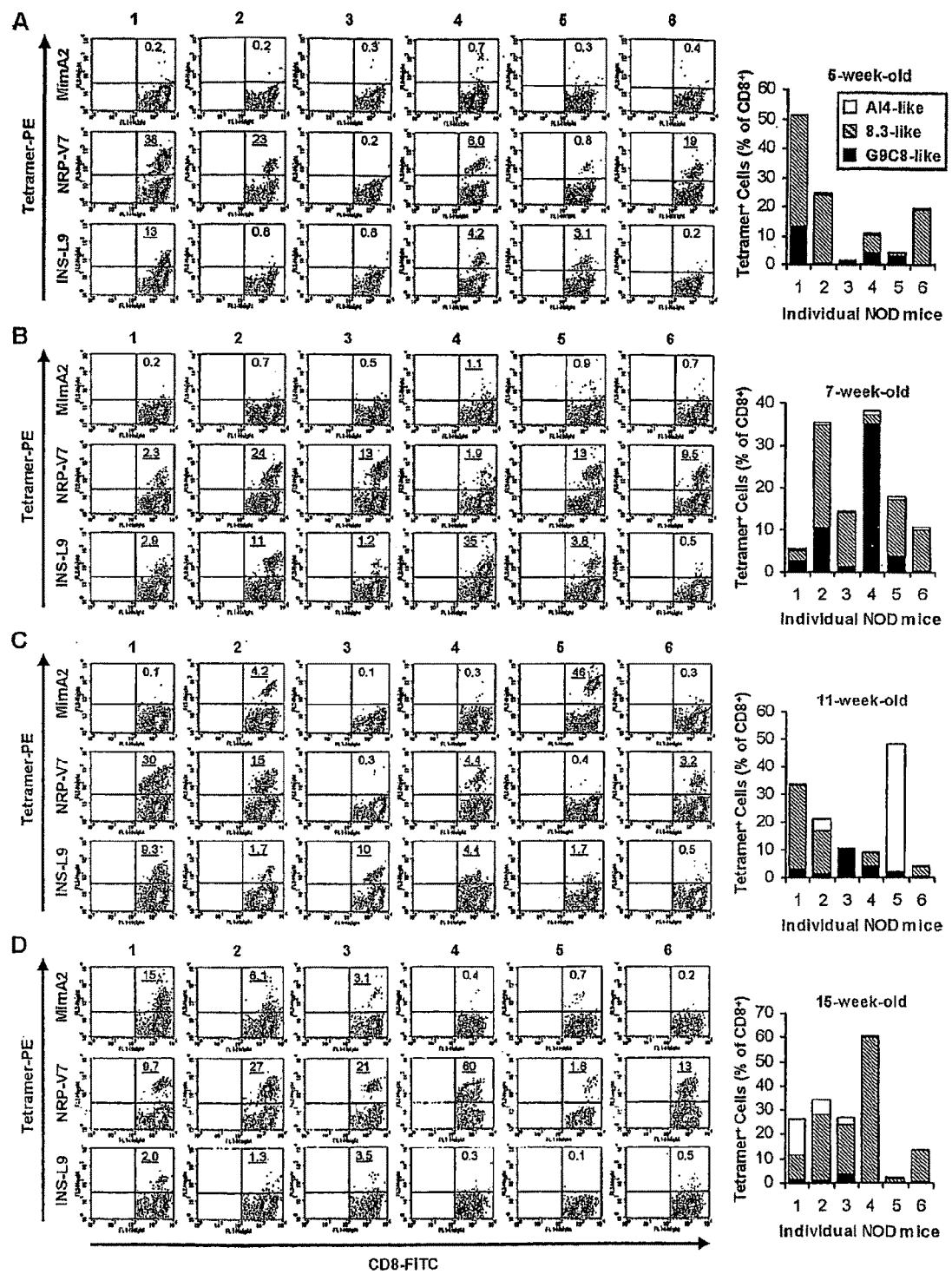
FIG. 9 is graphs of experimental results demonstrating that individual NOD mice exhibit distinct patterns of CD8$^+$ T cell reactivity to three islet antigens. Islets were isolated from individual female NOD mice and cultured in the presence of IL-2. The resulting cells were stained with FITC-anti-CD8 and PE-tetramer as indicated and analyzed by flow cytometry. Profiles of islet infiltrating T cells are shown for (A) 5-, (B) 7-, (C) 11-, and (D) 15-week-old mice. Each vertical set of three density plots represents staining of cells cultured from an individual mouse. All samples are gated on CD8$^+$ cells, and the numbers in each upper right quadrant represent percent of CD8$^+$ cells staining with the indicated tetramer. Underscores designate tetramer$^+$ populations (i.e., those representing ≧1% of CD8$^+$ cells). MimA2, YAIENYLEL (SEQ ID NO:13)/H-2D$^b$ tetramer (stains AI4-like T cells); NRP-V7, KYNKANVFL/H-2K$^d$ tetramer (SEQ ID NO:17) (stains 8.3-like T cells); INS-L9, LYLVCGERL/H-2K$^d$ tetramer (stains G9C8-like T cells) (SEQ ID NO:18). Graphical summaries of the flow cytometry data are presented at the right of each panel. The culture of intact islets has been reported to permit the expansion of β cell-autoreactive CD8$^+$ T cells (Amrani et al., 2000). This was verified in a preliminary experiment in which islets from four 11-week-old NOD mice were pooled in order to obtain sufficient numbers of cells to perform peptide/MHC tetramer analyses both directly ex vivo and after 7 days of culture. As expected, we observed an expansion of both the 8.3-like and AI4-like T cell populations from 4.5% and 1.7% of CD8$^+$ T cells on day 0 to 21% and 14% on day 7, respectively.

Analysis of the Pathogenic IGRP-reactive, Insulin-reactive, and AI4-like CD8+ T Cell Populations Cultured from NOD Islets. The incubation of intact islets from NOD mice in IL-2-supplemented medium allows for the expansion of β cell-autoreactive CD8+ T cells, as their cognate antigens are naturally present within the culture system (Amrani et al., 2000). This expansion allows sufficient numbers of cells to be obtained to permit reliable T cell analyses of individual mice. NRP-V7/H-2K$^d$ and INS-L9/H-2K$^d$ tetramers have previously been used to detect 8.3-like and G9C8-like T cells, respectively, in islet infiltrates (Lieberman et al., 2003; Trudeau et al., 2003). We recently identified a tetramer reagent (MimA2/H-2D$^b$) that can similarly be used to detect AI4-like T cells (Takaki et al., 2004). The tetramer reagents were used to characterize the relative proportions of these three known pathogenic CD8+ T cell populations at various prodromal stages of diabetes development (5-, 7-, 11-, and 15-weeks-old) in individual NOD mice. Islets from six non-diabetic, female NOD mice of each age were individually cultured in IL-2-supplemented medium. The expanded T cells from each culture were stained with FITC-conjugated anti-CD8 Ab and PE-conjugated tetramer, and analyzed by flow cytometry (FIG. 9). For these experiments, we defined tetramer staining populations accounting for ≧1% of the CD8+ cells as a tetramer+ population. In separate experiments, we have found that a tetramer staining population of this size invariably correlates with the detection of peptide-specific T cells using an IFN-γ ELISPOT assay (unpublished data).

With the exception of one of the 5-week-old animals, all mice had at least one tetramer+ T cell population. However, the percentages of CD8+ cells making up each of the tetramer+ populations varied from individual to individual. Further, nine mice had only one tetramer+ population, nine had two, and five had all three. The number of tetramer+ populations did not correlate with age. When all three tetramer+ populations were present, the majority population was most commonly 8.3-like. Among the nine mice that had two tetramer+ populations, most harbored both NRP-V7 and INS-L9 tetramer+ populations, although their relative proportions varied considerably among individual mice. Thus, individual NOD mice demonstrate high variability among their islet-infiltrative CD8+ T cell populations, both in terms of the number of tetramer+ populations and the relative proportions of each within the islet infiltrate. Individual patterns of autoimmune activity were also reflected in the total percent of CD8+ T cells that could be accounted for by the sum of the three known pathogenic populations. While other antigenic specificities exist among these infiltrates, the tetramer-staining profiles demonstrate that the G9C8-, 8.3-, and AI4-like T cell populations often account for a considerable proportion (up to 60%) of the CD8+ T cells infiltrating islets of NOD mice, and insulin, IGRP, and the antigen targeted by AI4 CTL are, therefore, of relevance to understanding disease pathogenesis.

Defining AI4-referred Amino Acids in TCR-contact Positions of H-2D$^b$-binding Peptides. Our efforts to characterize AI4's antigenic specificities by analysis of peptides eluted from MHC of NOD-derived β cells are ongoing. To complement this biochemical approach, we recently screened a recombinant peptide library in positional scanning format in order to identify the residues preferred by AM at each position of the peptide. This work led to the identification of the AI4 mimotope peptide YFIENYLEL (SEQ ID NO:14) (designated Mim) (Takaki et al., 2004; Serreze et al., 2004), and subsequent alanine substitution allowed the derivation of the superagonist peptide MimA2 (YAIENYLEL) (SEQ ID NO:13), which shows far superior binding to H-2D$^b$ and is recognized by AI4 at lower concentrations (Takaki et al., 2004). However, protein database searches using the mimotope sequences did not lead us to a natural counterpart.

Figure 10:
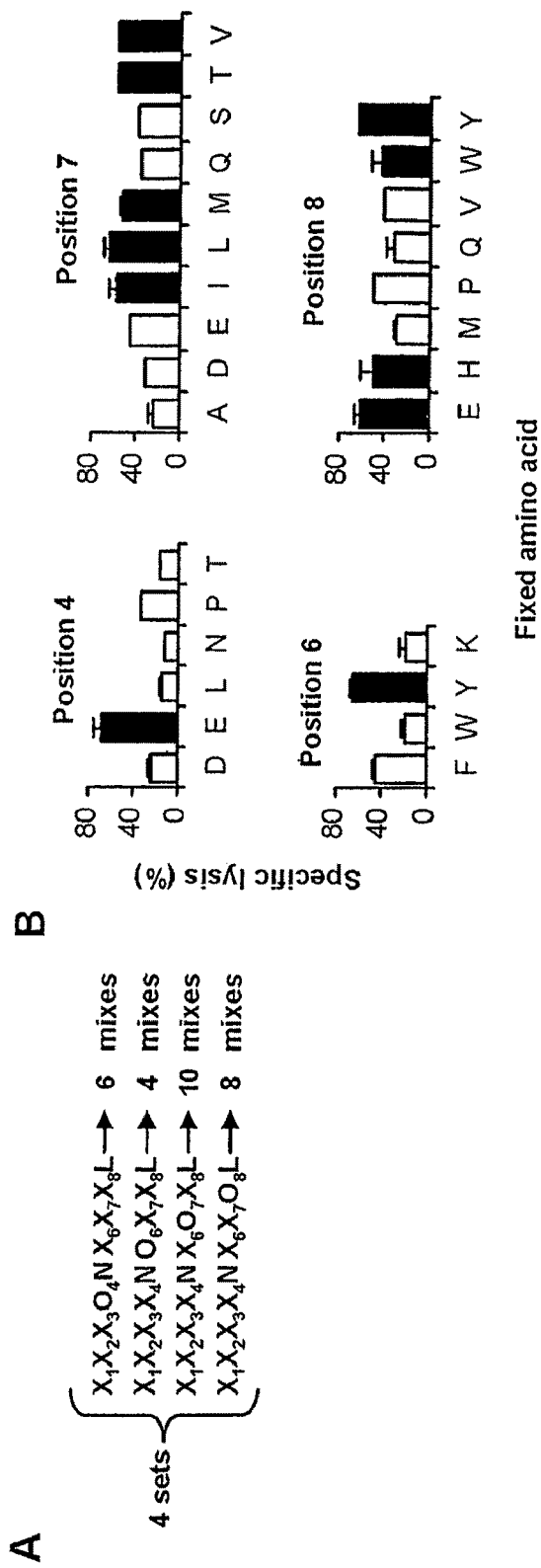
FIG. 10 is a schematic and graphs of experimental results defining AI4-preferred TCR contact residues of H-2D$^b$-binding peptides. (A) Schematic of the H-2D$^b$-binding peptide library consisting of 9-mers with fixed anchors N5 and L9. The library is composed of 4 sets, each defined by a fixed non-anchor position (O). Each set is composed of peptide mixes in which position O is fixed as one of the amino acids which previously elicited an AI4 response at that position as described in the text. Each non-fixed non-anchor position X consists of an equimolar mix of the amino acids that had previously elicited an AI4 response when fixed at that position. X$_1$ represents an equimolar mixture of F, H, L, M, N, P, Q, S, T, W, and Y; X$_2$ represents an equimolar mixture of A, F, G, H, I, L, M, N, Q, S, V, and W; and X$_3$ represents an equimolar mixture of F, I, L, M, N, P, Q, S, and W. O$_4$ was individually fixed as D, E, L, N, P, or T, and X$_4$ represents an equimolar mixture of these same amino acids. O$_6$ was individually fixed as F, W, Y (or K as a negative control, as K was found to not be tolerated at position 6 in our previous work), and $X_6$ represents an equimolar mixture of F, W, and Y. $O_7$ was individually fixed as A, D, E, I, L, M, Q, S, T, or V, and $X_7$ represents an equimolar mixture of these same amino acids. $O_8$ was individually fixed as E, H, M, P, Q, V, W, or Y, and $X_8$ represents an equimolar mixture of these same amino acids. (B) AI4 cytotoxic response towards RMA-S target cells pulsed with mixes from the H-2D$^b$-binding peptide library at a final concentration of 2 ng/ml. Based on this data and subsequent screens at different dilutions, we defined the AI4-preferred TCR-contact amino acids (black bars) to be E at position 4; Y at position 6; I, L, M, T, and V at position 7; and E, H, W, and Y at position 8.

The IGRP peptide targeted by 8.3-like T cells (VYLKT-NVFL) (SEQ ID NO:36) (Lieberman et al., 2003) is very similar in sequence to the superagonist 8.3 mimotope peptide NRP-V7 (KYNKANVFL) (SEQ ID NO:17) (Amrani et al., 2001). These peptides have the same amino acids at positions 2 and 9, the H-2K$^d$-binding anchor positions (Falk et al., 1991), and at positions 4, 6, 7, and 8, which are predicted to be important in TCR recognition of H-2K$^d$-binding peptides (Wong et al., 2002). Thus, to identify an AI4-targeted antigen, we sought to better characterize AI4-preferred amino acids at the TCR-contact positions of H-2D$^b$-binding peptides, i.e., positions 4, 6, 7, and 8 (Young et al., 1994). To identify the amino acids preferred by AI4 CTL, we designed a synthetic combinatorial peptide library composed of 9-mers with fixed H-2D$^b$ anchor residues N at position 5 and L at 9 (Falk et al., 1991). The library was composed of 4 sets of peptides (FIG. 2A), with each set consisting of multiple mixes in which a non-anchor position (0) was fixed. The amino acids utilized for the fixed positions were those that had elicited an AI4 response greater than the average for all nineteen amino acids (cysteine excluded) fixed at that position in the original library screen used to identify the Mim peptide (Takaki et al., 2004). All other non-anchor positions were similarly composed of equimolar mixes (X) of the amino acids that had previously elicited an AI4 response greater than the average for all nineteen amino acids fixed at that position. The AI4 lysis response elicited by each of the peptide mixes is shown in FIG. 10B. Based on this data and subsequent repeated screens at different dilutions, we defined the AI4-preferred TCR-contact amino acids of H-2D$^b$-bound peptides to be E at position 4; Y at position 6; I, L, M, T, and V at position 7; and E, H, W, and Y at position 8 (SEQ ID NO:37).

Identification of a Natural Peptide Recognized by AI4-like T Cells. To identify peptides found in murine proteins that might be recognized by AI4, we searched databases for proteins containing peptide sequences conforming to the pattern X-X-X-E-[NS]-Y-[ILMTV]-[EHWY]-[LM] (SEQ ID NO:37), where X is any of the twenty natural amino acids. The amino acids included for the TCR-contact positions 4, 6, 7, and 8 are based on the library screening data just described. H-2D$^b$-binding anchor residues N or S at position 5 and L or M at position 9 were included to restrict our search to H-2D$^b$-binding peptides (Falk et al., 1991; unpublished data). We used the pattern profile search algorithm ScanProsite (us.expasy.org/tools/scanprosite/) to search the Swiss-Prot and TrEMBL protein databases for nonamer peptides conforming to the AI4 preferred motif. The search was restricted to the taxon Mus musculus. The resulting peptides along with their protein source(s) are listed in Table 2.

TABLE 2

Natural Peptides with AI4-preferred TCR Contact Residues
(SEQ ID NOS: 38, 39, 40, 10, 11, 41, 42, 43, 44, 45, 55, 14, 13,
respectively, top to bottom and SEQ ID NO: 37 in the legend.

| Peptide Sequence | Peptide Abbrev. | Accession No. | Protein Source(s) |
|---|---|---|---|
| HEAESYML | HL9 | Q60755 | Calcitonin receptor precursor |
| FQDENYLYL | FNL9 | P54265 | Dystrophia myotonica kinase (DMK) |
|  |  | Q7TT50 | Mytonic dystrophy kinase-related Cdc42-binding protein kinase β (MRCKβ) |
| FTDESYLEL | FSL9 | P56960 | Polymyositis/scleroderma autoantigen 2 |
| RLFENYIEL | RIL9 | Q9D4H1 | Exocyst complex component Sec5 |
| QYLENYLWM | QM9 | P97871 | Aquarius |
| TNKENYTEL | TL9 | Q8C6H8 | Stromal cell derived factor receptor 1 |
| EVVESYMYL | EL9 | Q8K2N2 | Similar to 1,2-α-mannosidase IC (fragment) |
| RTSENYLEL | RLL9 | Q80TB9 | MKIAA1569 protein |
| VMLENYTHL | VML9 | Q8C1H3 | Similar to KRAB zinc finger protein |
| DMHENYMEM | DM9 | Q8BS74 | X-linked lymphocyte regulated complex |
| VTLENYTHL | VTL9 | AAH53084 | Hypothetical protein |
| YFIENYLEL | Mim |  | original AI4 mimotope |
| YAIENYLEL | MimA2 |  | A2-substituted AI4 mimotope |

This list contains the results of a ScanProsite search of Swiss-Prot and TrEMBL protein databases, limited to the taxon Mus musculus, for peptides with the AI4-preferred pattern: X-X-X-E-[NS]-Y-[ILMTV]-[EHWY]-[LM], where X represents any amino acid.

Figure 11:
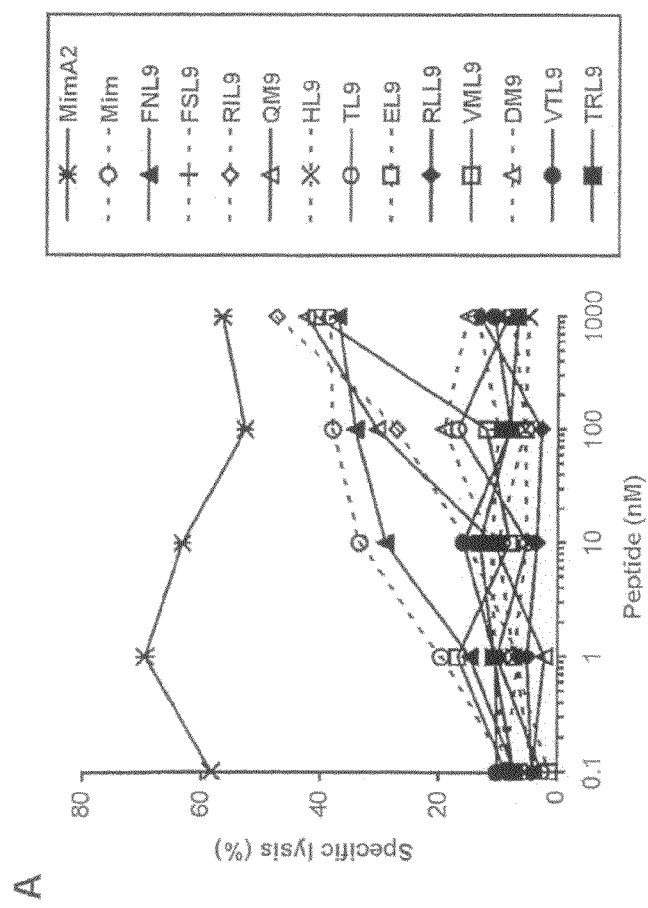
FIG. 11 is a graph and a photograph establishing the identification of a natural peptide recognized by AI4-like CTL. (A) AI4 cytotoxic response towards RMA-S target cells pulsed with varying concentrations of Mim, MimA2, natural peptides with AI4-preferred TCR contact residues (abbreviations as listed in Table 1), or an H-2D$^b$-binding negative control peptide (TRL9). (B) IFN-γ-release response of T cells cultured from NOD islets towards peptide-pulsed target cells. T cells cultured from islets pooled from four 11-week-old nondiabetic female NOD mice were incubated with target cells pulsed with the indicated peptides, and IFN-γ-release was measured by ELISPOT.

The natural peptides conforming to the AI4-preferred motif were tested for recognition by AI4 CTL at concentrations ranging from 0.1 nM to 1 μM. The majority of the peptides elicited no more of an AI4 response than the H-2D$^b$-binding, negative control peptide TRL9 (FIG. 11A). A minority of the peptides elicited an AI4 response at the highest concentrations tested. However, only one peptide (FNL9) elicited an AI4 response mirroring that obtained with the Mim peptide. The FNL9 peptide recognized by AI4 is found in two murine proteins, dystrophia myotonica kinase (DMK) (Jansen et al., 1992) and myotonic dystrophy kinase-related Cdc42-binding protein kinase β (MRCKβ) (Leung et al., 1998).

While these results were intriguing, it remained possible that recognition of the FNL9 peptide was unique to the AI4 clone and not representative of the AI4-like T cell population detectable in NOD islet infiltrates. To test whether the FNL9 peptide was recognized by the AI4-like T cell population, we assayed T cells cultured from NOD islets for their ability to secrete IFN-γ in response to peptide-pulsed target cells in an ELISPOT assay. As shown in FIG. 11B, FNL9 is indeed recognized by a detectable population of T cells cultured from the islets of NOD mice.

DMK is Expressed by β Cells and is Recognized by AI4 in an H-2D$^b$-restricted Manner. Neither DMK nor MRCKβ is β cell-specific, as both have been shown to be expressed in most tissues tested (Jansen et al., 1992; Leung et al., 1998; Moncrieff et al., 1999; Groenen and Wieringa, 1998). However, expression in pancreatic β cells has not been documented. We isolated mRNA from NOD-derived NIT-1β cells, since we know that these cells generate H-2D$^b$-bound peptides recognized by AI4 T cells (Takaki et al., 2004). By RT-PCR, we detected both DMK and MRCKβ expression (FIG. 12A). RT-PCR of NOD islet RNA confirmed that DMK and MRCKβ are also both expressed in islets (unpublished data). Sequencing of the appropriate regions of DMK and MRCKβ confirmed that, like the GenBank sequences (accession numbers NM_032418 and NM_183016, respectively), the NOD-derived cDNAs (SEQ ID NO:8) also encode the FNL9 peptide. The NOD DMK amino acid sequence is provided in as SEQ ID NO:1

We then transiently transfected COS-7 cells with varying concentrations of a full-length DMK expression construct, or vector alone, in combination with an H-2D$^b$ expression construct, co-cultured them with AI4 CTL, and monitored AI4 recognition by IFN-γ ELISA. Targets transfected with DMK, but not vector alone, elicited a dose-dependent AI4 CTL response (FIG. 12B). This recognition was H-2D$^b$-dependent, as DMK transfection without H-2D$^b$ resulted in no AI4 response. Thus, DMK represents a widely expressed protein, also expressed in β cells, which can be targeted by AI4 CTL.

Discussion

In NOD mice, three pathogenic β cell-autoreactive CD8$^+$ T cell clones have been identified (Nagata et al., 1994; Wong et al., 1996; Verdaguer et al., 1997; Utsugi et al., 1996; Graser et al., 2000. The G9C8 and 8.3 clones have previously been shown to represent detectable populations of CD8$^+$ T cells within islet infiltrates of NOD mice by peptide/MHC tetramer analysis (Wong et al., 1999; Lieberman et al., 2003; Amarani et al., 2000; Trudeau et al., 2003). We recently identified mimotope peptides recognized by AI4 CTL and used peptide/H-2D$^b$ tetramers to demonstrate that AI4-like T cells are also detectable in islet infiltrates (Takaki et al., 2004; Serreze et al., 2004). The simultaneous analysis of all three of these T cell populations within islet infiltrates of individual NOD mice has not previously been reported. Here we have found that, even within a given age group, the number of tetramer+ populations present within infiltrates from individual mice varied, as did the relative proportions of each of the tetramer+ populations (FIG. 9). Thus, individual NOD mice, even those of the same age, exhibit unique patterns of CD8+ T cell reactivity to β cell antigens. These findings may be due, in part, to the fact that development of diabetes in NOD mice is not completely synchronous. An alternative explanation is that several antigenic specificities may be responsible for the initiation and progression of β cell destruction, and that in any individual mouse the autoimmune response may be dominated by T cells recognizing any one of these antigens. Consistent with this idea is the finding that the 5-week-old mice, though all in the first stages of the insulitic process, nonetheless also demonstrated unique signatures of autoimmune activity. However, it is important to keep in mind that, based on the diabetes incidence in our NOD colony, approximately 25% of the individuals analyzed in FIG. 9 would not have developed diabetes by 30 weeks of age. Thus, we cannot say that all of the patterns of autoimmune activity depicted in FIG. 9 are necessarily pathogenic ones. In this regard, individual #5 in the 15-week-old group is of particular interest. Due to considerable islet destruction by 15 weeks of age, the average number of islets isolated per animal in this age group was 141±59 (compared to 238±26 for the 7-week-old group). However, mouse #5 yielded both the highest number of islets per individual (248) and the lowest number of T cells per islet among the 15-week-old group. These data suggest that this was most probably a diabetes-resistant animal. Importantly, it was only weakly positive for NRP-V7/H-2K$^d$ (<2% of CD8+ cells) and negative for both INS-L9/H-2K$^d$ and MimA2/H-2D$^b$. These observations further suggest the importance of the IGRP-, insulin-, and DMK-reactive T cell populations in the pathogenesis of diabetes in NOD mice.

Figure 12:
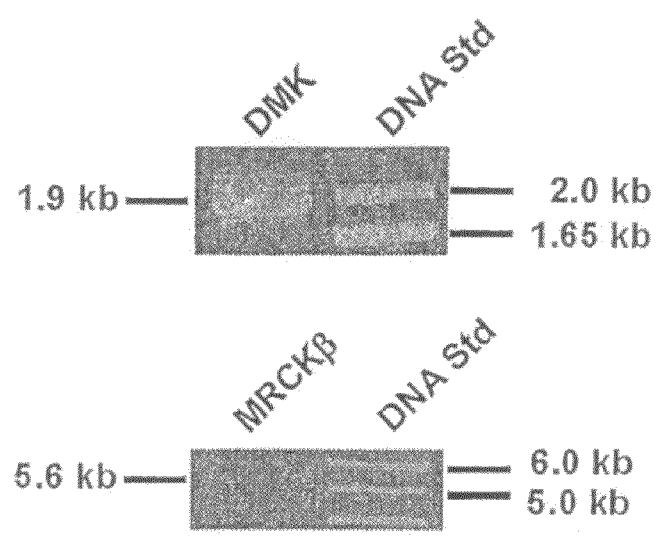
FIG. 12 is photographs of gels and a graph demonstrating that DMK is expressed in NIT-1β cells and recognized by AI4 CTL in an H-2D$^b$-restricted manner. (A) RT-PCR of mRNA purified from IFN-γ-treated NIT-1β cells was performed as described in Example 2 Materials and Methods, using primers designed to amplify full-length DMK (1.9 kb) and MRCKβ (5.6 kb) cDNA. DNA Std. 1 kb Plus DNA Ladder (Invitrogen). (B) COS-7 cells were transiently transfected with 10 ng/ml of an H-2D$^b$ expression construct (solid lines) along with varying concentrations of a DMK expression construct or vector alone, as indicated, and cultured with AI4 CTL. COS-7 cells transiently transfected with varying concentrations of a DMK expression construct but no MHC construct (broken line) were separately cultured with AI4 CTL. T cell response was measured as IFN-γ release by ELISA and is reported as absorbance at 405 nm (A405).
Figure 12:
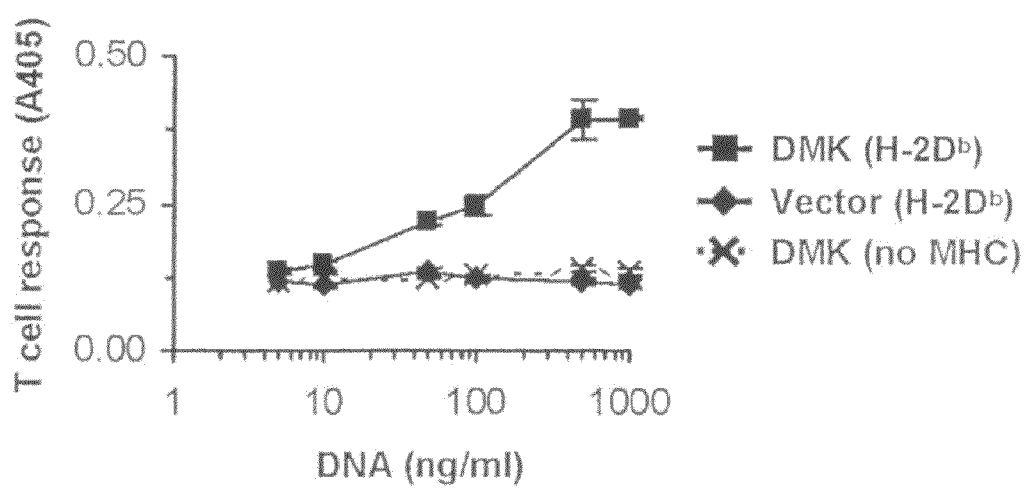

Our previous work indicated that AI4 targets two perhaps related, but as yet unidentified, NIT-1β cell peptides eluted from the class I MHC molecule H-2D$^b$ (Takaki et al., 2004). Here we have identified an H-2D$^b$-binding peptide (FNL9) that is recognized not only by the original AI4 T cell clone (FIG. 11A), but also by T cells cultured from the islets of NOD mice (FIG. 11B). In addition, we have demonstrated that DMK, which includes the FNL9 sequence and is expressed in both the NIT-1β cell line and in islets, is recognized by AI4 CTL in an H-2D$^b$-restricted manner (FIG. 12). We and our collaborators are currently employing a biochemical approach (Lieberman et al., 2003) to determine whether FNL9 is one of the peptides responsible for AI4 activity towards H-2D$^b$-eluted NIT-1β cell peptides.

DMK is a serine/threonine protein kinase expressed in most tissues examined (Jansen et al., 1992). The DMK gene is composed of 15 exons which give rise to multiple differentially spliced variants in humans and mice (Groenen et al., 2000). Intracellularly, DMK may be localized to the endoplasmic reticulum, cytosol, or mitochondria, depending on the splice variant expressed (Wansink et al., 2003). While the exact function of DMK is unknown, studies have demonstrated a variety of roles for the protein depending on the cell type examined (Reddy et al., 2002; Pall et al., 2003; Schulz et al., 2003; Jin et al., 2000). Prior interest in understanding the function of DMK stemmed from its putative role in myotonic dystrophy (Groenen and Wieringa, 1998). DMK has not previously been implicated as an autoantigen in NOD mice or in type 1 diabetes patients.

DMK does not represent the first β cell antigen targeted in diabetes that is expressed outside of β cells (Lieberman and DiLorenzo, 2003). For example, glutamic acid decarboxylase is expressed in several cell types in addition to β cells and is frequently targeted by autoantibodies in type 1 diabetes patients (Baekkeskov et al., 1990). Even widely expressed proteins have been implicated as autoantigens in certain organ-specific autoimmune diseases (O'Dwyer et al., 2002; Yeaman et al., 2000; Ishibashi et al., 2003; Ascherman et al., 2000; Dalakas and Hohlfeld, 2003; Corrigall and Panayi, 2002; Matsumoto et al., 1999). For example, the ubiquitously expressed protein glucose-6-phosphate isomerase has been identified as the target of pathogenic CD4+ T cells in mice developing a rheumatoid arthritis-like joint pathology (Matsumoto et al., 1999).

In NOD mice, a wave of physiological β cell death has been reported to occur at ~2 weeks of age, just prior to T cell activation in the pancreatic lymph nodes (PLN) and the first signs of insulitis, and has been implicated as a potential initiating event in diabetes development (Trudeau et al., 2000). In this scenario, apoptotic β cells are engulfed by dendritic cells in the pancreas and brought to the PLN where β cell antigens are then presented to T cells. This model is partly based on independent studies demonstrating that diabetogenic CD4+ (BDC2.5) or CD8+ (8.3) T cell clones proliferate in PLN during this time period (i.e., at ~3-4 weeks), but earlier responses can be detected if β cell apoptosis is induced by treatment with the β cell toxin streptozotocin (Turley et al., 2003; Zhang et al., 2002; Hoglund et al., 1999). Further, 8.3 proliferation in PLN was shown to occur normally in the absence of CTL-mediated β cell destruction, suggesting that the presentation of β cell antigens for the initial priming of autoreactive T cells may result from physiological β cell death rather than T cell-mediated β cell destruction (Yamanouchi et al., 2003). Interestingly, however, other studies have shown that the proliferation of β cell-reactive T cells in the PLN is, in some instances, an abortive tolerogenic, rather than a pathogenic, process (Kurts et al., 1999; Heath et al., 1998). This might explain the finding that the induction of limited β cell apoptosis can enhance the process of T cell tolerance induction in PLN (Hugues et al., 2002).

Though widely expressed, it is possible that a pathogenic autoimmune response to DMK occurs in the PLN, but not in other lymph nodes, due to β cell apoptosis. In support of this, B cells (and, thus, presumably T cells) recognizing the ubiquitously expressed autoantigen glucose-6-phosphate isomerase were recently reported to be initially activated only in the lymph nodes specifically draining the affected joints in a murine model of rheumatoid arthritis (Mandik-Nayak et al., 2002). T cells activated in certain secondary lymphoid organs, e.g., cutaneous or mesenteric lymph nodes, are instructed to express tissue-specific homing molecules, including adhesion molecules and chemokine receptors, that will cause the activated T cells to migrate preferentially to the skin or gut, respectively (Campbell and Butcher, 2002). If a similar process occurred in the PLN, and if DMK were only presented in the PLN, this could result in the migration of DMK-reactive T cells preferentially to the pancreas. Such a phenomenon would explain how a widely expressed antigen could be the target of a β cell-specific autoimmune response. While there is no published evidence suggesting that T cells activated in the PLN will preferentially home to the pancreas if their cognate antigen is also expressed elsewhere, this remains a formal possibility. Alternative explanations should also be considered. Perhaps due to tissue-specific differences in expression or turnover, the FNL9 peptide is only presented by β cells, but not other cell types, in sufficient quantities to allow for T cell recognition, though DMK is widely expressed. It is also possible that the combination of adhesion molecules and chemokines in the NOD islet environment preferentially attracts activated T cells to this site, including those that are FNL9-reactive, and for this reason, autoimmune destruction of other DMK-expressing tissues is not observed. Though NOD mice can mount autoimmune responses to a variety of restricted and ubiquitous proteins (Lieberman and DiLorenzo, 2003), overt autoimmune destruction is only observed in select organs (i.e., pancreas, thyroid, and salivary glands). However, cryptic autoimmune diseases can become manifest in NOD mice whose immune systems are manipulated in some way. For example, B7-2-deficient NOD mice are diabetes-resistant but instead develop spontaneous autoimmune peripheral polyneuropathy (Salomon et al., 2001). Though NOD mice have demonstrated immune responses to proteins expressed in neurons and Schwann cells, leading to damage of these cells in the vicinity of the islet (Saravia-Femandez, 1996; Winer et al., 2003), peripheral nerve damage has not been reported in standard NOD mice. Similarly, an early lethal $CD8^+$ T cell-mediated autoimmune myositis develops in NOD mice transgenically made Th1 cytokine-deficient (Serreze et al., 2003), though myositis is only rarely observed in non-transgenic NOD mice. Thus, for reasons that are still unclear, autoimmune activity is focused mainly on the islet in unmanipulated NOD mice, though some of the targeted antigens are expressed in Schwann cells or neurons or are ubiquitously expressed.

As DMK is highly expressed in muscle, it is tempting to speculate that the myositis observed in Th1 cytokine-deficient NOD mice is due to AI4-like T cells. If experimental evidence supports this notion, the AI4/myositis system would provide an excellent tool for better understanding why organ-specific disease occurs in the context of a loss of tolerance to widely expressed antigens.

In view of the above, it will be seen that the several advantages of the invention are achieved and other advantages attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. An isolated and purified oligopeptide or polypeptide comprising a sequence of less than 552 amino acids and comprising an amino acid sequence selected from the group consisting of XX(I/L)ENY(I/L)(E/Y)(L/M) (SEQ ID NO:56) and VMLENYTHL (SEQ ID NO:12), wherein if the sequence is VMLENYTHL (SEQ ID NO:12), then the oligopeptide or polypeptide is less than 51 amino acids.

2. The oligopeptide or polypeptide of claim 1, comprising the amino acid sequence YAIENYLEL (SEQ ID NO:13), VMLENYTHL (SEQ ID NO:12), or YFIENYLEL (SEQ ID NO:14).

3. An isolated and purified oligopeptide of 9-10 amino acids comprising FQDENYLYL (SEQ ID NO:9), RLFENYIEL (SEQ ID NO:10), or QYLENYLWM (SEQ ID NO:11).

4. The oligopeptide or polypeptide of claim 1, completely homologous to a mammalian DMK or MRCKβ polypeptide and having at least 90% homology to at least one of SEQ ID NO:1, SEQ ID NO:2, SEQ ID NO:3 or SEQ ID NO:4.

5. The oligopeptide or polypeptide of claim 1, wherein the oligopeptide or polypeptide comprises VMLENYTHL (SEQ ID NO:12) and comprises 13-25 amino acids.

6. The oligopeptide or polypeptide of claim 1, comprising 9-10 amino acids.

7. The oligopeptide or polypeptide of claim 1, further comprising an antigenic carrier.

8. The oligopeptide or polypeptide of claim 6, further comprising a detectable label.

9. The oligopeptide or polypeptide of claim 6, further comprising an MHC class I molecule that is capable of binding the oligopeptide.

10. The oligopeptide or polypeptide of claim 9, further comprising a cytotoxic molecule.

11. The oligopeptide or polypeptide of claim 5, further comprising an MHC class II molecule that is capable of binding the oligopeptide.

12. The oligopeptide or polypeptide of claim 11, further comprising a cytotoxic molecule.

13. An isolated and purified oligopeptide 9-10 amino acids in length, completely homologous with a mammalian MRCKβ, (SEQ ID NO:5) or a mammalian analog thereof, (SEQ ID NO:6) or a mammalian analog thereof, or (SEQ ID NO:7) or a mammalian analog thereof, and having at least 90% homology to at least one of SEQ ID NO:1, SEQ ID NO:3, or SEQ ID NO:4 wherein the oligopeptide is capable of binding an MHC class I molecule of the mammal.

14. The oligopeptide of claim 13, comprising the amino acid sequence XX(I/D/F/L)ENY(I/L)(E/W/Y)(L/M) (SEQ ID NO:16) or VMLENYTHL (SEQ ID NO:12).

15. The oligopeptide of claim 13, comprising an amino acid sequence selected from the group consisting of YAIENYLEL (SEQ ID NO:13), FQDENYLYL (SEQ ID NO:9), RLFENYIEL (SEQ ID NO:10), VMLENYTHL (SEQ ID NO:12), YFIENYLEL (SEQ ID NO:14), and QYLENYLWM (SEQ ID NO:11).

16. The oligopeptide of claim 13, further comprising a detectable label.

17. The oligopeptide of claim 13, further comprising an MHC class I molecule that is capable of binding the oligopeptide.

18. The oligopeptide of claim 17, further comprising a cytotoxic molecule.

19. A method of treating a mammal, wherein the mammal is at risk for or has type 1 diabetes, the method comprising administering an oligopeptide to the mammal in a manner sufficient to reduce $CD8^+$ T cells reactive to a DMK, an MRCKβ, a (SEQ ID NO:5) or analog thereof in the mammal, a (SEQ ID NO:6) or analog thereof in the mammal, or a (SEQ ID NO:7) or analog thereof in the mammal, wherein the oligopeptide is 9-10 amino acids in length, and comprises the amino acid sequence XX(I/D/F/L)ENY(I/L)(E/W/Y)(L/M) (SEQ ID NO:16) or VMLENYTHL (SEQ ID NO:12).

20. An isolated and purified oligopeptide or polypeptide comprising a sequence of less than 25 amino acids and comprising an amino acid sequence selected from the group consisting of XX(I/D/F/L)ENY(I/L)(E/W/Y)(L/M) (SEQ ID NO:16).

21. The isolated and purified oligopeptide or polypeptide of claim 20 comprising (Y/F)(F/A/Q)(I/D)ENYL(E/Y)L (SEQ ID NO:20).

22. The isolated and purified oligopeptide or polypeptide of claim 20 comprising (Y/F)(A/Q)(I/D)ENYL(E/Y)L (SEQ ID NO:22).

* * * * *

SEQUENCE LISTING

```
<160> NUMBER OF SEQ ID NOS: 56

<210> SEQ ID NO 1
<211> LENGTH: 631
<212> TYPE: PRT
<213> ORGANISM: Mus musculus

<400> SEQUENCE: 1

Met Ser Ala Glu Val Arg Leu Arg Gln Leu Gln Gln Leu Val Leu Asp
1               5                   10                  15

Pro Gly Phe Leu Gly Leu Glu Pro Leu Leu Asp Leu Leu Leu Gly Val
            20                  25                  30

His Gln Glu Leu Gly Ala Ser His Leu Ala Gln Asp Lys Tyr Val Ala
        35                  40                  45

Asp Phe Leu Gln Trp Val Glu Pro Ile Ala Ala Arg Leu Lys Glu Val
    50                  55                  60

Arg Leu Gln Arg Asp Asp Phe Glu Ile Leu Lys Val Ile Gly Arg Gly
65                  70                  75                  80

Ala Phe Ser Glu Val Ala Val Val Lys Met Lys Gln Thr Gly Gln Val
                85                  90                  95

Tyr Ala Met Lys Ile Met Asn Lys Trp Asp Met Leu Lys Arg Gly Glu
            100                 105                 110

Val Ser Cys Phe Arg Glu Glu Arg Asp Val Leu Val Lys Gly Asp Arg
        115                 120                 125

Arg Trp Ile Thr Gln Leu His Phe Ala Phe Gln Asp Glu Asn Tyr Leu
    130                 135                 140

Tyr Leu Val Met Glu Tyr Tyr Val Gly Gly Asp Leu Leu Thr Leu Leu
145                 150                 155                 160

Ser Lys Phe Gly Glu Arg Ile Pro Ala Glu Met Ala Arg Phe Tyr Leu
                165                 170                 175

Ala Glu Ile Val Met Ala Ile Asp Ser Val His Arg Leu Gly Tyr Val
            180                 185                 190
```

```
His Arg Asp Ile Lys Pro Asp Asn Ile Leu Leu Asp Arg Cys Gly His
            195                 200                 205
Ile Arg Leu Ala Asp Phe Gly Ser Cys Leu Lys Leu Gln Pro Asp Gly
210                 215                 220
Met Val Arg Ser Leu Val Ala Val Gly Thr Pro Asp Tyr Leu Ser Pro
225                 230                 235                 240
Glu Ile Leu Gln Ala Val Gly Gly Pro Gly Ala Gly Ser Tyr Gly
            245                 250                 255
Pro Glu Cys Asp Trp Trp Ala Leu Gly Val Phe Ala Tyr Glu Met Phe
            260                 265                 270
Tyr Gly Gln Thr Pro Phe Tyr Ala Asp Ser Thr Ala Glu Thr Tyr Ala
            275                 280                 285
Lys Ile Val His Tyr Arg Glu His Leu Ser Leu Pro Leu Ala Asp Thr
290                 295                 300
Val Val Pro Glu Glu Ala Gln Asp Leu Ile Arg Gly Leu Leu Cys Pro
305                 310                 315                 320
Ala Glu Ile Arg Leu Gly Arg Gly Gly Ala Gly Asp Phe Gln Lys His
            325                 330                 335
Pro Phe Phe Phe Gly Leu Asp Trp Glu Gly Leu Arg Asp Ser Val Pro
            340                 345                 350
Pro Phe Thr Pro Asp Phe Glu Gly Ala Thr Asp Thr Cys Asn Phe Asp
            355                 360                 365
Val Val Glu Asp Arg Leu Thr Ala Met Val Ser Gly Gly Glu Thr
370                 375                 380
Leu Ser Asp Met Gln Glu Asp Met Pro Leu Gly Val Arg Leu Pro Phe
385                 390                 395                 400
Val Gly Tyr Ser Tyr Cys Cys Met Ala Phe Arg Asp Asn Gln Val Pro
            405                 410                 415
Asp Pro Thr Pro Met Glu Leu Glu Ala Leu Gln Leu Pro Val Ser Asp
            420                 425                 430
Leu Gln Gly Leu Asp Leu Gln Pro Pro Val Ser Pro Pro Asp Gln Val
            435                 440                 445
Ala Glu Glu Ala Asp Leu Val Ala Val Pro Ala Pro Val Ala Glu Ala
            450                 455                 460
Glu Thr Thr Val Thr Leu Gln Gln Leu Gln Glu Ala Leu Glu Glu Glu
465                 470                 475                 480
Val Leu Thr Arg Gln Ser Leu Ser Arg Glu Leu Glu Ala Ile Arg Thr
            485                 490                 495
Ala Asn Gln Asn Phe Ser Ser Gln Leu Gln Glu Ala Glu Val Arg Asn
            500                 505                 510
Arg Asp Leu Glu Ala His Val Arg Gln Leu Gln Glu Arg Met Glu Met
            515                 520                 525
Leu Gln Ala Pro Gly Ala Ala Ala Ile Thr Gly Val Pro Ser Pro Arg
530                 535                 540
Ala Thr Asp Pro Pro Ser His Leu Asp Gly Pro Pro Ala Val Ala Val
545                 550                 555                 560
Gly Gln Cys Pro Leu Val Gly Pro Gly Pro Met His Arg Arg His Leu
            565                 570                 575
Leu Leu Pro Ala Arg Ile Pro Arg Pro Gly Leu Ser Glu Ala Arg Cys
            580                 585                 590
Leu Leu Leu Phe Ala Ala Ala Leu Ala Ala Ala Thr Leu Gly Cys
            595                 600                 605
Thr Gly Leu Val Ala Tyr Thr Gly Gly Leu Thr Pro Val Trp Cys Phe
610                 615                 620
```

```
Pro Gly Thr Thr Phe Ala Pro
625                 630

<210> SEQ ID NO 2
<211> LENGTH: 639
<212> TYPE: PRT
<213> ORGANISM: Homo sapiens

<400> SEQUENCE: 2

Met Gly Gly His Phe Trp Pro Glu Pro Tyr Thr Val Phe Met Trp
1               5                   10                  15

Gly Ser Pro Trp Glu Ala Asp Ser Pro Arg Val Lys Leu Arg Gly Arg
                20                  25                  30

Glu Lys Gly Arg Gln Thr Glu Gly Gly Ala Phe Pro Leu Val Ser Ser
            35                  40                  45

Ala Leu Ser Gly Asp Pro Arg Phe Phe Ser Pro Thr Thr Pro Pro Ala
    50                  55                  60

Glu Pro Ile Val Val Arg Leu Lys Glu Val Arg Leu Gln Arg Asp Asp
65                  70                  75                  80

Phe Glu Ile Leu Lys Val Ile Gly Arg Gly Ala Phe Ser Glu Val Ala
                85                  90                  95

Val Val Lys Met Lys Gln Thr Gly Gln Val Tyr Ala Met Lys Ile Met
            100                 105                 110

Asn Lys Trp Asp Met Leu Lys Arg Gly Glu Val Ser Cys Phe Arg Glu
        115                 120                 125

Glu Arg Asp Val Leu Val Asn Gly Asp Arg Arg Trp Ile Thr Gln Leu
130                 135                 140

His Phe Ala Phe Gln Asp Glu Asn Tyr Leu Tyr Leu Val Met Glu Tyr
145                 150                 155                 160

Tyr Val Gly Gly Asp Leu Leu Thr Leu Leu Ser Lys Phe Gly Glu Arg
                165                 170                 175

Ile Pro Ala Glu Met Ala Arg Phe Tyr Leu Ala Glu Ile Val Met Ala
            180                 185                 190

Ile Asp Ser Val His Arg Leu Gly Tyr Val His Arg Asp Ile Lys Pro
        195                 200                 205

Asp Asn Ile Leu Leu Asp Arg Cys Gly His Ile Arg Leu Ala Asp Phe
210                 215                 220

Gly Ser Cys Leu Lys Leu Arg Ala Asp Gly Thr Val Arg Ser Leu Val
225                 230                 235                 240

Ala Val Gly Thr Pro Asp Tyr Leu Ser Pro Glu Ile Leu Gln Ala Val
                245                 250                 255

Gly Gly Gly Pro Gly Thr Gly Ser Tyr Gly Pro Glu Cys Asp Trp Trp
            260                 265                 270

Ala Leu Gly Val Phe Ala Tyr Glu Met Phe Tyr Gly Gln Thr Pro Phe
        275                 280                 285

Tyr Ala Asp Ser Thr Ala Glu Thr Tyr Gly Lys Ile Val His Tyr Lys
290                 295                 300

Glu His Leu Ser Leu Pro Leu Val Asp Glu Gly Val Pro Glu Glu Ala
305                 310                 315                 320

Arg Asp Phe Ile Gln Arg Leu Leu Cys Pro Pro Glu Thr Arg Leu Gly
                325                 330                 335

Arg Gly Gly Ala Gly Asp Phe Arg Thr His Pro Phe Phe Gly Leu
            340                 345                 350

Asp Trp Asp Gly Leu Arg Asp Ser Val Pro Pro Phe Thr Pro Asp Phe
        355                 360                 365
```

```
Glu Gly Ala Thr Asp Thr Cys Asn Phe Asp Leu Val Glu Asp Gly Leu
    370                 375                 380

Thr Ala Met Val Ser Gly Gly Glu Thr Leu Ser Asp Ile Arg Glu
385                 390                 395                 400

Gly Ala Pro Leu Gly Val His Leu Pro Phe Val Gly Tyr Ser Tyr Ser
                405                 410                 415

Cys Met Ala Leu Arg Asp Ser Glu Val Pro Gly Pro Thr Pro Met Glu
                420                 425                 430

Val Glu Ala Glu Gln Leu Leu Glu Pro His Val Gln Ala Pro Ser Leu
            435                 440                 445

Glu Pro Ser Val Ser Pro Gln Asp Glu Thr Ala Glu Val Ala Val Pro
        450                 455                 460

Ala Ala Val Pro Ala Ala Glu Ala Glu Ala Glu Val Thr Leu Arg Glu
465                 470                 475                 480

Leu Gln Glu Ala Leu Glu Glu Glu Val Leu Thr Arg Gln Ser Leu Ser
                485                 490                 495

Arg Glu Met Glu Ala Ile Arg Thr Asp Asn Gln Asn Phe Ala Ser Gln
                500                 505                 510

Leu Arg Glu Ala Glu Ala Arg Asn Arg Asp Leu Glu Ala His Val Arg
            515                 520                 525

Gln Leu Gln Glu Arg Met Glu Leu Leu Gln Ala Glu Gly Ala Thr Ala
        530                 535                 540

Val Thr Gly Val Pro Ser Pro Arg Ala Thr Asp Pro Pro Ser His Leu
545                 550                 555                 560

Asp Gly Pro Pro Ala Val Ala Val Gly Gln Cys Pro Leu Val Gly Pro
                565                 570                 575

Gly Pro Met His Arg Arg His Leu Leu Leu Pro Ala Arg Val Pro Arg
                580                 585                 590

Pro Gly Leu Ser Glu Ala Leu Ser Leu Leu Phe Ala Val Val Leu
            595                 600                 605

Ser Arg Ala Ala Ala Leu Gly Cys Ile Gly Leu Val Ala His Ala Gly
        610                 615                 620

Gln Leu Thr Ala Val Trp Arg Arg Pro Gly Ala Ala Arg Ala Pro
625                 630                 635

<210> SEQ ID NO 3
<211> LENGTH: 1713
<212> TYPE: PRT
<213> ORGANISM: Mus musculus

<400> SEQUENCE: 3

Met Ser Ala Lys Val Arg Leu Lys Lys Leu Glu Gln Leu Leu Leu Asp
1               5                   10                  15

Gly Pro Trp Arg Asn Asp Ser Ala Leu Ser Val Glu Thr Leu Leu Asp
                20                  25                  30

Val Leu Val Cys Leu Tyr Thr Glu Cys Ser His Ser Ala Leu Arg Arg
            35                  40                  45

Asp Lys Tyr Val Ala Glu Phe Leu Glu Trp Ala Lys Pro Phe Thr Gln
        50                  55                  60

Leu Val Lys Asp Met Gln Leu His Arg Glu Asp Phe Glu Ile Ile Lys
65                  70                  75                  80

Val Ile Gly Arg Gly Ala Phe Gly Glu Val Ala Val Val Lys Met Lys
                85                  90                  95

Asn Thr Glu Arg Ile Tyr Ala Met Lys Ile Leu Asn Lys Trp Glu Met
                100                 105                 110
```

```
Leu Lys Arg Ala Glu Thr Ala Cys Phe Arg Glu Arg Asp Val Leu
        115                 120                 125

Val Asn Gly Asp Cys Gln Trp Ile Thr Ala Leu His Tyr Ala Phe Gln
130                 135                 140

Asp Glu Asn Tyr Leu Tyr Leu Val Met Asp Tyr Tyr Val Gly Gly Asp
145                 150                 155                 160

Leu Leu Thr Leu Leu Ser Lys Phe Glu Asp Lys Leu Pro Glu Asp Met
                165                 170                 175

Ala Arg Phe Tyr Ile Gly Glu Met Val Leu Ala Ile Asp Ser Ile His
            180                 185                 190

Gln Leu His Tyr Val His Arg Asp Ile Lys Pro Asp Asn Val Leu Leu
        195                 200                 205

Asp Val Asn Gly His Ile Arg Leu Ala Asp Phe Gly Ser Cys Leu Lys
210                 215                 220

Met Asn Asp Asp Gly Thr Val Gln Ser Ser Val Ala Val Gly Thr Pro
225                 230                 235                 240

Asp Tyr Ile Ser Pro Glu Ile Leu Gln Ala Met Glu Asp Gly Met Gly
                245                 250                 255

Lys Tyr Gly Pro Glu Cys Asp Trp Trp Ser Leu Gly Val Cys Met Tyr
            260                 265                 270

Glu Met Leu Tyr Gly Glu Thr Pro Phe Tyr Ala Glu Ser Leu Val Glu
        275                 280                 285

Thr Tyr Gly Lys Ile Met Asn His Glu Glu Arg Phe Gln Phe Pro Ser
    290                 295                 300

His Val Thr Asp Val Ser Glu Glu Ala Lys Asp Leu Ile Gln Arg Leu
305                 310                 315                 320

Ile Cys Ser Arg Glu Arg Leu Gly Gln Asn Gly Ile Glu Asp Phe
                325                 330                 335

Lys Lys His Ala Phe Phe Glu Gly Leu Asn Trp Glu Asn Ile Arg Asn
            340                 345                 350

Leu Glu Ala Pro Tyr Ile Pro Asp Val Ser Ser Pro Ser Asp Thr Ser
        355                 360                 365

Asn Phe Asp Val Asp Asp Asp Met Leu Arg Asn Ile Glu Ile Leu Pro
    370                 375                 380

Pro Gly Ser His Thr Gly Phe Ser Gly Leu His Leu Pro Phe Ile Gly
385                 390                 395                 400

Phe Thr Phe Thr Thr Glu Ser Cys Phe Ser Asp Arg Gly Ser Leu Lys
                405                 410                 415

Ser Met Thr Gln Ser Asn Thr Leu Thr Lys Asp Glu Asp Val Gln Arg
            420                 425                 430

Asp Leu Glu Asn Ser Leu Gln Ile Glu Ala Tyr Glu Arg Arg Ile Arg
        435                 440                 445

Arg Leu Glu Gln Glu Lys Leu Glu Leu Ser Arg Lys Leu Gln Glu Ser
    450                 455                 460

Thr Gln Thr Val Gln Ser Leu His Gly Ser Thr Arg Ala Leu Gly Asn
465                 470                 475                 480

Ser Asn Arg Asp Lys Glu Ile Lys Arg Leu Asn Glu Glu Leu Glu Arg
                485                 490                 495

Met Lys Ser Lys Met Ala Asp Ser Asn Arg Leu Glu Arg Gln Leu Glu
            500                 505                 510

Asp Thr Val Thr Leu Arg Gln Glu His Glu Asp Ser Thr His Arg Leu
        515                 520                 525

Lys Gly Leu Glu Lys Gln Tyr Arg Leu Ala Arg Gln Glu Lys Glu Glu
```

```
                530             535             540
Leu His Lys Gln Leu Val Glu Ala Ser Glu Arg Leu Lys Ser Gln Thr
545                 550                 555                 560

Lys Glu Leu Lys Asp Ala His Gln Gln Arg Lys Arg Ala Leu Gln Glu
                565                 570                 575

Phe Ser Glu Leu Asn Glu Arg Met Ala Glu Leu Arg Ser Leu Lys Gln
                580                 585                 590

Lys Val Ser Arg Gln Leu Arg Asp Lys Glu Glu Met Glu Val Ala
            595                 600                 605

Met Gln Lys Ile Asp Ser Met Arg Gln Asp Leu Arg Lys Ser Glu Lys
610                 615                 620

Ser Arg Lys Glu Leu Glu Ala Arg Leu Glu Asp Ala Ala Glu Ala
625                 630                 635                 640

Ser Lys Glu Arg Lys Leu Arg Glu His Ser Glu Ser Phe Cys Lys Gln
                645                 650                 655

Met Glu Arg Glu Leu Glu Ala Leu Lys Val Lys Gln Gly Gly Arg Gly
                660                 665                 670

Pro Gly Ala Ala Ser Glu His Gln Gln Glu Ile Ser Lys Ile Arg Ser
            675                 680                 685

Glu Leu Glu Lys Lys Val Leu Phe Tyr Glu Glu Leu Val Arg Arg
690                 695                 700

Glu Ala Ser His Val Leu Glu Val Lys Asn Val Lys Lys Glu Val His
705                 710                 715                 720

Asp Ser Glu Ser His Gln Leu Ala Leu Gln Lys Glu Val Leu Met Leu
                725                 730                 735

Lys Asp Lys Leu Glu Lys Ser Lys Arg Glu Arg His Ser Glu Met Glu
            740                 745                 750

Glu Ala Ile Gly Thr Val Lys Asp Lys Tyr Glu Arg Glu Arg Ala Met
            755                 760                 765

Leu Phe Asp Glu Asn Lys Lys Leu Thr Ala Glu Asn Glu Lys Leu Cys
770                 775                 780

Ser Phe Val Asp Lys Leu Thr Ala Gln Asn Arg Gln Leu Glu Asp Glu
785                 790                 795                 800

Leu Gln Asp Leu Ala Ser Lys Lys Glu Ser Val Ala His Trp Glu Ala
                805                 810                 815

Gln Ile Ala Glu Ile Ile Gln Trp Val Ser Asp Glu Lys Asp Ala Arg
            820                 825                 830

Gly Tyr Leu Gln Ala Leu Ala Ser Lys Met Thr Glu Glu Leu Glu Thr
            835                 840                 845

Leu Arg Ser Ser Ser Leu Gly Ser Arg Thr Leu Asp Pro Leu Trp Lys
850                 855                 860

Val Arg Arg Ser Gln Lys Leu Asp Met Ser Ala Arg Leu Glu Leu Gln
865                 870                 875                 880

Ser Ala Leu Glu Ala Glu Ile Arg Ala Lys Gln Leu Val Gln Glu Glu
                885                 890                 895

Leu Arg Lys Val Lys Asp Ser Ser Leu Ala Phe Glu Ser Lys Leu Lys
                900                 905                 910

Glu Ser Glu Ala Lys Asn Arg Glu Leu Leu Glu Glu Met Gln Ser Leu
                915                 920                 925

Arg Lys Arg Met Glu Glu Lys Phe Arg Ala Asp Thr Gly Leu Lys Leu
930                 935                 940

Pro Asp Phe Gln Asp Ser Ile Phe Glu Tyr Phe Asn Thr Ala Pro Leu
945                 950                 955                 960
```

-continued

Ala His Asp Leu Thr Phe Arg Thr Ser Ser Ala Ser Asp Gln Glu Thr
              965                 970                 975

Gln Ala Ser Lys Met Asp Leu Ser Pro Ser Val Ser Val Ala Thr Ser
              980                 985                 990

Thr Glu Gln Gln Glu Asp Met Ala Arg Pro Gln Gln Arg Pro Ser Pro
              995                 1000                1005

Val Pro Leu Pro Ser Thr Gln Ala Leu Ala Met Ala Gly Pro Lys
        1010                1015                1020

Pro Lys Ala His Gln Phe Ser Ile Lys Ser Phe Pro Ser Pro Thr
        1025                1030                1035

Gln Cys Ser His Cys Thr Ser Leu Met Val Gly Leu Ile Arg Gln
        1040                1045                1050

Gly Tyr Ala Cys Glu Val Cys Ala Phe Ser Cys His Val Ser Cys
        1055                1060                1065

Lys Asp Ser Ala Pro Gln Val Cys Pro Ile Pro Pro Glu Gln Ser
        1070                1075                1080

Lys Arg Pro Leu Gly Val Asp Val Gln Arg Gly Ile Gly Thr Ala
        1085                1090                1095

Tyr Lys Gly Tyr Val Lys Val Pro Lys Pro Thr Gly Val Lys Lys
        1100                1105                1110

Gly Trp Gln Arg Ala Tyr Ala Val Val Cys Asp Cys Lys Leu Phe
        1115                1120                1125

Leu Tyr Asp Leu Pro Glu Gly Lys Ser Thr Gln Pro Gly Val Val
        1130                1135                1140

Ala Ser Gln Val Leu Asp Leu Arg Asp Glu Glu Phe Ala Val Ser
        1145                1150                1155

Ser Val Leu Ala Ser Asp Val Ile His Ala Thr Arg Arg Asp Ile
        1160                1165                1170

Pro Cys Ile Phe Arg Val Thr Ala Ser Leu Leu Gly Ser Pro Ser
        1175                1180                1185

Lys Thr Ser Ser Leu Leu Ile Leu Thr Glu Asn Glu Asn Glu Lys
        1190                1195                1200

Arg Lys Trp Val Gly Ile Leu Glu Gly Leu Gln Ala Ile Leu His
        1205                1210                1215

Lys Asn Arg Leu Lys Ser Gln Val Val His Val Ala Gln Glu Ala
        1220                1225                1230

Tyr Asp Ser Ser Leu Pro Leu Ile Lys Ala Val Leu Ala Ala Ala
        1235                1240                1245

Ile Val Asp Gly Asp Arg Ile Ala Val Gly Leu Glu Glu Gly Leu
        1250                1255                1260

Tyr Val Ile Glu Leu Thr Arg Asp Val Ile Val Arg Ala Ala Asp
        1265                1270                1275

Cys Lys Lys Val Tyr Gln Ile Glu Leu Ala Pro Lys Glu Lys Ile
        1280                1285                1290

Ala Ile Leu Leu Cys Gly Arg Asn His His Val His Leu Tyr Pro
        1295                1300                1305

Trp Ser Ser Phe Asp Gly Ala Glu Ala Ser Asn Phe Asp Ile Lys
        1310                1315                1320

Leu Pro Glu Thr Lys Gly Cys Gln Leu Ile Ala Thr Gly Thr Leu
        1325                1330                1335

Arg Lys Ser Ser Ser Thr Cys Leu Phe Val Ala Val Lys Arg Leu
        1340                1345                1350

Ile Leu Cys Tyr Glu Ile Gln Arg Thr Lys Pro Phe His Arg Lys
        1355                1360                1365

```
Phe Ser Glu Leu Val Ala Pro Gly His Val Gln Trp Met Ala Val
    1370                1375                1380

Phe Lys Asp Arg Leu Cys Val Gly Tyr Pro Ser Gly Phe Ser Leu
1385                1390                1395

Leu Ser Ile Gln Gly Asp Gly Pro Pro Leu Asp Leu Val Asn Pro
    1400                1405                1410

Thr Asp Pro Ser Leu Ala Phe Leu Ser Gln Gln Ser Phe Asp Ala
1415                1420                1425

Leu Cys Ala Val Glu Leu Lys Ser Glu Glu Tyr Leu Leu Cys Phe
    1430                1435                1440

Ser His Met Gly Leu Tyr Val Asp Pro Gln Gly Arg Arg Ser Arg
1445                1450                1455

Met Gln Glu Leu Met Trp Pro Ala Ala Pro Val Ala Cys Ser Cys
    1460                1465                1470

Ser Pro Thr His Val Thr Val Tyr Ser Glu Tyr Gly Val Asp Val
1475                1480                1485

Phe Asp Val Arg Thr Met Glu Trp Val Gln Thr Ile Gly Leu Arg
    1490                1495                1500

Arg Ile Arg Pro Leu Asn Ser Asp Gly Ser Leu Asn Leu Leu Gly
1505                1510                1515

Cys Glu Pro Pro Arg Leu Ile Tyr Phe Lys Asn Lys Phe Ser Gly
    1520                1525                1530

Thr Ile Leu Asn Val Pro Asp Thr Ser Asp Asn Ser Lys Lys Gln
1535                1540                1545

Met Leu Arg Thr Arg Ser Lys Arg Arg Phe Val Phe Lys Val Pro
    1550                1555                1560

Glu Glu Glu Arg Leu Gln Gln Arg Arg Glu Met Leu Arg Asp Pro
1565                1570                1575

Glu Leu Arg Ser Lys Met Ile Ser Asn Pro Thr Asn Phe Asn His
    1580                1585                1590

Val Ala His Met Gly Pro Gly Asp Gly Met Gln Val Leu Met Asp
1595                1600                1605

Leu Pro Leu Ser Ala Ala Pro Thr Val Gln Glu Glu Lys Gln Gly
    1610                1615                1620

Pro Thr Pro Ala Gly Leu Pro Arg Gln Pro Pro Ser Arg Ser Lys
1625                1630                1635

Pro Tyr Val Ser Trp Pro Ser Ser Gly Gly Ser Glu Pro Gly Val
    1640                1645                1650

Pro Val Pro Leu Arg Ser Met Ser Asp Pro Asp Gln Asp Phe Asp
1655                1660                1665

Lys Glu Pro Asp Ser Asp Ser Thr Lys His Ser Thr Pro Ser Asn
    1670                1675                1680

Ser Ser Asn Pro Ser Gly Pro Pro Ser Pro Asn Ser Pro His Arg
1685                1690                1695

Ser Gln Leu Pro Met Glu Gly Leu Asp Gln Pro Ser Cys Asp Ala
    1700                1705                1710

<210> SEQ ID NO 4
<211> LENGTH: 1711
<212> TYPE: PRT
<213> ORGANISM: Homo sapiens

<400> SEQUENCE: 4

Met Ser Ala Lys Val Arg Leu Lys Lys Leu Glu Gln Leu Leu Leu Asp
1               5                   10                  15
```

-continued

```
Gly Pro Trp Arg Asn Glu Ser Ala Leu Ser Val Glu Thr Leu Leu Asp
             20                  25                  30

Val Leu Val Cys Leu Tyr Thr Glu Cys Ser His Ser Ala Leu Arg Arg
         35                  40                  45

Asp Lys Tyr Val Ala Glu Phe Leu Glu Trp Ala Lys Pro Phe Thr Gln
 50                  55                  60

Leu Val Lys Glu Met Gln Leu His Arg Glu Asp Phe Glu Ile Ile Lys
65                  70                  75                  80

Val Ile Gly Arg Gly Ala Phe Gly Glu Val Ala Val Val Lys Met Lys
                 85                  90                  95

Asn Thr Glu Arg Ile Tyr Ala Met Lys Ile Leu Asn Lys Trp Glu Met
            100                 105                 110

Leu Lys Arg Ala Glu Thr Ala Cys Phe Arg Glu Glu Arg Asp Val Leu
        115                 120                 125

Val Asn Gly Asp Cys Gln Trp Ile Thr Ala Leu His Tyr Ala Phe Gln
130                 135                 140

Asp Glu Asn His Leu Tyr Leu Val Met Asp Tyr Tyr Val Gly Gly Asp
145                 150                 155                 160

Leu Leu Thr Leu Leu Ser Lys Phe Glu Asp Lys Leu Pro Glu Asp Met
                165                 170                 175

Ala Arg Phe Tyr Ile Gly Glu Met Val Leu Ala Ile Asp Ser Ile His
            180                 185                 190

Gln Leu His Tyr Val His Arg Asp Ile Lys Pro Asp Asn Val Leu Leu
        195                 200                 205

Asp Val Asn Gly His Ile Arg Leu Ala Asp Phe Gly Ser Cys Leu Lys
210                 215                 220

Met Asn Asp Asp Gly Thr Val Gln Ser Ser Val Ala Val Gly Thr Pro
225                 230                 235                 240

Asp Tyr Ile Ser Pro Glu Ile Leu Gln Ala Met Glu Asp Gly Met Gly
                245                 250                 255

Lys Tyr Gly Pro Glu Cys Asp Trp Trp Ser Leu Gly Val Cys Met Tyr
            260                 265                 270

Glu Met Leu Tyr Gly Glu Thr Pro Phe Tyr Ala Glu Ser Leu Val Glu
        275                 280                 285

Thr Tyr Gly Lys Ile Met Asn His Glu Glu Arg Phe Gln Phe Pro Ser
290                 295                 300

His Val Thr Asp Val Ser Glu Glu Ala Lys Asp Leu Ile Gln Arg Leu
305                 310                 315                 320

Ile Cys Ser Arg Glu Arg Leu Gly Gln Asn Gly Ile Glu Asp Phe
                325                 330                 335

Lys Lys His Ala Phe Phe Glu Gly Leu Asn Trp Glu Asn Ile Arg Asn
            340                 345                 350

Leu Glu Ala Pro Tyr Ile Pro Asp Val Ser Ser Pro Ser Asp Thr Ser
        355                 360                 365

Asn Phe Asp Val Asp Asp Val Leu Arg Asn Thr Glu Ile Leu Pro
370                 375                 380

Pro Gly Ser His Thr Gly Phe Ser Gly Leu His Leu Pro Phe Ile Gly
385                 390                 395                 400

Phe Thr Phe Thr Thr Glu Ser Cys Phe Ser Asp Arg Gly Ser Leu Lys
                405                 410                 415

Ser Ile Met Gln Ser Asn Thr Leu Thr Lys Asp Glu Asp Val Gln Arg
            420                 425                 430

Asp Leu Glu His Ser Leu Gln Met Glu Ala Tyr Glu Arg Arg Ile Arg
```

-continued

```
                435                 440                 445
Arg Leu Glu Gln Glu Lys Leu Glu Leu Ser Arg Lys Leu Gln Glu Ser
450                 455                 460
Thr Gln Thr Val Gln Ser Leu His Gly Ser Ser Arg Ala Leu Ser Asn
465                 470                 475                 480
Ser Asn Arg Asp Lys Glu Ile Lys Lys Leu Asn Glu Glu Ile Glu Arg
                485                 490                 495
Leu Lys Asn Lys Ile Ala Asp Ser Asn Arg Leu Glu Arg Gln Leu Glu
            500                 505                 510
Asp Thr Val Ala Leu Arg Gln Glu Arg Glu Asp Ser Thr Gln Arg Leu
        515                 520                 525
Arg Gly Leu Glu Lys Gln His Arg Val Val Arg Gln Glu Lys Glu Glu
    530                 535                 540
Leu His Lys Gln Leu Val Glu Ala Ser Glu Arg Leu Lys Ser Gln Ala
545                 550                 555                 560
Lys Glu Leu Lys Asp Ala His Gln Gln Arg Lys Leu Ala Leu Gln Glu
                565                 570                 575
Phe Ser Glu Leu Asn Glu Arg Met Ala Glu Leu Arg Ala Gln Lys Gln
            580                 585                 590
Lys Val Ser Arg Gln Leu Arg Asp Lys Glu Glu Glu Met Glu Val Ala
        595                 600                 605
Thr Gln Lys Val Asp Ala Met Arg Gln Glu Met Arg Arg Ala Glu Lys
    610                 615                 620
Leu Arg Lys Glu Leu Glu Ala Gln Leu Asp Asp Ala Val Ala Glu Ala
625                 630                 635                 640
Ser Lys Glu Arg Lys Leu Arg Glu His Ser Glu Asn Phe Cys Lys Gln
                645                 650                 655
Met Glu Ser Glu Leu Glu Ala Leu Lys Val Lys Gln Gly Gly Arg Gly
            660                 665                 670
Ala Gly Ala Thr Leu Glu His Gln Gln Glu Ile Ser Lys Ile Lys Ser
        675                 680                 685
Glu Leu Glu Lys Lys Val Leu Phe Tyr Glu Glu Glu Leu Val Arg Arg
    690                 695                 700
Glu Ala Ser His Val Leu Glu Val Lys Asn Val Lys Lys Glu Val His
705                 710                 715                 720
Asp Ser Glu Ser His Gln Leu Ala Leu Gln Lys Glu Ile Leu Met Leu
                725                 730                 735
Lys Asp Lys Leu Glu Lys Ser Lys Arg Glu Arg His Asn Glu Met Glu
            740                 745                 750
Glu Ala Val Gly Thr Ile Lys Asp Lys Tyr Glu Arg Glu Arg Ala Met
        755                 760                 765
Leu Phe Asp Glu Asn Lys Lys Leu Thr Ala Glu Asn Glu Lys Leu Cys
    770                 775                 780
Ser Phe Val Asp Lys Leu Thr Ala Gln Asn Arg Gln Leu Glu Asp Glu
785                 790                 795                 800
Leu Gln Asp Leu Ala Ala Lys Lys Glu Ser Val Ala His Trp Glu Ala
                805                 810                 815
Gln Ile Ala Glu Ile Ile Gln Trp Val Ser Asp Glu Lys Asp Ala Arg
            820                 825                 830
Gly Tyr Leu Gln Ala Leu Ala Ser Lys Met Thr Glu Leu Glu Ala
        835                 840                 845
Leu Arg Ser Ser Ser Leu Gly Ser Arg Thr Leu Asp Pro Leu Trp Lys
    850                 855                 860
```

-continued

Val Arg Arg Ser Gln Lys Leu Asp Met Ser Ala Arg Leu Glu Leu Gln
865                 870                 875                 880

Ser Ala Leu Glu Ala Glu Ile Arg Ala Lys Gln Leu Val Gln Glu Glu
            885                 890                 895

Leu Arg Lys Val Lys Asp Ala Asn Leu Thr Leu Glu Ser Lys Leu Lys
        900                 905                 910

Asp Ser Glu Ala Lys Asn Arg Glu Leu Leu Glu Glu Met Glu Ile Leu
            915                 920                 925

Lys Lys Lys Met Glu Glu Lys Phe Arg Ala Asp Thr Gly Leu Lys Leu
    930                 935                 940

Pro Asp Phe Gln Asp Ser Ile Phe Glu Tyr Phe Asn Thr Ala Pro Leu
945                 950                 955                 960

Ala His Asp Leu Thr Phe Arg Thr Ser Ser Ala Ser Glu Gln Glu Thr
            965                 970                 975

Gln Ala Pro Lys Pro Glu Ala Ser Pro Ser Met Ser Val Ala Ala Ser
            980                 985                 990

Glu Gln Gln Glu Asp Met Ala Arg Pro Pro Gln Arg Pro Ser Ala Val
        995                 1000                1005

Pro Leu Pro Thr Thr Gln Ala Leu Val Leu Ala Gly Pro Lys Pro
    1010                1015                1020

Lys Ala His Gln Phe Ser Ile Lys Ser Phe Ser Ser Pro Thr Gln
    1025                1030                1035

Cys Ser His Cys Thr Ser Leu Met Val Gly Leu Ile Arg Gln Gly
    1040                1045                1050

Tyr Ala Cys Glu Val Cys Ser Phe Ala Cys His Val Ser Cys Lys
    1055                1060                1065

Asp Gly Ala Pro Gln Val Cys Pro Ile Pro Pro Glu Gln Ser Lys
    1070                1075                1080

Arg Pro Leu Gly Val Asp Val Gln Arg Gly Ile Gly Thr Ala Tyr
    1085                1090                1095

Lys Gly His Val Lys Val Pro Lys Pro Thr Gly Val Lys Lys Gly
    1100                1105                1110

Trp Gln Arg Ala Tyr Ala Val Val Cys Glu Cys Lys Leu Phe Leu
    1115                1120                1125

Tyr Asp Leu Pro Glu Gly Lys Ser Thr Gln Pro Gly Val Ile Ala
    1130                1135                1140

Ser Gln Val Leu Asp Leu Arg Asp Asp Glu Phe Ser Val Ser Ser
    1145                1150                1155

Val Leu Ala Ser Asp Val Ile His Ala Thr Arg Arg Asp Ile Pro
    1160                1165                1170

Cys Ile Phe Arg Val Thr Ala Ser Leu Leu Gly Ala Pro Ser Lys
    1175                1180                1185

Thr Ser Ser Leu Leu Ile Leu Thr Glu Asn Glu Asn Glu Lys Arg
    1190                1195                1200

Lys Trp Val Gly Ile Leu Glu Gly Leu Gln Ser Ile Leu His Lys
    1205                1210                1215

Asn Arg Leu Arg Asn Gln Val Val His Val Pro Leu Glu Ala Tyr
    1220                1225                1230

Asp Ser Ser Leu Pro Leu Ile Lys Ala Ile Leu Thr Ala Ala Ile
    1235                1240                1245

Val Asp Ala Asp Arg Ile Ala Val Gly Leu Glu Glu Gly Leu Tyr
    1250                1255                1260

Val Ile Glu Val Thr Arg Asp Val Ile Val Arg Ala Ala Asp Cys
    1265                1270                1275

-continued

```
Lys Lys Val His Gln Ile Glu Leu Ala Pro Arg Glu Lys Ile Val
1280             1285                 1290

Ile Leu Leu Cys Gly Arg Asn His His Val His Leu Tyr Pro Trp
    1295             1300                 1305

Ser Ser Leu Asp Gly Ala Glu Gly Ser Phe Asp Ile Lys Leu Pro
    1310             1315                 1320

Glu Thr Lys Gly Cys Gln Leu Met Ala Thr Ala Thr Leu Lys Arg
    1325             1330                 1335

Asn Ser Gly Thr Cys Leu Phe Val Ala Val Lys Arg Leu Ile Leu
1340             1345                 1350

Cys Tyr Glu Ile Gln Arg Thr Lys Pro Phe His Arg Lys Phe Asn
1355             1360                 1365

Glu Ile Val Ala Pro Gly Ser Val Gln Cys Leu Ala Val Leu Arg
1370             1375                 1380

Asp Arg Leu Cys Val Gly Tyr Pro Ser Gly Phe Cys Leu Leu Ser
1385             1390                 1395

Ile Gln Gly Asp Gly Gln Pro Leu Asn Leu Val Asn Pro Asn Asp
1400             1405                 1410

Pro Ser Leu Ala Phe Leu Ser Gln Gln Ser Phe Asp Ala Leu Cys
1415             1420                 1425

Ala Val Glu Leu Glu Ser Glu Glu Tyr Leu Leu Cys Phe Ser His
1430             1435                 1440

Met Gly Leu Tyr Val Asp Pro Gln Gly Arg Arg Ala Arg Ala Gln
1445             1450                 1455

Glu Leu Met Trp Pro Ala Ala Pro Val Ala Cys Ser Cys Ser Pro
1460             1465                 1470

Thr His Val Thr Val Tyr Ser Glu Tyr Gly Val Asp Val Phe Asp
1475             1480                 1485

Val Arg Thr Met Glu Trp Val Gln Thr Ile Gly Leu Arg Arg Ile
1490             1495                 1500

Arg Pro Leu Asn Ser Glu Gly Thr Leu Asn Leu Leu Asn Cys Glu
1505             1510                 1515

Pro Pro Arg Leu Ile Tyr Phe Lys Ser Lys Phe Ser Gly Ala Val
1520             1525                 1530

Leu Asn Val Pro Asp Thr Ser Asp Asn Ser Lys Lys Gln Met Leu
1535             1540                 1545

Arg Thr Arg Ser Lys Arg Arg Phe Val Phe Lys Val Pro Glu Glu
1550             1555                 1560

Glu Arg Leu Gln Gln Arg Arg Glu Met Leu Arg Asp Pro Glu Leu
1565             1570                 1575

Arg Ser Lys Met Ile Ser Asn Pro Thr Asn Phe Asn His Val Ala
1580             1585                 1590

His Met Gly Pro Gly Asp Gly Met Gln Val Leu Met Asp Leu Pro
1595             1600                 1605

Leu Ser Ala Val Pro Pro Ser Gln Glu Glu Arg Pro Gly Pro Ala
1610             1615                 1620

Pro Thr Asn Leu Ala Arg Gln Pro Pro Ser Arg Asn Lys Pro Tyr
1625             1630                 1635

Ile Ser Trp Pro Ser Ser Gly Gly Ser Glu Pro Ser Val Thr Val
1640             1645                 1650

Pro Leu Arg Ser Met Ser Asp Pro Asp Gln Asp Phe Asp Lys Glu
1655             1660                 1665

Pro Asp Ser Asp Ser Thr Lys His Ser Thr Pro Ser Asn Ser Ser
```

1670                1675                1680

Asn Pro  Ser Gly Pro Pro Ser  Pro Asn Ser Pro His  Arg Ser Gln
        1685                1690                1695

Leu Pro  Leu Glu Gly Leu Glu  Gln Pro Ala Cys Asp  Thr
        1700                1705                1710

<210> SEQ ID NO 5
<211> LENGTH: 51
<212> TYPE: PRT
<213> ORGANISM: Mus musculus

<400> SEQUENCE: 5

Met Glu Glu Met Leu Ser Phe Arg Asp Val Ala Ile Asp Phe Ser Ala
1               5                   10                  15

Glu Glu Trp Glu Cys Leu Glu Pro Ala Gln Trp Asn Leu Tyr Arg Asp
            20                  25                  30

Val Met Leu Glu Asn Tyr Thr His Leu Val Phe Leu Gly Glu Gly His
        35                  40                  45

Val His Lys
    50

<210> SEQ ID NO 6
<211> LENGTH: 924
<212> TYPE: PRT
<213> ORGANISM: Mus musculus

<400> SEQUENCE: 6

Met Ser Arg Ser Arg Gln Pro Pro Leu Val Thr Gly Ile Ser Pro Asn
1               5                   10                  15

Glu Gly Ile Pro Trp Thr Lys Val Thr Ile Arg Gly Glu Asn Leu Gly
            20                  25                  30

Thr Gly Pro Thr Asp Leu Ile Gly Leu Thr Ile Cys Gly His Asn Cys
        35                  40                  45

Leu Leu Thr Ala Glu Trp Met Ser Ala Ser Lys Ile Val Cys Arg Val
    50                  55                  60

Gly Gln Ala Lys Asn Asp Lys Gly Asp Ile Ile Val Thr Thr Lys Ser
65                  70                  75                  80

Gly Gly Lys Gly Thr Ser Thr Val Ser Phe Lys Leu Leu Lys Pro Glu
                85                  90                  95

Lys Ile Gly Ile Leu Asp Gln Ser Ala Val Trp Val Asp Glu Met Asn
            100                 105                 110

Tyr Tyr Asp Met Arg Thr Asp Arg Asn Lys Gly Ile Pro Pro Leu Ser
        115                 120                 125

Leu Arg Pro Ala Asn Pro Leu Gly Ile Glu Ile Glu Lys Cys Lys Leu
    130                 135                 140

Pro Gln Lys Asn Leu Glu Val Leu Phe His Gly Met Ser Ala Asp Phe
145                 150                 155                 160

Thr Ser Glu Asn Phe Ser Ala Ala Trp Tyr Leu Ile Glu Asn His Ser
                165                 170                 175

Thr Thr Ser Phe Glu Gln Leu Lys Met Ala Val Thr Asn Leu Lys Arg
            180                 185                 190

Gln Ala Asn Lys Lys Ser Glu Gly Ser Leu Ala Tyr Val Lys Gly Gly
        195                 200                 205

Leu Ser Thr Phe Phe Glu Ala Gln Asp Ala Leu Ser Ala Ile His Gln
    210                 215                 220

Lys Leu Glu Ala Asp Gly Thr Glu Lys Val Glu Gly Ser Met Thr Gln
225                 230                 235                 240

```
Lys Leu Glu Asn Val Leu Asn Arg Ala Ser Asn Thr Ala Asp Thr Leu
                245                 250                 255
Phe Gln Glu Val Leu Gly Arg Lys Asp Lys Ala Asp Ser Thr Arg Asn
                260                 265                 270
Ala Leu Asn Val Leu Gln Arg Phe Lys Phe Leu Phe Asn Leu Pro Leu
                275                 280                 285
Asn Ile Lys Arg Asn Ile Gln Lys Gly Asp Tyr Asp Val Val Ile Asn
                290                 295                 300
Asp Tyr Glu Lys Ala Lys Ser Leu Phe Gly Lys Thr Glu Val Gln Val
305                 310                 315                 320
Phe Lys Lys Tyr Tyr Ala Glu Val Glu Ala Gly Ile Glu Asp Leu Arg
                325                 330                 335
Glu Leu Leu Leu Lys Lys Leu Leu Glu Thr Pro Ser Thr Leu His Asp
                340                 345                 350
Gln Lys Arg Tyr Ile Arg Tyr Leu Ser Asp Leu His Ala Pro Gly Asp
                355                 360                 365
Pro Ala Trp Gln Cys Ile Gly Ala Gln His Lys Trp Thr Leu Lys Leu
                370                 375                 380
Met Gln Asp Cys Lys Glu Gly His Met Lys Ser Leu Lys Gly His Pro
385                 390                 395                 400
Gly Pro His Ser Pro Met Leu Asp Leu Asp Asn Asp Val Arg Pro Ser
                405                 410                 415
Val Leu Gly His Leu Ser Gln Thr Ala Ser Leu Lys Arg Gly Ser Ser
                420                 425                 430
Phe Gln Ser Gly Arg Asp Asp Thr Trp Arg Tyr Lys Thr Pro His Arg
                435                 440                 445
Val Ala Phe Val Glu Lys Leu Thr Lys Leu Val Leu Ser Gln Leu Pro
                450                 455                 460
Asn Phe Trp Lys Leu Trp Ile Ser Tyr Val Asn Gly Ser Leu Phe Ser
465                 470                 475                 480
Glu Thr Ala Glu Lys Ser Gly Gln Ser Glu Arg Ser Lys Asn Val Arg
                485                 490                 495
Gln Arg Gln Asn Asp Phe Lys Lys Met Ile Gln Glu Val Met His Ser
                500                 505                 510
Leu Val Lys Leu Ile Arg Gly Ala Leu Leu Pro Leu Ser Leu Arg Glu
                515                 520                 525
Gly Asp Gly Arg Gln Tyr Gly Gly Trp Glu Val Gln Ala Glu Leu Ser
530                 535                 540
Gly Gln Trp Leu Ala His Val Ile Gln Thr Ile Arg Leu Thr Tyr Glu
545                 550                 555                 560
Ser Leu Thr Ala Leu Glu Ile Pro Asn Asp Met Leu Gln Ile Ile Gln
                565                 570                 575
Asp Leu Ile Leu Asp Leu Arg Ile Arg Cys Ile Met Val Thr Leu Gln
                580                 585                 590
His Thr Ala Glu Glu Ile Lys Arg Leu Ala Glu Lys Glu Asp Trp Val
                595                 600                 605
Val Asp Asn Glu Gly Leu Thr Ser Leu Pro Cys Gln Phe Glu Gln Ser
                610                 615                 620
Ile Val His Ser Leu Gln Ser Leu Lys Gly Val Val Asp Cys Lys Pro
625                 630                 635                 640
Gly Glu Ala Ser Val Phe Gln Gln Pro Lys Thr Gln Glu Glu Val Cys
                645                 650                 655
Gln Leu Cys Ile Asn Ile Met Gln Val Phe Ile Tyr Cys Leu Glu Gln
```

```
                    660                 665                 670
Leu Ser Thr Lys Pro Asp Ala Asp Ile Asp Thr Thr His Leu Ser Val
            675                 680                 685
Asp Val Ser Ser Pro Asp Leu Phe Gly Ser Ile His Glu Asp Phe Ser
            690                 695                 700
Leu Thr Ser Glu Gln Arg Leu Leu Ile Val Leu Ser Asn Cys Cys Tyr
705                 710                 715                 720
Leu Glu Arg His Thr Phe Leu Asn Ile Ala Glu His Phe Glu Lys His
            725                 730                 735
Asn Phe Gln Gly Ile Glu Lys Ile Thr Gln Val Ser Met Ala Ser Leu
            740                 745                 750
Lys Glu Leu Asp Gln Arg Leu Phe Glu Asn Tyr Ile Glu Leu Lys Ala
            755                 760                 765
Asp Pro Ile Val Gly Ser Leu Glu Pro Gly Ile Tyr Ala Gly Tyr Phe
            770                 775                 780
Asp Trp Lys Asp Cys Leu Pro Ala Gly Val Arg Asn Tyr Leu Lys
785                 790                 795                 800
Glu Ala Leu Val Asn Ile Ile Ala Val His Ala Glu Val Phe Thr Ile
            805                 810                 815
Ser Lys Glu Leu Val Pro Arg Val Leu Ala Arg Val Glu Ala Val
            820                 825                 830
Ser Glu Glu Leu Ser Arg Leu Met Gln Cys Val Ser Ser Phe Ser Arg
            835                 840                 845
Asn Gly Ala Leu Gln Ala Arg Leu Glu Ile Cys Ala Leu Arg Asp Thr
            850                 855                 860
Val Ala Ile Tyr Leu Thr Ser Glu Ser Arg Ser Phe Lys Gln Ala
865                 870                 875                 880
Leu Glu Ala Leu Pro Gln Leu Ala Ser Gly Ala Asp Lys Lys Ser Leu
            885                 890                 895
Glu Glu Leu Leu Asn Lys Phe Lys Ser Ser Met His Leu Gln Leu Thr
            900                 905                 910
Cys Phe Gln Ala Ala Ser Pro Ala Val Met Lys Thr
            915                 920

<210> SEQ ID NO 7
<211> LENGTH: 552
<212> TYPE: PRT
<213> ORGANISM: Mus musculus

<400> SEQUENCE: 7

Pro Arg Phe Ser Trp Ala Ala Gln Glu Pro Ser Gln Pro Lys Lys
1               5                   10                  15
Ile Val Ala Pro Thr Val Ser Gln Ile Asn Ala Glu Phe Val Thr Gln
            20                  25                  30
Leu Ala Cys Lys Tyr Trp Ala Pro His Ile Lys Lys Ser Pro Phe
            35                  40                  45
Asp Ile Lys Val Ile Glu Glu Ile Tyr Glu Lys Glu Ile Val Lys Ser
            50                  55                  60
Arg Phe Ala Ile Arg Lys Ile Met Leu Leu Glu Phe Ser Gln Tyr Leu
65              70                  75                  80
Glu Asn Tyr Leu Trp Met Asn Tyr Ser Pro Glu Val Ser Ser Lys Ala
            85                  90                  95
Tyr Leu Met Ser Ile Cys Cys Met Val Asn Glu Lys Phe Arg Glu Asn
            100                 105                 110
Val Pro Ala Trp Glu Thr Phe Lys Lys Lys Pro Asp His Phe Pro Phe
```

```
                115             120             125
Phe Phe Lys Cys Ile Leu Lys Ala Ala Leu Ala Glu Thr Asp Gly Glu
        130                 135                 140
Phe Ser Leu His Glu Gln Thr Leu Leu Leu Phe Leu Asp His Cys
145                 150                 155                 160
Phe Asn Ser Leu Glu Val Asp Leu Ile Arg Ser Gln Val Gln Gln Leu
                165                 170                 175
Ile Ser Leu Pro Met Trp Met Gly Leu Gln Pro Ala Arg Leu Glu Leu
            180                 185                 190
Glu Leu Lys Lys Thr Pro Lys Leu Arg Lys Phe Trp Asn Leu Ile Lys
        195                 200                 205
Lys Asn Asp Glu Lys Met Asp Pro Glu Ala Arg Glu Gln Ala Tyr Gln
210                 215                 220
Glu Arg Arg Phe Leu Ser Arg Leu Ile Gln Lys Phe Ile Ser Val Leu
225                 230                 235                 240
Lys Ser Ile Pro Leu Ser Glu Pro Val Thr Met Asp Lys Val His Tyr
                245                 250                 255
Cys Glu Arg Phe Ile Glu Leu Met Ile Asp Leu Glu Ala Leu Leu Pro
            260                 265                 270
Thr Arg Arg Trp Phe Asn Thr Ile Leu Asp Asp Ser His Leu Leu Val
        275                 280                 285
His Cys Tyr Leu Ser Ser Leu Val His Arg Glu Asp Gly His Leu
        290                 295                 300
Phe Ser Gln Leu Leu Asp Met Leu Lys Phe Tyr Thr Gly Phe Glu Ile
305                 310                 315                 320
Asn Asp Gln Thr Gly Asn Ala Leu Thr Glu Asn Glu Met Thr Thr Ile
                325                 330                 335
His Tyr Asp Arg Ile Thr Ser Leu Gln Arg Ala Ala Phe Ala His Phe
            340                 345                 350
Ser Glu Leu Tyr Asp Phe Ala Leu Ser Asn Val Ala Glu Val Asp Ala
        355                 360                 365
Arg Asp Ser Leu Val Lys Phe Phe Gly Pro Leu Ser Ser Asn Thr Leu
        370                 375                 380
His Gln Val Ala Ser Tyr Leu Cys Leu Leu Pro Thr Leu Pro Lys Asn
385                 390                 395                 400
Glu Asp Thr Thr Phe Asp Lys Glu Phe Leu Glu Leu Leu Val Ser
                405                 410                 415
Arg His Glu Arg Arg Ile Ser Gln Ile Gln Gln Leu Asn Gln Met Pro
            420                 425                 430
Leu Tyr Pro Thr Glu Lys Ile Ile Trp Asp Glu Asn Ile Val Pro Thr
        435                 440                 445
Glu Tyr Tyr Ser Gly Glu Gly Cys Leu Ala Leu Pro Lys Leu Asn Leu
        450                 455                 460
Gln Phe Leu Thr Leu His Asp Tyr Leu Leu Arg Asn Phe Asn Leu Phe
465                 470                 475                 480
Arg Leu Glu Ser Thr Tyr Glu Ile Arg Gln Asp Ile Glu Asp Ser Val
                485                 490                 495
Ser Arg Met Lys Pro Trp Gln Ser Glu Tyr Gly Gly Val Val Val
            500                 505                 510
Phe Arg Trp Leu Gly His Gly Cys Pro Ala His Cys Gly Phe His Cys
        515                 520                 525
Ser Arg Gly Cys Gln Thr Pro Thr Ser Val Lys Thr Gly Gln Pro Glu
        530                 535                 540
```

Phe Val Gln Met Ser Pro Ser Ile
545                 550

<210> SEQ ID NO 8
<211> LENGTH: 1896
<212> TYPE: DNA
<213> ORGANISM: Mus musculus

<400> SEQUENCE: 8

| | | | | | |
|---|---|---|---|---|---|
| atgtcagccg | aagtgcggct | gaggcagctc | cagcagctgg | tgctggaccc | aggcttcctg | 60 |
| ggactggagc | ccctgctcga | ccttctcctg | ggcgtccacc | aggagctggg | tgcctctcac | 120 |
| ctagcccagg | acaagtatgt | ggccgacttc | ttgcagtggg | tggagcccat | tgcagcaagg | 180 |
| cttaaggagg | tccgactgca | gagggatgat | tttgagattt | tgaaggtgat | cgggcgtggg | 240 |
| gcgttcagcg | aggtagcggt | ggtgaagatg | aaacagacgg | gccaagtgta | tgccatgaag | 300 |
| attatgaata | gtgggacat | gctgaagaga | ggcgaggtgt | cgtgcttccg | ggaagaaagg | 360 |
| gatgtattag | tgaaagggga | ccggcgctgg | atcacacagc | tgcactttgc | cttccaggat | 420 |
| gagaactacc | tgtacctggt | catggaatac | tacgtgggcg | ggacctgct | aacgctgctg | 480 |
| agcaagtttg | gggagcggat | ccccgccgag | atggctcgct | tctacctggc | cgagattgtc | 540 |
| atggccatag | actccgtgca | ccggctgggc | tacgtgcaca | gggacatcaa | accagataac | 600 |
| attctgctgg | accgatgtgg | gcacattcgc | ctggcagact | tcggctcctg | cctcaaactg | 660 |
| cagcctgatg | gaatggtgag | gtcgctggtg | gctgtgggca | ccccggacta | cctgtctcct | 720 |
| gagattctgc | aggccgttgg | tggagggcct | ggggcaggca | gctacgggcc | agagtgtgac | 780 |
| tggtgggcac | tgggcgtgtt | cgcctatgag | atgttctatg | gcagacccc | cttctacgcg | 840 |
| gactccacag | ccgagacata | tgccaagatt | gtgcactaca | ggaacactt | gtcgctgccg | 900 |
| ctggcagaca | cagttgtccc | cgaggaagct | caggacctca | ttcgtgggct | gctgtgtcct | 960 |
| gctgagataa | ggctaggtcg | aggtggggca | ggtgatttcc | agaaacatcc | tttcttcttt | 1020 |
| ggccttgatt | gggagggtct | ccgagacagt | gtacccccct | ttacaccaga | cttcgagggt | 1080 |
| gccacggaca | catgcaattt | cgatgtggtg | gaggaccggc | tcactgccat | ggtgagcggg | 1140 |
| ggcggggaga | cgctgtcaga | catgcaggaa | gacatgcccc | ttggggtgcg | cctgcccttc | 1200 |
| gtgggctact | cctactgctg | catggccttc | agagacaatc | aggtcccgga | ccccacccct | 1260 |
| atggaactag | aggccctgca | gttgcctgtg | tcagacttgc | aagggcttga | cttgcagccc | 1320 |
| ccagtgtccc | caccggatca | agtggctgaa | gaggccgacc | tagtggctgt | ccctgccccct | 1380 |
| gtggctgagg | cagagaccac | ggtaacgctg | cagcagctcc | aggaagccct | ggaagaagag | 1440 |
| gttctcaccc | ggcagagcct | gagccgcgag | ctggaggcca | ttcggaccgc | caaccagaac | 1500 |
| ttctccagcc | aactacagga | ggccgaggtc | cgaaaccgag | acctggaggc | gcatgttcgg | 1560 |
| cagctacagg | aacggatgga | gatgctgcag | gccccaggag | ccgcagccat | cacgggggtc | 1620 |
| cccagtcccc | gggccacgga | tccaccttcc | catctagatg | gccccccggc | cgtggctgtg | 1680 |
| ggccagtgcc | cgctggtggg | gccaggcccc | atgcaccgcc | gtcacctgct | gctccctgcc | 1740 |
| aggatcccta | ggcctggcct | atccgaggcg | cgttgcctgc | tcctgttcgc | cgctgctctg | 1800 |
| gctgctgccg | ccacactggg | ctgcactggg | ttggtggcct | ataccggcgg | tctcaccccca | 1860 |
| gtctggtgtt | tcccgggaac | caccttcgcc | ccctga | | | 1896 |

<210> SEQ ID NO 9
<211> LENGTH: 9
<212> TYPE: PRT
<213> ORGANISM: Mus musculus

```
<400> SEQUENCE: 9

Phe Gln Asp Glu Asn Tyr Leu Tyr Leu
1               5

<210> SEQ ID NO 10
<211> LENGTH: 9
<212> TYPE: PRT
<213> ORGANISM: Mus musculus

<400> SEQUENCE: 10

Arg Leu Phe Glu Asn Tyr Ile Glu Leu
1               5

<210> SEQ ID NO 11
<211> LENGTH: 9
<212> TYPE: PRT
<213> ORGANISM: Mus musculus

<400> SEQUENCE: 11

Gln Tyr Leu Glu Asn Tyr Leu Trp Met
1               5

<210> SEQ ID NO 12
<211> LENGTH: 9
<212> TYPE: PRT
<213> ORGANISM: Mus musculus

<400> SEQUENCE: 12

Val Met Leu Glu Asn Tyr Thr His Leu
1               5

<210> SEQ ID NO 13
<211> LENGTH: 9
<212> TYPE: PRT
<213> ORGANISM: Artificial
<220> FEATURE:
<223> OTHER INFORMATION: peptide MimA2

<400> SEQUENCE: 13

Tyr Ala Ile Glu Asn Tyr Leu Glu Leu
1               5

<210> SEQ ID NO 14
<211> LENGTH: 9
<212> TYPE: PRT
<213> ORGANISM: Artificial
<220> FEATURE:
<223> OTHER INFORMATION: peptide Mim

<400> SEQUENCE: 14

Tyr Phe Ile Glu Asn Tyr Leu Glu Leu
1               5

<210> SEQ ID NO 15
<211> LENGTH: 5260
<212> TYPE: DNA
<213> ORGANISM: Mus musculus

<400> SEQUENCE: 15
atgtcggcca aggtgcggct caagaagctg gagcagctgc tcctggacgg gccgtggcgc     60
aacgatagcg ccctgagcgt ggagacgctg ctggacgtgc tggtgtgcct ttacaccgag    120
tgcagccact cggcgctgcg ccgcgacaag tatgtggcgg agttcctcga gtgggccaag    180
cctttcaccc agctcgtgaa ggacatgcag cttcatcgag aagacttcga gatcatcaaa    240
```

```
gtgatcggga gaggagcctt tggtgaggtt gctgttgtca aaatgaagaa cactgaacga    300
atttatgcaa tgaaaattct caacaaatgg gaaatgctaa agagagcaga gacagcttgc    360
tttcgagaag agcgtgacgt gctggtgaac ggcgactgcc agtggatcac ggctctgcac    420
tatgcctttc aggatgagaa ctacctgtac ttggtcatgg attactatgt aggtggtgat    480
ctgctgaccc tgctgagtaa gtttgaagac aagcttccgg aagacatggc gaggttctac    540
attggcgaga tggtgttggc cattgactcg atccaccagc tccactatgt gcacagagac    600
atcaagcccg acaacgtcct tctagatgtg aacggtcaca tccgcctggc tgactttggc    660
tcgtgcttga agatgaacga tgatggcact gttcagtctt ccgtggccgt gggcacacct    720
gactacatct caccagagat cctgcaggcc atggaggatg gcatgggcaa atacgggccc    780
gagtgtgact ggtggtcgct gggcgtctgc atgtatgaga tgctatacgg agaaaccccg    840
ttctacgcag agtctctggt ggagacatac gggaagatca tgaaccacga ggagcggttt    900
cagttcccat cccatgtcac cgatgtctct gaagaagcaa agaccttat ccagagacta     960 atatgcagca gagagcgccg acttgggcag aatggaatag aagactttaa gaaacacgca   1020
ttctttgaag gtctgaattg ggagaatata cgaaaccttg aagcgcccta cattcccgat   1080
gtgagcagcc cttcggacac gtccaacttc gatgtggacg acgacatgct gagaaacatt   1140
gaaatcttac ctcccggctc tcacacgggc ttctcgggac tgcatttgcc cttcatcggt   1200
ttcacattca cgacggaaag ctgcttttct gaccggggct ctctgaagag catgactcag   1260
tctaacacgc taaccaaaga cgaagatgtg cagcgggact ggagaacag cttgcagatc    1320 gaagcgtacg agcgaaggat acggaggctg gagcaggaga agctggagct cagccggaag   1380
ctgcaagaat ccacccagac tgtgcagtcc cttcacggtt ccacacgggc cctgggcaac   1440
tcaaaccgcg acaaggaaat caagaggctg aatgaagagc ttgaacgcat gaagagtaaa   1500
atggcagatt caaacaggct cgaacgccag ctggaggaca cagtgacact tcgccaggag   1560
catgaggact ccacacaccg gctgaagggc ctcgagaagc agtaccgcct ggcccggcag   1620
gagaaggaag aattgcacaa gcaattggtt gaggcttcag agcgattgaa atcccagacc   1680
aaagaactta agacgcgcca tcagcagcga aaacgggccc tgcaggagtt ctcagagctc   1740
aatgagcgca tggcggagct caggtcgctg aagcagaagg tgtcccgtca gctccgggac   1800
aaggaggagg agatggaggt ggccatgcag aagatcgact ccatgcggca ggacctccgc   1860
aagtctgaga agtccaggaa agagctggaa gctcggcttg aggacgcagc tgccgaggcc   1920
tctaaggagc ggaagctccg agaacacagc gagagcttct gtaagcagat ggagcgcgag   1980
ctcgaggccc tcaaggtaaa gcaaggaggc cgggggccag gggccgcgtc ggaacatcag   2040
caggagatct ccaaaatcag gtcagagctc gagaagaaag tcttgttcta cgaggaggag   2100
ctggtgcgcc gagaggcctc ccacgtgcta gaagtaaaga acgtgaagaa ggaagtccac   2160
gactccgaaa gccaccagtt ggccctgcag aaagaggtcc tgatgctgaa agacaagtta   2220
gaaaagtcaa agcgagaacg gcacagtgag atggaggagg ccataggcac cgtgaaggac   2280
aagtacgaac gggagagggc catgctgttc gatgagaaca agaagttaac agcagaaaac   2340
gaaaagcttt gttcctttgt ggataaacta acagcccaaa acagacagct ggaagatgag   2400
ctgcaggatc tggcatccaa gaaggagtca gttgcgcact gggaggcgca gatcgcagag   2460
atcattcagt gggtcagcga tgagaaagat gccagaggct accttcaagc ccttgcttct   2520
aagatgaccg aagagcttga gaccttgcga agttctagtt tgggatccag gacactggat   2580
ccactctgga aagttcgtcg gagtcagaag ctggacatgt ctgcacggct ggaattgcag   2640
```

```
tctgctcttg aggccgagat ccgtgccaaa cagctcgttc aggaggagct gaggaaggtc    2700
aaagacagca gcctggcctt cgaaagcaaa ctgaaggaat cggaagcgaa aaacagggaa    2760
ttgttagaag aaatgcaaag tctgaggaag aggatggaag agaagtttag agcggataca    2820
gggctcaaac ttccagattt ccaggattct atctttgagt atttcaacac tgctcctctt    2880
gcacatgatc tgactttag aaccagctca gctagtgacc aggaaacaca ggcttcaaag    2940
atggacttgt ccccatcagt gtctgtagcc acgagcacag agcagcagga ggatatggct    3000
cggccacagc agaggccgtc tcctgtgccg ctgcccagca cgcaggccct cgccatggct    3060
ggaccgaagc ccaaagccca ccagttcagc atcaagtcct tccctagccc cacccagtgc    3120
agccactgca cgtccttgat ggtcggactg atccgacagg gctacgcctg tgaggtctgt    3180
gcattttcct gccatgtgtc ctgcaaagac agcgctcccc aggtgtgccc catacctcct    3240
gagcagtcca agaggcctct tggcgtagac gtgcagaggg cataggcac ggcctacaag    3300 ggctacgtca aggtcccaaa gcccacaggc gtgaagaaag gatggcagag ggcttacgcc    3360
gtggtctgtg actgcaaact cttcctgtac gacctgccag aagggaagtc gacccagccc    3420
ggtgtcgttg ccagtcaagt cttggacctc agagatgagg agtttgctgt gagttcagtc    3480
ctggcctcag atgttatcca tgctacacgc cgagacattc cgtgcatatt cagggtgacg    3540
gcctctctct taggttcgcc ttctaagacc agctcactgc tcatcctgac ggagaacgag    3600
aatgaaaaga ggaagtgggt agggatcctt gaagggctgc aggccatctt gcacaagaac    3660
cggctgaaga gccaggtagt gcacgtcgca caggaggcct acgacagctc gctgccgctc    3720
atcaaggccg tcctggctgc tgctatcgtg gatggagaca ggattgcggt cggcctggaa    3780
gaagggctct acgtcattga gctcacccga gacgtgatcg tccgcgctgc tgactgcaag    3840
aaggtgtacc agatcgagct ggcgcccaag gagaagatcg ccatcctcct gtgtggccgg    3900
aaccaccatg tgcacctcta cccctggtcc tccttcgacg gagcagaagc gagcaacttt    3960
gacatcaagc tcccggaaac aaagggctgc cagctcatag cgacagggac gctgaggaag    4020
agctcgtcca cctgcctgtt tgtcgctgtg aagcgactaa tcctttgcta cgagatccag    4080
agaactaagc cttttccacag gaagttcagt gagctggtgg ctccgggaca cgtgcagtgg    4140
atggccgtgt tcaaggacag gctctgtgtt ggctaccct ctgggttctc tctgttgagc    4200
atccaggggg acgggccgcc tctcgacctg gtaaatccca ctgacccctc gctcgcgttc    4260
ctctcacagc agtctttcga tgccctctgt gctgtggagc tcaaaagtga ggagtacctg    4320
ctttgcttca gccacatggg actgtacgtg gaccctcaag gtcggaggtc acgcatgcag    4380
gagctcatgt ggcctgcggc tcctgtcgcc tgtagttgca gccccaccca tgtcacagtg    4440
tacagcgaat acggggtgga tgtcttcgac gtgcgcacca tggagtgggt tcagaccatc    4500
ggcctgcgga ggataagacc tctgaactct gatggcagcc tcaacctgct gggctgtgag    4560 cccctcgcc tcatctactt caaaaacaag ttctcaggaa caatcctcaa tgtgcccgac    4620
acctcggaca cagcaagaa gcagatgctg aggacacgga gcaaacggcg ttttgtcttc    4680
aaggttcccg aggaagagcg gctacagcag cggcgagaga tgctcagaga ccccgaactg    4740
cgatccaaaa tgatatccaa cccaaccaac ttcaaccacg tggctcacat gggtcctggg    4800
gatggcatgc aggtgctcat ggacctgcct ctgagtgctg cacccactgt ccaggaggag    4860
aagcagggcc ctaccccagc aggcctcccc cggcagccgc catccaggag caagccctat    4920
gtctcgtggc cgtcgtcagg tgggtccgag cctggagtgc ctgtgcctct gaggagcatg    4980
tccgaccccg accaggattt tgacaaagag cctgactctg attccaccaa acactcaact    5040
```

```
ccatccaata gctccaaccc tagcggcccc ccaagcccca actcgcccca tcggagccag    5100
ctccctatgg aaggcctgga ccagccatcc tgtgacgcct gaggcctcca gcatagcacc    5160
gtggggccag ggagcccgaa tggccccagc atcagtgcca aggctgagct gacgactctc    5220
cagtgttgtc caaggaaatg tagaatcagt ttgtagatag                          5260

<210> SEQ ID NO 16
<211> LENGTH: 9
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: Xaa can be Ile, Asp, Phe, or Leu
<220> FEATURE:
<221> NAME/KEY: MISC_FEATURE
<222> LOCATION: (7)..(7)
<223> OTHER INFORMATION: Xaa can be Ile or Leu
<220> FEATURE:
<221> NAME/KEY: MISC_FEATURE
<222> LOCATION: (8)..(8)
<223> OTHER INFORMATION: Xaa can be Glu, Trp, or Tyr
<220> FEATURE:
<221> NAME/KEY: MISC_FEATURE
<222> LOCATION: (9)..(9)
<223> OTHER INFORMATION: Xaa can be Leu or Met

<400> SEQUENCE: 16

Xaa Xaa Xaa Glu Asn Tyr Xaa Xaa Xaa
1               5

<210> SEQ ID NO 17
<211> LENGTH: 9
<212> TYPE: PRT
<213> ORGANISM: Artificial
<220> FEATURE:
<223> OTHER INFORMATION: peptide NRP-V7

<400> SEQUENCE: 17

Lys Tyr Asn Lys Ala Asn Val Phe Leu
1               5

<210> SEQ ID NO 18
<211> LENGTH: 9
<212> TYPE: PRT
<213> ORGANISM: Mus musculus

<400> SEQUENCE: 18

Leu Tyr Leu Val Cys Gly Glu Arg Leu
1               5

<210> SEQ ID NO 19
<211> LENGTH: 9
<212> TYPE: PRT
<213> ORGANISM: Mus musculus

<400> SEQUENCE: 19

Leu Tyr Leu Val Cys Gly Glu Arg Gly
1               5

<210> SEQ ID NO 20
<211> LENGTH: 9
```

```
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be Tyr or Phe
<220> FEATURE:
<221> NAME/KEY: MISC_FEATURE
<222> LOCATION: (2)..(2)
<223> OTHER INFORMATION: Xaa can be Phe, Ala, or Gln
<220> FEATURE:
<221> NAME/KEY: MISC_FEATURE
<222> LOCATION: (3)..(3)
<223> OTHER INFORMATION: Xaa can be Ile or Asp
<220> FEATURE:
<221> NAME/KEY: MISC_FEATURE
<222> LOCATION: (8)..(8)
<223> OTHER INFORMATION: Xaa can be Glu or Tyr

<400> SEQUENCE: 20

Xaa Xaa Xaa Glu Asn Tyr Leu Xaa Leu
1               5

<210> SEQ ID NO 21
<211> LENGTH: 9
<212> TYPE: PRT
<213> ORGANISM: Artificial
<220> FEATURE:
<223> OTHER INFORMATION: consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa can be Ala, Gln, Leu, or Tyr
<220> FEATURE:
<221> NAME/KEY: MISC_FEATURE
<222> LOCATION: (3)..(3)
<223> OTHER INFORMATION: Xaa can be Ile, Asp, Phe, or Leu
<220> FEATURE:
<221> NAME/KEY: MISC_FEATURE
<222> LOCATION: (7)..(7)
<223> OTHER INFORMATION: Xaa can be Ile or Leu
<220> FEATURE:
<221> NAME/KEY: MISC_FEATURE
<222> LOCATION: (8)..(8)
<223> OTHER INFORMATION: Xaa can be Glu, Trp, or Tyr
<220> FEATURE:
<221> NAME/KEY: MISC_FEATURE
<222> LOCATION: (9)..(9)
<223> OTHER INFORMATION: Xaa can be Leu or Met

<400> SEQUENCE: 21

Xaa Xaa Xaa Glu Asn Tyr Xaa Xaa Xaa
1               5

<210> SEQ ID NO 22
<211> LENGTH: 9
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be Tyr or Phe
<220> FEATURE:
<221> NAME/KEY: MISC_FEATURE
<222> LOCATION: (2)..(2)
<223> OTHER INFORMATION: Xaa can be Ala or Gln
<220> FEATURE:
<221> NAME/KEY: MISC_FEATURE
```

```
<222> LOCATION: (3)..(3)
<223> OTHER INFORMATION: Xaa can be Ile or Asp
<220> FEATURE:
<221> NAME/KEY: MISC_FEATURE
<222> LOCATION: (8)..(8)
<223> OTHER INFORMATION: Xaa can be Glu or Tyr

<400> SEQUENCE: 22

Xaa Xaa Xaa Glu Asn Tyr Leu Xaa Leu
1               5

<210> SEQ ID NO 23
<211> LENGTH: 10
<212> TYPE: PRT
<213> ORGANISM: Mus musculus

<400> SEQUENCE: 23

Phe Tyr Thr Pro Met Ser Arg Arg Glu Val
1               5                   10

<210> SEQ ID NO 24
<211> LENGTH: 9
<212> TYPE: PRT
<213> ORGANISM: Mus musculus

<400> SEQUENCE: 24

Thr Tyr Glu Ile Ala Pro Val Phe Val
1               5

<210> SEQ ID NO 25
<211> LENGTH: 9
<212> TYPE: PRT
<213> ORGANISM: Mus musculus

<400> SEQUENCE: 25

Ser Tyr Gln Pro Leu Gly Asp Lys Val
1               5

<210> SEQ ID NO 26
<211> LENGTH: 9
<212> TYPE: PRT
<213> ORGANISM: Artificial
<220> FEATURE:
<223> OTHER INFORMATION: negative control peptide

<400> SEQUENCE: 26

Thr Ser Pro Arg Asn Ser Thr Val Leu
1               5

<210> SEQ ID NO 27
<211> LENGTH: 9
<212> TYPE: PRT
<213> ORGANISM: Artificial
<220> FEATURE:
<223> OTHER INFORMATION: peptide NRP

<400> SEQUENCE: 27

Lys Tyr Asn Lys Ala Asn Trp Phe Leu
1               5

<210> SEQ ID NO 28
<211> LENGTH: 9
<212> TYPE: PRT
<213> ORGANISM: Artificial
<220> FEATURE:
<223> OTHER INFORMATION: mimotope peptide

<400> SEQUENCE: 28
```

Tyr Phe Ile Glu Asn Phe Leu Glu Leu
1               5

<210> SEQ ID NO 29
<211> LENGTH: 9
<212> TYPE: PRT
<213> ORGANISM: Artificial
<220> FEATURE:
<223> OTHER INFORMATION: mimotope peptide

<400> SEQUENCE: 29

Tyr Phe Ile Glu Asn Trp Leu Glu Leu
1               5

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
agcttccaac atgtcagccg aagtg                                           25

<210> SEQ ID NO 31
<211> LENGTH: 23
<212> TYPE: DNA
<213> ORGANISM: Artificial
<220> FEATURE:
<223> OTHER INFORMATION: primer

<400> SEQUENCE: 31
gaattctcag ggggcgaagg tgg                                             23

<210> SEQ ID NO 32
<211> LENGTH: 18
<212> TYPE: DNA
<213> ORGANISM: Artificial
<220> FEATURE:
<223> OTHER INFORMATION: primer

<400> SEQUENCE: 32
gcaccatgtc ggccaagg                                                   18

<210> SEQ ID NO 33
<211> LENGTH: 24
<212> TYPE: DNA
<213> ORGANISM: Artificial
<220> FEATURE:
<223> OTHER INFORMATION: primer

<400> SEQUENCE: 33
tctatctaca aactgattct acat                                            24

<210> SEQ ID NO 34
<211> LENGTH: 21
<212> TYPE: DNA
<213> ORGANISM: Artificial
<220> FEATURE:
<223> OTHER INFORMATION: primer

<400> SEQUENCE: 34
tttggtgagg ttgctgttgt c                                               21

<210> SEQ ID NO 35
<211> LENGTH: 20

```
<212> TYPE: DNA
<213> ORGANISM: Artificial
<220> FEATURE:
<223> OTHER INFORMATION: primer

<400> SEQUENCE: 35
agactgaaca gtgccatcat                                                    20

<210> SEQ ID NO 36
<211> LENGTH: 9
<212> TYPE: PRT
<213> ORGANISM: Mus musculus

<400> SEQUENCE: 36

Val Tyr Leu Lys Thr Asn Val Phe Leu
1               5

<210> SEQ ID NO 37
<211> LENGTH: 9
<212> TYPE: PRT
<213> ORGANISM: Artificial
<220> FEATURE:
<223> OTHER INFORMATION: consensus sequence
<220> FEATURE:
<221> NAME/KEY: MISC_FEATURE
<222> LOCATION: (1)..(3)
<223> OTHER INFORMATION: Xaa can be any amino acid
<220> FEATURE:
<221> NAME/KEY: MISC_FEATURE
<222> LOCATION: (5)..(5)
<223> OTHER INFORMATION: Xaa can be Asn or Ser
<220> FEATURE:
<221> NAME/KEY: MISC_FEATURE
<222> LOCATION: (7)..(7)
<223> OTHER INFORMATION: Xaa can be Ile, Leu, Met, Thr, or Val
<220> FEATURE:
<221> NAME/KEY: MISC_FEATURE
<222> LOCATION: (8)..(8)
<223> OTHER INFORMATION: Xaa can be Glu, His, Trp, or Tyr
<220> FEATURE:
<221> NAME/KEY: MISC_FEATURE
<222> LOCATION: (9)..(9)
<223> OTHER INFORMATION: Xaa can be Leu or Met

<400> SEQUENCE: 37

Xaa Xaa Xaa Glu Xaa Tyr Xaa Xaa Xaa
1               5

<210> SEQ ID NO 38
<211> LENGTH: 8
<212> TYPE: PRT
<213> ORGANISM: Mus musculus

<400> SEQUENCE: 38

His Glu Ala Glu Ser Tyr Met Leu
1               5

<210> SEQ ID NO 39
<211> LENGTH: 9
<212> TYPE: PRT
<213> ORGANISM: Mus musculus

<400> SEQUENCE: 39

Phe Gln Asp Glu Asn Tyr Leu Tyr Leu
1               5

<210> SEQ ID NO 40
<211> LENGTH: 9
<212> TYPE: PRT
<213> ORGANISM: Mus musculus
```

```
<400> SEQUENCE: 40

Phe Thr Asp Glu Ser Tyr Leu Glu Leu
1               5

<210> SEQ ID NO 41
<211> LENGTH: 9
<212> TYPE: PRT
<213> ORGANISM: Mus musculus

<400> SEQUENCE: 41

Thr Asn Lys Glu Asn Tyr Thr Glu Leu
1               5

<210> SEQ ID NO 42
<211> LENGTH: 9
<212> TYPE: PRT
<213> ORGANISM: Mus musculus

<400> SEQUENCE: 42

Glu Val Val Glu Ser Tyr Met Tyr Leu
1               5

<210> SEQ ID NO 43
<211> LENGTH: 9
<212> TYPE: PRT
<213> ORGANISM: Mus musculus

<400> SEQUENCE: 43

Arg Thr Ser Glu Asn Tyr Leu Glu Leu
1               5

<210> SEQ ID NO 44
<211> LENGTH: 9
<212> TYPE: PRT
<213> ORGANISM: Mus musculus

<400> SEQUENCE: 44

Val Met Leu Glu Asn Tyr Thr His Leu
1               5

<210> SEQ ID NO 45
<211> LENGTH: 9
<212> TYPE: PRT
<213> ORGANISM: Mus musculus

<400> SEQUENCE: 45

Asp Met His Glu Asn Tyr Met Glu Met
1               5

<210> SEQ ID NO 46
<211> LENGTH: 11
<212> TYPE: PRT
<213> ORGANISM: Artificial
<220> FEATURE:
<223> OTHER INFORMATION: INS-L9 peptide, chemically synthesized

<400> SEQUENCE: 46

Leu Tyr Leu Val Cys Gly Glu Arg Leu Ile His
1               5                   10

<210> SEQ ID NO 47
<211> LENGTH: 8
<212> TYPE: PRT
<213> ORGANISM: Artificial
<220> FEATURE:
```

```
<223> OTHER INFORMATION: Chemically synthesized peptide
<220> FEATURE:
<221> NAME/KEY: MISC_FEATURE
<222> LOCATION: (6)..(6)
<223> OTHER INFORMATION: X is A, I, L, or V

<400> SEQUENCE: 47

Tyr Leu Lys Thr Asn Xaa Phe Leu
1               5

<210> SEQ ID NO 48
<211> LENGTH: 9
<212> TYPE: PRT
<213> ORGANISM: Artificial
<220> FEATURE:
<223> OTHER INFORMATION: Chemically synthesized

<400> SEQUENCE: 48

Phe Leu Trp Ser Val Phe Trp Leu Ile
1               5

<210> SEQ ID NO 49
<211> LENGTH: 9
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (1)..(1)
<223> OTHER INFORMATION: X = T or A
<220> FEATURE:
<221> NAME/KEY: MISC_FEATURE
<222> LOCATION: (4)..(4)
<223> OTHER INFORMATION: X = T or G

<400> SEQUENCE: 49

Xaa Tyr Tyr Xaa Phe Leu Asn Phe Met
1               5

<210> SEQ ID NO 50
<211> LENGTH: 9
<212> TYPE: PRT
<213> ORGANISM: Artificial
<220> FEATURE:
<223> OTHER INFORMATION: Chemically synthesized
<220> FEATURE:
<221> NAME/KEY: MISC_FEATURE
<222> LOCATION: (2)..(2)
<223> OTHER INFORMATION: X = L or V
<220> FEATURE:
<221> NAME/KEY: MISC_FEATURE
<222> LOCATION: (3)..(3)
<223> OTHER INFORMATION: X = L or F
<220> FEATURE:
<221> NAME/KEY: MISC_FEATURE
<222> LOCATION: (4)..(4)
<223> OTHER INFORMATION: X = G or N
<220> FEATURE:
<221> NAME/KEY: misc_feature
<222> LOCATION: (5)..(5)
<223> OTHER INFORMATION: Xaa can be any naturally occurring amino acid

<400> SEQUENCE: 50

Leu Arg Xaa Xaa Xaa Ile Asp Leu Leu
1               5

<210> SEQ ID NO 51
<211> LENGTH: 9
<212> TYPE: PRT
<213> ORGANISM: Artificial
<220> FEATURE:
```

<223> OTHER INFORMATION: Chemnically synthesized

<400> SEQUENCE: 51

Lys Trp Cys Ala Asn Pro Asp Trp Ile
1               5

<210> SEQ ID NO 52
<211> LENGTH: 9
<212> TYPE: PRT
<213> ORGANISM: Artificial
<220> FEATURE:
<223> OTHER INFORMATION: Chemically synthesized

<400> SEQUENCE: 52

Ser Phe Cys Lys Ser Ala Ser Ile Pro
1               5

<210> SEQ ID NO 53
<211> LENGTH: 8
<212> TYPE: PRT
<213> ORGANISM: Artificial
<220> FEATURE:
<223> OTHER INFORMATION: Chemically synthesized

<400> SEQUENCE: 53

Tyr Asn Ile Ala Asn Trp Phe Leu
1               5

<210> SEQ ID NO 54
<211> LENGTH: 9
<212> TYPE: PRT
<213> ORGANISM: Mouse sp.

<400> SEQUENCE: 54

Leu Tyr Leu Val Cys Gly Glu Arg Ile
1               5

<210> SEQ ID NO 55
<211> LENGTH: 9
<212> TYPE: PRT
<213> ORGANISM: Artificial
<220> FEATURE:
<223> OTHER INFORMATION: hypothetical protein

<400> SEQUENCE: 55

Val Leu Thr Glu Asn Tyr Thr His Leu
1               5

<210> SEQ ID NO 56
<211> LENGTH: 9
<212> TYPE: PRT
<213> ORGANISM: Artificial Sequence
<220> FEATURE:
<223> OTHER INFORMATION: consensus sequence
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: X is Ile or Leu
<220> FEATURE:
<221> NAME/KEY: MISC_FEATURE
<222> LOCATION: (7)..(7)
<223> OTHER INFORMATION: X is Ile or Leu
<220> FEATURE:
<221> NAME/KEY: MISC_FEATURE
<222> LOCATION: (8)..(8)
<223> OTHER INFORMATION: X is  Glu or Tyr

```
<220> FEATURE:
<221> NAME/KEY: MISC_FEATURE
<222> LOCATION: (9)..(9)
<223> OTHER INFORMATION: X is  Leu or Met

<400> SEQUENCE: 56

Xaa Xaa Xaa Glu Asn Tyr Xaa Xaa Xaa
1               5
```